United States Patent
Alonso-Alija et al.

(10) Patent No.: US 7,087,605 B2
(45) Date of Patent: *Aug. 8, 2006

(54) 5-ETHYL-IMIDAZOTRIAZINONES

(75) Inventors: Cristina Alonso-Alija, Haan (DE); Heike Gielen, Leverkusen (DE); Martin Hendrix, Odenthal (DE); Ulrich Niewohner, deceased, late of Wermelskirchen (DE); by Maria Theresia Niewohner, legal representative, Wermelskirchen (DE); Dagmar Schauss, Solingen (DE); Hilmar Bischoff, Wuppertal (DE); Nils Burkhardt, Velbert (DE); Volker Geiss, Ratingen (DE); Karl-Heinz Schlemmer, Wuppertal (DE); Nigel J. Cuthbert, Hogshaw (GB); Mary F. Fitzgerald, Yarnton (GB); Richard Graham Sturton, Maidenhead (GB); Martin Michels, Solingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 49 days.

This patent is subject to a terminal disclaimer.

(21) Appl. No.: 10/480,947

(22) PCT Filed: May 21, 2002

(86) PCT No.: PCT/EP02/05539

§ 371 (c)(1),
(2), (4) Date: Aug. 2, 2004

(87) PCT Pub. No.: WO02/098880

PCT Pub. Date: Dec. 12, 2002

(65) Prior Publication Data

US 2004/0254187 A1      Dec. 16, 2004

(30) Foreign Application Priority Data

Jun. 1, 2001    (GB) .............................. 0113342.0

(51) Int. Cl.
*C07D 487/04*    (2006.01)
*A61K 31/53*     (2006.01)
*A61P 11/06*     (2006.01)
*A61P 11/08*     (2006.01)

(52) U.S. Cl. .................................... 514/243; 544/184
(58) Field of Classification Search ............... 544/184; 514/243

See application file for complete search history.

(56) References Cited

U.S. PATENT DOCUMENTS 4,278,673 A      7/1981  Hartley et al.

FOREIGN PATENT DOCUMENTS

| DE | 19827640 | 12/1999 |
| WO | 9924433  | 5/1999 |
| WO | 0250078  | 6/2002 |

OTHER PUBLICATIONS

West, Anthony R., Solid State Chemistry and its Applications, Wiley, New York, 1988, pp. 358 & 365.*
See Lucas et al. Pharmacological Reviews 52 (3), 375-413, 2000.*
Dyke, J.J. and Montant, J.G., "The therapeutic potential of PDE 4 inhibitors," Exp. Opin. Invest. Drugs 8, 1301-1325 (1999).
Barnette, M. S., "PDE 4 inhibitors in asthma and chronic obstructive pulmonary disease," Progress in Drug Research, Birkhäuser Verlag, Basel, 1999, pp. 193-229.

* cited by examiner

*Primary Examiner*—Venkataraman Balasubramanian

(57) ABSTRACT

The invention relates to novel 5-Ethyl-imidazotriazinones, processes for their preparation and their use in medicaments, esp. for the treatment and/or prophylaxis of inflammatory processes and/or immune diseases.

7 Claims, No Drawings

5-ETHYL-IMIDAZOTRIAZINONES

The invention relates to novel 5-Ethyl-imidazotriazinones, processes for their preparation and their use in medicaments, esp. for the treatment and/or prophylaxis of inflammatory processes and/or immune diseases.

Phosphodiesterases (PDEs) are a family of enzymes responsible for the metabolism of the intracellular second messengers cAMP (cyclic adenosine monophosphate) and cGMP (cyclic guanosine monophosphate). PDE 4, as a cAMP specific PDE, catalyses the conversion of cAMP to AMP and is the major if not sole isoform of the phosphodiesterase enzymes present in inflammatory and immune cell types. Inhibition of this enzyme leads to the accumulation of cAMP which, in these cells, leads to the inhibition of a range of pro-inflammatory functions. Uncontrolled production of inflammatory mediators can lead to acute and chronic inflammation, tissue damage, multi-organ failures and to death. Additionally, elevation of phagocyte cAMP leads to inhibition of oxygen radical production. This cell function is more sensitive than others such as aggregation or enzyme release.

It is now recognised that both asthma and COPD (Chronic obstructive pulmonary disease) are chronic inflammatory lung diseases. In the case of asthma the eosinophil is the predominant infiltrating cell. Subsequent release of superoxide radicals as well as damaging cationic proteins from these infiltrating cells are believed to play a role in the progression of the disease and development of airway hyper-reactivity.

By contrast, in COPD the neutrophil is the predominant inflammatory cell type found in the lungs of sufferers. The action of mediators and proteases released in the environment of the lung is believed to result in the irreversible airway obstruction seen in COPD. In particular the action of proteases in degrading the lung matrix results in fewer alveoli and is likely to be the major cause of accelerated long term lung function decline seen in this disease.

Treatment with a PDE 4 inhibitor is expected to reduce the inflammatory cell burden in the lung in both of these diseases [M. S. Barnette, "PDE 4 inhibitors in asthma and chronic obstructive pulmonary disease", in: Progress in Drug Research, Birkhäuser Verlag, Basel, 1999, pp. 193–229; H. J. Dyke and J. G. Montana, "The therapeutic potential of PDE 4 inhibitors", Exp. Opin. Invest. Drugs 8, 1301–1325 (1999)].

WO 99/24433 and WO 99/67244 describe 2-phenyl-imidazotriazinones as synthetic intermediates for the synthesis of 2-(aminosulfonyl-phenyl)-imidazotriazinones as inhibitors of cGMP-metabolizing phosphodiesterases.

U.S. Pat. No. 4,278,673 discloses 2-aryl-imidazotriazinones with cAMP phosphodiesterase inhibitory activity for the treatment of i.a. asthma.

The present invention relates to compounds of the general formula (I)

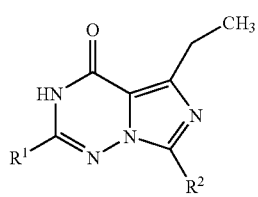

(I)

in which $R^1$ denotes $(C_6–C_{10})$-aryl, which is optionally substituted by identical or different residues selected from the group consisting of halogen, $(C_1–C_4)$-alkyl, trifluoromethyl, cyano, nitro and trifluoromethoxy, or denotes $(C_1–C_8)$-alkyl, which is optionally substituted by 3- to 10-membered carbocyclyl, or denotes 3- to 10-membered carbocyclyl, which is optionally substituted by identical or different $(C_1–C_4)$-alkyl residues, and $R^2$ denotes 3- to 10-membered carbocyclyl or carbon-bonded, 4- to 10-membered heterocyclyl, whereby carbocyclyl and heterocyclyl are optionally substituted by identical or different residues selected from the group consisting of $(C_1–C_6)$-alkyl, $(C_1–C_6)$-alkoxy, $(C_1–C_6)$-alkoxycarbonyl, benzyloxycarbonyl, $(C_1–C_6)$-alkylcarbonyl, $(C_4–C_7)$-cycloalkylcarbonyl, benzoyl, hydroxy, halogen, trifluoromethyl and oxo, or denotes $(C_2–C_{10})$-alkyl, which is optionally substituted by identical or different residues selected from the group consisting of $(C_1–C_6)$-alkoxy, hydroxy, halogen, 3- to 10-membered carbocyclyl and oxo.

Another embodiment of the invention relates to compounds of the general formula (I), in which $R^1$ denotes naphthyl, or denotes phenyl, which is optionally substituted by identical or different halogen atoms, and $R^2$ has the meaning indicated above.

Another embodiment of the invention relates to compounds of the general formula (I), in which $R^1$ has the meaning indicated above, and $R^2$ denotes $(C_4–C_7)$-cycloalkyl, which is optionally substituted up to two times by identical or different $(C_1–C_5)$-alkyl residues, or denotes $(C_3–C_8)$-alkyl, which is optionally substituted by a $(C_4–C_7)$-cycloalkyl.

The compounds according to this invention can also be present in the form of their salts, hydrates and/or solvates.

In general, salts with organic or inorganic bases or acids may be mentioned here.

Physiologically acceptable salts are preferred in the context of the present invention.

Physiologically acceptable salts can also be salts of the compounds according to this invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalene-disulphonic acid. Preferred pyridinium salts are salts in combination with halogen.

The compounds according to this invention can exist in stereoisomeric forms which either behave as image and mirror image (enantiomers), or which do not behave as image and mirror image (diastereomers). The invention relates both to the enantiomers and to the racemates, as well as the pure diastereomer and mixtures thereof. The racemates, like the diastereomers, can be separated into the stereoisomerically uniform constituents according to known methods.

Especially preferred are compounds of the general formula (I), wherein $R^1$ denotes 1-naphthyl or 3-halo-phenyl.

Hydrates of the compounds of the invention are stoichiometric compositions of the compounds with water, such as for example hemi-, mono-, or dihydrates.

Solvates of the compounds of the invention or their salts are stoichiometric compositions of the compounds with solvents.

$(C_1-C_6)$-Alkoxy in general represents a straight chain or branched alkoxy residue with 1 to 6 carbon atoms. The following alkoxy residues are mentioned by way of example: methoxy, ethoxy, n-propoxy, isopropoxy, tert.butoxy, n-pentoxy and n-hexoxy. Alkoxy residues with 1 to 4 carbon atoms are preferred. Alkoxy residues with 1 to 3 carbon atoms are especially preferred.

$(C_2-C_{10})$-Alkyl, $(C_1-C_8)$-alkyl, $(C_1-C_6)$-alkyl, and $(C_1-C_4)$-alkyl in general represent straight chain or branched alkyl residues with 2 to 10, 1 to 8, 1 to 6 or 1 to 4 carbon atoms, respectively. The alkyl residues can be saturated or partially unsaturated, i.e. contain one or more double and/or triple bonds. Saturated alkyl residues are preferred. The following alkyl residues are mentioned by way of example: methyl, ethyl, n-propyl, isopropyl, allyl, propargyl, tert.butyl, pentyl, hexyl, heptyl, octyl, nonyl, and decyl.

$C_6-C_{10}$-Aryl in general represents an aromatic residue with 6 to 10 carbon atoms. Phenyl and naphthyl are preferred.

3- to 10-membered carbocyclyl in general represents a mono- or polycyclic, carbocyclic residue with 3 to 10 ring atoms. 3- to 8-membered carbocyclyl is preferred. Mono- and bicyclic carbocyclyl residues are preferred. Especially preferred are monocyclic carbocyclyl residues. The carbocyclyl residues can be saturated or partially unsaturated. Saturated carbocyclyl residues are preferred. Especially preferred are $(C_3-C_{10})$-cycloalkyl and $(C_4-C_7)$-cycloalkyl residues. The following carbocyclyl residues are mentioned by way of example: cyclopropyl, cyclobutyl, cyclopentyl, cyclopentenyl, cyclohexyl, cycloheptyl, norborn-1-yl, norborn-2-yl, norborn-7-yl, norborn-2-en-7-yl, cyclooctyl, cubyl, cyclononyl, cyclodecyl, decalinyl, adamant-1-yl, adamant-2-yl.

$(C_3-C_{10})$-Cycloalkyl and $(C_4-C_7)$-cycloalkyl in general represent a cycloalkyl residue with 3 to 10 or 4 to 7 carbon atoms, respectively. The following cycloalkyl residues are mentioned by way of example: cyclopropyl, cyclobutyl, cyclopentyl, cyclopentenyl, cyclohexyl, cycloheptyl, cyclooctyl, cyclononyl, or cyclodecyl.

Halogen in general represents fluoro, chloro, bromo and iodo. Fluoro, chloro, and bromo are preferred. Fluoro, and chloro are especially preferred.

Carbon-bonded, 4- to 10-membered heterocyclyl in general represents a mono- or polycyclic, heterocyclic residue with 4 to 10 ring atoms, whereby the heterocycle is bound through a ring carbon ring atom. The heterocyclyl residue can contain up to 3, preferentially 1, hetero ring atoms selected from nitrogen, oxygen, sulfur, —SO—, —SO$_2$—. Oxygen is preferred. Mono- and bicyclic heterocyclyl residues are preferred. Especially preferred are monocyclic heterocyclyl residues. The heterocyclyl residues can be saturated or partially unsaturated. Saturated heterocyclyl residues are preferred. The following heterocyclyl residues are mentioned by way of example: oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl. Oxo in general represents a double-bonded oxygen atom.

Unless specified otherwise, when groups in compounds of the invention are optionally substituted, substitution by up to three identical or different residues is generally preferred.

The invention furthermore provides a process for preparing the compounds of the general formula (I) according to the invention, characterized in that compounds of the general formula (II)

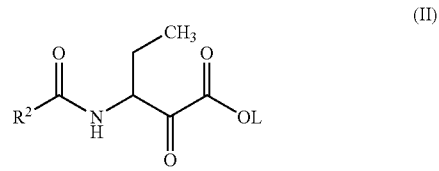

(II)

in which $R^2$ is as defined above and

L represents straight-chain or branched alkyl having up to 4 carbon atoms, are condensed with compounds of the general formula (III)

(III)

in which $R^1$ is as defined above, preferably using ethanol as a solvent, to the compounds of the general formula (IV),

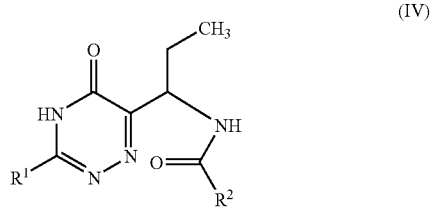

(IV)

in which $R^1$ and $R^2$ are as defined above, which can optionally after isolation be reacted with a dehydrating agent, preferably phosphorus oxytrichloride, to yield the compounds of the general formula (I).

The compounds of the general formula (IV) can alternatively be prepared by

[A] condensation of compounds of the general formula (IIa),

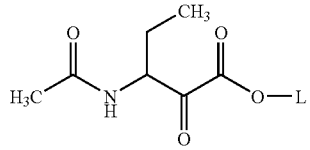

in which
L is as defined above,
with compounds of the general formula (III) to compounds of the general formula (IVa),

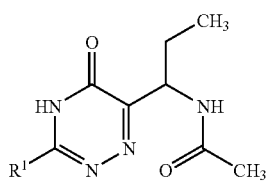

in which
$R^1$ is as defined above,
preferably using ethanol as a solvent,

[B] followed by hydrolysis of the compounds of the general formula (IVa) to compounds of the general formula (V),

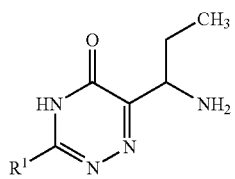

in which
$R^1$ is as defined above,

[C] and finally by condensation of the compounds of the general formula (V) with compounds of the general formula (VI),

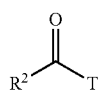

in which
$R^2$ is as defined above, and
T represents a leaving group, preferably chlorine.

The process according to the invention can be illustrated using the following scheme as an example:

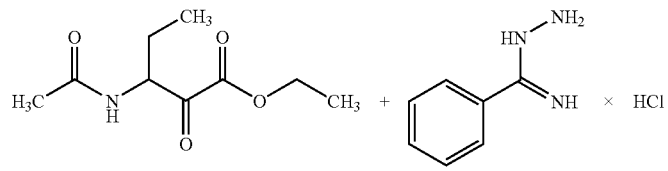

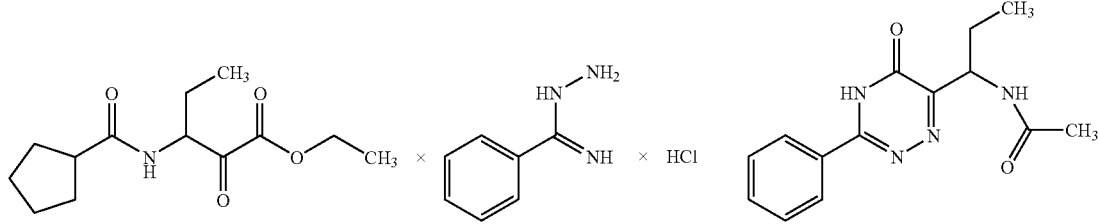

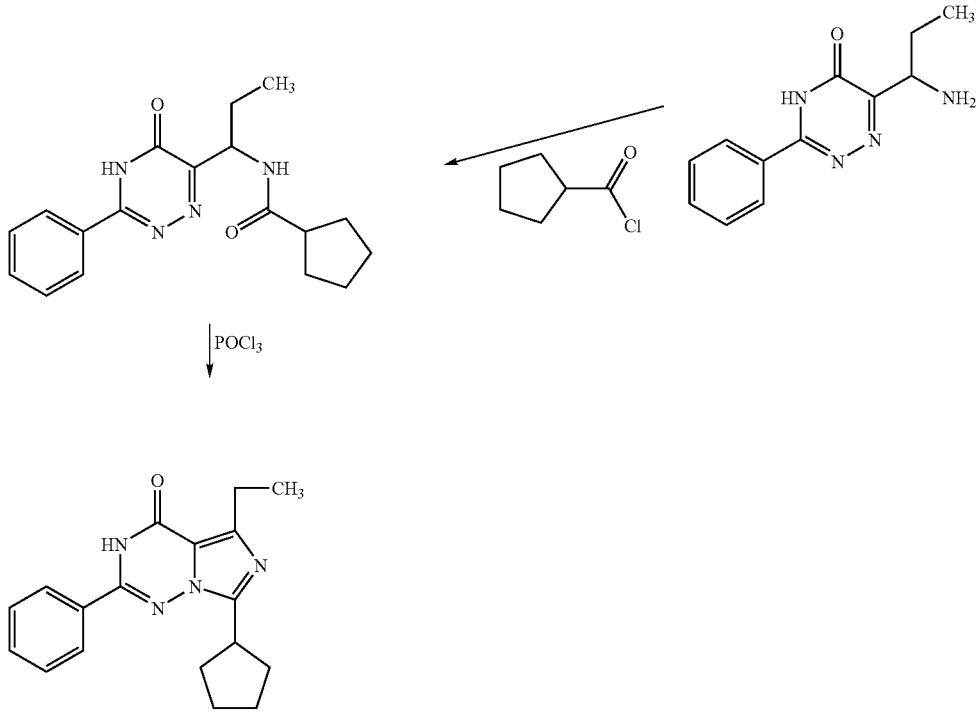

Solvents which are suitable for the individual steps are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethane, trichloroethylene or chlorobenzene, or ethyl acetate, dimethylformamide, hexamethylphosphoric triamide, acetonitrile, acetone, dimethoxyethane or pyridine. It is also possible to use mixtures of the above-mentioned solvents. Particular preference is given to ethanol for the reaction II/IIa+III→IV/IVa and dichloroethane for the cyclisation IV→I.

The reaction temperature can generally be varied within a relatively wide range. In general, the reaction is carried out in a range of from −20° C. to 200° C., preferably of from 0° C. to 100° C.

The process steps according to the invention are generally carried out under atmospheric pressure. However, it is also possible to operate under superatmospheric pressure or under reduced pressure (for example, in a range of from 0.5 to 5 bar).

The compounds of the general formula (IVa) are preferably hydrolysed to compounds of the general formula (V) under acidic conditions as for example in refluxing 2N hydrochloric acid.

The compounds of the general formula (V) are condensed with the compounds of the general formula (VI) to compounds of the general formula (IV) in inert solvents, if appropriate in the presence of a base.

Suitable inert solvents are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, hexamethylphosphoric triamide, acetonitrile, acetone, dimethoxyethane or pyridine. It is also possible to use mixtures of the above-mentioned solvents.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or ($C_1$–$C_4$)-alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (V).

The reaction temperature can generally be varied within a relatively wide range. In general, the reaction is carried out in a range of from −20° C. to 200° C., preferably of from 0° C. to 100° C.

Some of the compounds of the general formula (II) are known, or they are novel, and they can then be prepared by converting compounds of the general formula (VI)

$$R^2\text{—CO-T} \quad (VI)$$

in which
$R^2$ is as defined above
and
T represents halogen, preferably chlorine, initially by reaction with α-amino-butyric acid in inert solvents, if appropriate in the presence of a base and trimethylsilyl chloride, into the compounds of the general formula (VII),

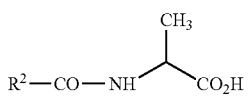

(VII)

in which
R² is as defined above,
and finally reacting with the compound of the formula (VIII)

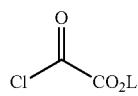

(VIII)

in which
L is as defined above,
in inert solvents, if appropriate in the presence of a base.

The compounds of the general formula (IIa) can be prepared analogously.

Suitable solvents for the individual steps of the process are the customary organic solvents which do not change under the reaction conditions. These preferably include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, dimethylformamide, hexamethylphosphoric triamide, acetonitrile, acetone, dimethoxyethane or pyridine. It is also possible to use mixtures of the above-mentioned solvents. Particular preference is given to dichloromethane for the first step and to a mixture of tetrahydrofuran and pyridine for the second step.

Suitable bases are generally alkali metal hydrides or alkali metal alkoxides, such as, for example, sodium hydride or potassium tert-butoxide, or cyclic amines, such as, for example, piperidine, pyridine, dimethylaminopyridine or ($C_1$–$C_4$)-alkylamines, such as, for example, triethylamine. Preference is given to triethylamine, pyridine and/or dimethylaminopyridine.

The base is generally employed in an amount of from 1 mol to 4 mol, preferably from 1.2 mol to 3 mol, in each case based on 1 mol of the compound of the formula (X).

The reaction temperature can generally be varied within a relatively wide range. In general, the reaction is carried out in a range of from −20° C. to 200° C., preferably of from 0° C. to 100° C.

The compounds of the general formulae (VI) and (VIII) are known per se, or they can be prepared by customary methods.

The compounds of the general formula (III) are known or can be prepared by reacting compounds of the general formula (IX)

R¹—Y    (IX)

in which
R¹ is as defined above, and
Y represents a cyano, carboxyl, methoxycarbonyl or ethoxycarbonyl group, with ammonium chloride in toluene and in the presence of trimethylaluminium in hexane in a temperature range of from −20° C. to room temperature, preferably at 0° C. and atmospheric pressure, and reacting the resulting amidine, if appropriate in situ, with hydrazine hydrate.

The compounds of the general formula (IX) are known per se, or they can be prepared by customary methods.

The compounds of the general formula (I) inhibit the PDE 4 resident in the membranes of human neutrophils. One measured functional consequence of this inhibition was inhibition of superoxide anion production by stimulated human neutrophils.

The compounds of the general formula (I) can therefore be employed in medicaments for the treatment of inflammatory processes, esp. acute and chronic inflammatory processes, and/or immune diseases.

The compounds according to the invention are preferably suitable for the treatment and prevention of inflammatory processes, i.e. acute and chronic inflammatory processes, and/or immune diseases, such as emphysema, alveolitis, shock lung, all kinds of chronic obstructive pulmonary diseases (COPD), adult respiratory distress syndrome (ARDS), asthma, bronchitis, cystic fibrosis, eosinophilic granuloma, arteriosclerosis, arthrosis, inflammation of the gastro-intestinal tract, myocarditis, bone resorption diseases, reperfusion injury, Crohn's disease, ulcerative colitis, systemic lupus erythematosus, type I diabetes mellitus, psoriasis, anaphylactoid purpura nephritis, chronic glomerulonephritis, inflammatory bowel disease, atopic dermatitis, other benign and malignant proliferative skin diseases, allergic rhinitis, allergic conjunctivitis, vernal conjunctivitis, arterial restenosis, sepsis and septic shock, toxic shock syndrome, grafts vs. host reaction, allograft rejection, treatment of cytokine-mediated chronic tissue degeneration, rheumatoid arthritis, arthritis, rheumatoid spondylitis, osteoarthritis, coronary insufficiency, myalgias, multiple sclerosis, malaria, AIDS, cachexia, prevention of tumor growth and tissue invasion, leukemia, depression, memory impairment and acute stroke. The compounds according to the invention are additionally suitable for reducing the damage to infarct tissue after reoxygenation.

The compounds of formula (I) according to the invention can be used as active compound components for the production of medicaments. For this, they can be converted into the customary formulations such as tablets, coated tablets, aerosols, pills, granules, syrups, emulsions, suspensions and solutions in a known manner using inert, non-toxic, pharmaceutically suitable excipients or solvents. Preferably, the compounds according to the invention are used here in an amount such that their concentration in the total mixture is approximately 0.5 to approximately 90% by weight, the concentration, inter alia, being dependent on the corresponding indication of the medicament.

The above mentioned formulations are produced, for example, by extending the active compounds with solvents and/or excipients having the above properties, where, if appropriate, additionally emulsifiers or dispersants and, in the case of water as the solvent, alternatively an organic solvent, have to be added.

Administration is carried out in a customary manner, preferably orally, transdermally or parenterally, for example perlingually, buccally, intravenously, nasally, rectally or inhalationally.

For human use, in the case of oral administration, it is recommendable to administer doses of from 0.001 to 50 mg/kg, preferably of 0.01 mg/kg–20 mg/kg. In the case of parenteral administration, such as, for example, intravenously or via mucous membranes nasally, buccally or inhalationally, it is recommendable to use doses of 0.001 mg/kg–0.5 mg/kg.

In spite of this, if appropriate, it may be necessary to depart from the amounts mentioned above, namely depending on the body weight or the type of administration route, on the individual response towards the medicament, the manner of its formulation and the time or interval at which administration takes place. Thus, in some cases it may be sufficient to manage with less than the above mentioned minimum amount, while in other cases the upper limit mentioned must be exceeded. In the case of the administration of relatively large amounts, it may be recommendable to divide these into several individual doses over the course of the day.

Test Descriptions

1. Preparation of Human PMN

Human PMN (polymorphonuclear neutrophil leucocytes) are readily purified from peripheral blood. Phosphodiesterase in these cells is predominantly located in the membrane fraction. Inhibitory potency of compounds against this preparation correlate well with the anti-inflammatory activity as measured by inhibiton of superoxide production.

Blood was taken from healthy subjects by venous puncture and neutrophils were purified by dextran sedimentation and density gradient centrifugation on Ficoll Histopaque and resuspended in the buffered medium.

2. Assay of Human PMN Phosphodiesterase

This was performed as a particulate fraction from human PMN essentially as described by Souness and Scott [Biochem. J. 291, 389–395 (1993)]. Particulate fractions were treated with sodium vanadate/glutathione as described by the authors to express the discrete stereospecific site on the phosphodiesterase enzyme. The prototypical PDE 4 inhibitor, rolipram, had an $IC_{50}$ value in the range 450 nM–1500 nM, thus defining this preparation as the so-called "low affinity" [L] form. The preparation examples had $IC_{50}$ values within the range of 0.1 nM–10,000 nM.

3. Inhibition of FMLP-stimulated Production of Superoxide Radical Anions

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells.

After addition of cytochalasin b (5 µg×ml$^{-1}$) the plate was incubated for 5 min. at 37° C. Neutrophils were then stimulated by addition of $4 \times 10^{-8}$ M FMLP (N-Formyl-Met-Leu-Phe) and superoxide generation measured as superoxide dismutase inhibitable reduction of cytochrome C by monitoring the $OD_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - (Rx - Rb)]}{(Ro - Rb)} \times 100$$

Rx=Rate of the well containing the compound according to the invention
Ro=Rate in the control well
Rb=Rate in the superoxide dismutase containing blank well 4. Assay of Binding to the Rolipram Binding Site (PDE 4 High Affinity Site; "H-PDE 4 Form") in Rat Brain Membranes:

The activity of compounds on the PDE 4 high affinity site ("H-PDE 4 form") is readily measured by determining their potency for displacement of [$^3$H]-rolipram from its binding site in rat brain membranes. Activity at this site is believed to be a measure of side effect potential (e.g. stimulation of stomach acid secretion, nausea and emesis).

The rolipram binding site assay was performed essentially as described by Schneider et al. [Eur. J. Pharmacol. 127, 105–115 (1986)].

5. Lipopolysaccharide (LPS)—Induced Neutrophil Influx into Rat Lung

Intranasal administration of LPS to rats causes a marked influx of neutrophils into the lungs measurable by histological or biochemical (myeloperoxidase content of the cell pellet) analysis of the bronchoalveolar lavage fluid 24 h later. Rats were treated with test compound or vehicle administered by the oral route 1 h prior to and 6 h after administration of intranasal LPS. 24 hours later animals were euthanatized and their lungs lavaged with PBS (phosphate buffered saline). Neutrophil and total cell numbers were analysed.

6. Emetic Potential in the Marmoset

Vehicle or test compound was administered by the oral route to conscious marmosets. Animals were observed for emetic episodes or abnormal behaviour for 1 h post dosing. In some experiments, if no adverse response was seen, a separate group of animals was tested at ½ log dose higher until emesis or abnormal behaviour was observed. The highest dose at which no abnormal behavior or emetic episodes occurred was recorded as the NOEL.

Materials and Methods

| LC-MS method A: | | | | |
|---|---|---|---|---|
| LC-parameters | solution A acetonitrile | | | |
| | solution B 0.3 g 30% HCl/1 water | | | |
| | column oven 50° C.; | | | |
| | column Symmetry C18 2.1 × 150 mm | | | |
| gradient: | time [min] | % A | % B | flow [ml/min] |
| | 0 | 10 | 90 | 0.9 |
| | 3 | 90 | 10 | 1.2 |
| | 6 | 90 | 10 | 1.2 |
| LC-MS method B: | | | | |
| LC-parameters | solution A acetonitrile/0.1% formic acid | | | |
| | solution B water/0.1% formic acid | | | |
| | column oven 40° C.; | | | |
| | column Symmetry C18 2.1 × 50 mm | | | |

-continued

| gradient: | time [min] | % A | % B | flow [ml/min] |
|---|---|---|---|---|
| | 0 | 10 | 90 | 0.5 |
| | 4 | 90 | 10 | 0.5 |
| | 6 | 90 | 10 | 0.5 |
| | 6.1 | 10 | 90 | 1.0 |
| | 7.5 | 10 | 90 | 0.5 |

GC-MS method A:

| Column: | HP-5 30 m × 320 μm × 0.25 μm |
|---|---|
| Carrier Gas: | Helium |
| Mode: | Constant flow, initial flow: 1.5 ml/min |
| Oven ramp: | initial temp: 60° C. |
| | initial time: 1 min |
| | rate: 14° C./min up to 300° C., then 300° C. 2 min |

Unless specified otherwise, the following chromatographic conditions were applied: chromathography was performed on silica gel Si 60; for flash chromatography, the usual conditions were followed as described in Still, *J. Org. Chem.* 43, 2923 (1978); mixtures of dichloromethane and methanol or cyclohexane and ethylacetate were used as eluants.

Unless specified otherwise, reactions were executed under an argon atmosphere and under anhydrous conditions.

Abbreviations
HPLC=high performance liquid chromatography
MS=mass spectroscopy
NMR=nuclear magnetic resonance spectroscopy
LC-MS=liquid chromatography combined with mass spectroscopy
GC-MS=gas chromatography combined with mass spectroscopy
MeOH=methanol
DMSO=dimethylsulfoxide
Starting Materials

EXAMPLE 1A 2-(Acetylamino)butanoic acid

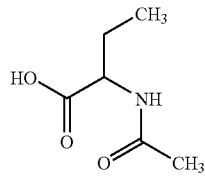

163 g (1.58 mol) 2-aminobutanoic acid are dissolved in acetic acid, and 242 g (2.37 mol) acetic anhydride are added dropwise. The mixture is stirred for 2 h at 100° C. until completion of reaction, then the solution evaporated to dryness in vacuo. The solid residue is suspended in ethyl acetate, filtered and washed with diethyl ether.

Yield: 220 g (95.9%)

$^1$H-NMR (Methanol-d$_4$): δ=0.97 (t, 3H), 1.65–1.93 (m, 2H), 1.99 (s, 3H), 4.29 (q, 1H) ppm.

EXAMPLE 2A

Ethyl 3-(acetylamino)-2-oxopentanoate

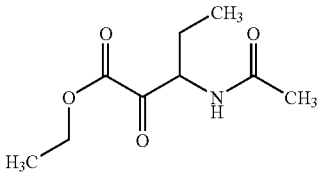

9.2 g (63.4 mmol) 2-(acetylamino)butanoic acid are suspended in 120 ml tetrahydro-furane and heated to reflux together with 15.0 g (190 mmol) pyridine and a bit of N,N-dimethylaminopyridine. While heating at reflux, 17.3 g (127 mmol) ethyl chloro(oxo)acetate are added dropwise. The reaction mixture is heated at reflux until no more evolution of gas can be observed. After cooling down to room temperature, the reaction mixture is added to ice water and the organic phase extracted with ethyl acetate. The dried organic phase is evaporated to dryness in vacuo, dissolved in ethanol and the solution directly used for the next reaction.

EXAMPLE 3A

3-Bromobenzenecarboximidamide hydrochloride

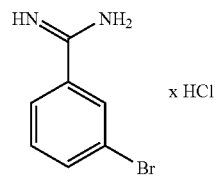

1.18 g (22 mmol, 2 equiv.) ammonium chloride are suspended in 40 ml of dry toluene under an argon atmosphere, and the mixture is cooled to 0° C. 11 ml (22 mmol, 2 equiv.) of a 2M solution of trimethylaluminium in hexane are added dropwise, and the reaction mixture is stirred at room temperature until no more evolution of gas is observed. After addition of 2.0 g (11 mmol, 1 equiv.) 3-bromobenzonitrile, the mixture is stirred at 80° C. bath temperature over night. It is then cooled down to 0° C. and 50 ml of methanol are added with subsequent stirring of 1 hour at room temperature. After filtration, the solid is washed with methanol for several times, the solution is evaporated to dryness in vacuo and the residue washed with methanol.

Yield: 2.02 g (78%)

$^1$H-NMR (DMSO-d$_6$, 300 MHz): δ=7.6 (m, 1H), 7.8 (m, 1H), 8.0 (m, 1H), 8.1 (s, 1H) ppm.

EXAMPLE 4A

4-Fluorobenzenecarboximidamide hydrochloride

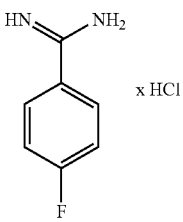

In analogy to the procedure for Example 3A, 2.0 g (16.5 mmol) 4-fluorobenzonitrile and proportionate amounts of the other reagents are used.

Yield: 2.9 g (100%)

$^1$H-NMR (DMSO-$d_6$, 200 MHz): δ=7.5 (m, 2H), 8.0 (m, 2H) ppm.

EXAMPLE 5A

Cyclopropanecarboximidamide hydrochloride

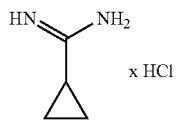

In analogy to the procedure for Example 3A, 6.71 g (100 mmol) cyclopropanecarbonitrile and proportionate amounts of the other reagents are used.

Yield: 7.3 g (61%)

GC/MS (method A): retention time 3.42 min., m/z 85 [M+H]$^+$

EXAMPLE 6A

Cyclopentanecarboximidamide hydrochloride

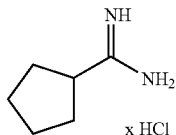

In analogy to the procedure for Example 3A, 7.51 g (79.0 mmol) cyclopentanecarbonitrile and proportionate amounts of the other reagents are used.

Yield: 3.9 g (33%)

LC-MS (method A): retention time 0.42 min., m/z 113 [M+H]$^+$

EXAMPLE 7A 2,2-Dimethylpropanimidamide hydrochloride

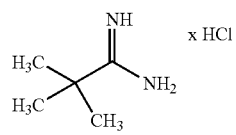

In analogy to the procedure for Example 3A, 8.31 g (100 mmol) pivalonitrile and proportionate amounts of the other reagents are used. The crude product is used in the next step without further purification.

Yield: 6 g crude product

EXAMPLE 8A

3-Nitrobenzenecarboximidamide hydrochloride

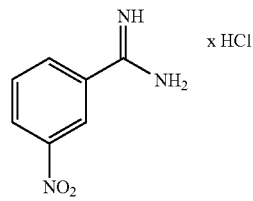

In analogy to the procedure for Example 3A, 30.0 g (203 mmol) 3-nitrobenzonitrile and proportionate amounts of the other reagents are used.

Yield: 24.5 g (47%)

LC-MS (method A): retention time 0.40 min., m/z 166 [M+H]$^+$

EXAMPLE 9A

1-Naphthalenecarboximidamide hydrochloride

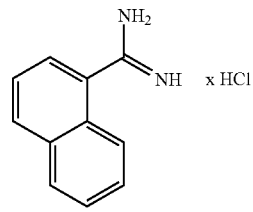

14 g (261 mmol, 2 equiv.) ammonium chloride are suspended in 150 ml of dry toluene under an argon athmosphere, and the mixture is cooled to 0° C. 130 ml (260 mmol, 2 equiv.) of a 2M solution of trimethylaluminium in hexane are added dropwise, and the reaction mixture is stirred at room temperature until no more evolution of gas is observed. After addition of 20 g (130 mmol, 1 equiv.) 1-cyanonaphthalene, the mixture is stirred at 80° C. bath temperature over night. The mixture is cooled and poured into a slurry of silica in methylene chloride. After filtration, the solid is washed with methanol for several times, the solution is evaporated to dryness in vacuo and the residue washed with methanol. The combined filtrates are pooled and stirred in a mixture of methylene chloride containing 10% methanol.

Yield: 9.88 g (37%)

$^1$H-NMR (DMSO-$d_6$, 300 MHz): δ=7.6–7.8 (m, 4H), 8.0 (d, 1H), 8.1 (m, 1H), 8.2 (d, 1H) ppm, 9.5 (br s, 4H) ppm.

EXAMPLE 10A

N-{1-[3-(3-Bromophenyl)-5-oxo-4,5-dihydro-1,2,4-triazin-6-yl]propyl}acetamide

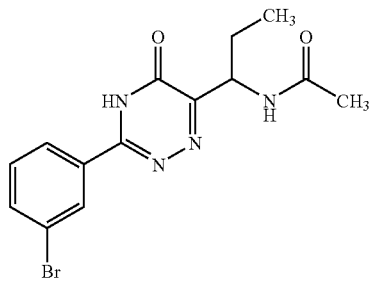

2.02 (8.6 mmol, 1 equiv.) 3-bromobenzenecarboximidamide hydrochloride are suspended in 50 ml of ethanol and 1.47 g (10.2 mmol, 1.2 equiv.) hydrazine hydrate are added. After stirring at room temperature for 1 hour, 2.59 g (13 mmol, 1.5 equiv) of the compound of Example 2A, dissolved in 10 ml of ethanol, are added. The reaction mixture is stirred at 80° C. (bath temperature) for 4 hours and then at room temperature over night. The mixture is evaporated to dryness in vacuo and the product is purified by chromatography (flash or column chromatography or preparative HPLC).

Yield: 758 mg (25%)

$^1$H-NMR (DMSO-d$_6$, 200 MHz): δ=0.9 (t, 3H), 1.6 (m, 1H), 1.8 (m, 1H), 1.9 (s, 3H), 4.9 (m, 1H), 7.5 (m, 1H), 7.8 (m, 1H), 8.0 (m, 1H), 8.2 (m, 2H), 14.1 (br. s, 1H) ppm.

EXAMPLE 11A

N-{1-[3-(4-Fluorophenyl)-5-oxo-4,5-dihydro-1,2,4-triazin-6-yl]propyl}acetamide

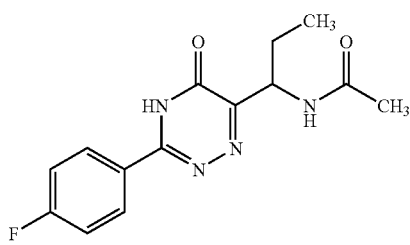

In analogy to the procedure for Example 10A, 2.0 g (11.4 mmol) 4-fluorobenzenecarboximidamide hydrochloride and proportionate amounts of the other reagents are used.

Yield: 1.47 g (44%)

$^1$H-NMR (DMSO-d$_6$, 300 MHz): δ=0.9 (t, 3H), 1.6 (m, 1H), 1.8 (m, 1H), 1.9 (s, 3H), 4.9 (m, 1H), 7.5 (m, 2H), 8.1 (m, 3H), 14.1 (br. s, 1H) ppm.

EXAMPLE 12A

N-{1-[3-(3-Fluorophenyl)-5-oxo-4,5-dihydro-1,2,4-triazin-6-yl]propyl}acetamide

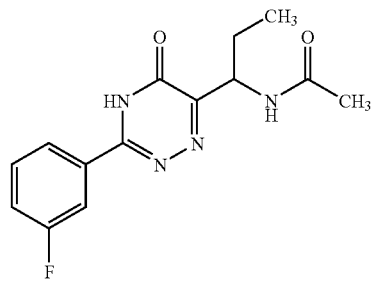

In analogy to the procedure for Example 10A, 2.0 g (11.4 mmol) 3-fluorobenzenecarboximidamide hydrochloride and proportionate amounts of the other reagents are used.

Yield: 781 mg (23%)

$^1$H-NMR (DMSO-d$_6$, 300 MHz): δ=0.9 (t, 3H), 1.6 (m, 1H), 1.8 (m, 1H), 1.9 (s, 3H), 4.9 (m, 1H), 7.5 (m, 1H), 7.7 (m, 1H), 7.8 (m, 1H), 7.9 (m, 1H), 8.2 (d, 1H), 14.1 (br. s, 1H) ppm.

EXAMPLE 13A

N-{1-[3-(3-Chlorophenyl)-5-oxo-4,5-dihydro-1,2,4-triazin-6-yl]propyl}acetamide

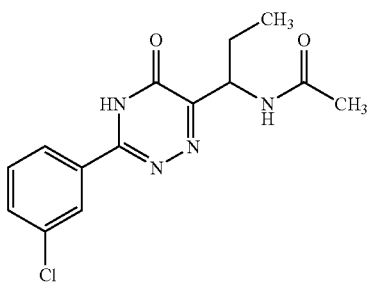

In analogy to the procedure for Example 10A, 1.5 g (7.9 mmol) 3-chlorobenzenecarboximidamide hydrochloride and proportionate amounts of the other reagents are used.

Yield: 441 mg (18%)

$^1$H-NMR (DMSO-d$_6$, 300 MHz): δ=0.9 (t, 3H), 1.6 (m, 1H), 1.8 (m, 1H), 1.9 (s, 3H), 4.9 (m, 1H), 7.6 (m, 1H), 7.7 (m, 1H), 8.0 (m, 1H), 8.1 (m, 1H), 8.2 (d, 1H), 14.1 (br. s, 1H) ppm.

EXAMPLE 14A

N-{1-[3-(2-Bromophenyl)-5-oxo-4,5-dihydro-1,2,4-triazin-6-yl]propyl}acetamide

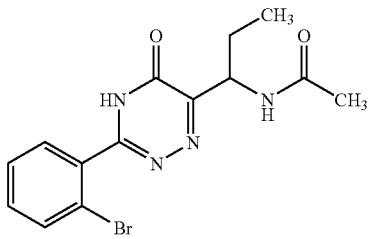

In analogy to the procedure for Example 10A, 1.64 g (7.0 mmol) 2-bromobenzenecarboximidamide hydrochloride and proportionate amounts of the other reagents are used.

Yield: 1.0 g (41%)

LC/MS (B): MS (ES+): 351 (M+H$^+$), retention time 2.34 min.

EXAMPLE 15A

N-[1-(3-Cyclohexyl-5-oxo-4,5-dihydro-1,2,4-triazin-6-yl)propyl]acetamide

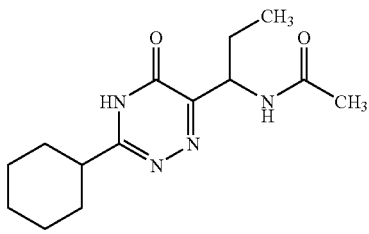

In analogy to the procedure for Example 10A, 1.50 g (9.2 mmol) cyclohexanecarboximidamide hydrochloride and proportionate amounts of the other reagents are used.

Yield: 1.17 g (46%)

¹H-NMR (DMSO-d₆, 200 MHz): δ=0.9 (t, 3H), 1.2 (m, 3H), 1.5 (m, 3H), 1.8 (m, 4H), 1.9 (s, 3H), 2.5 (m, 1H), 4.8 (m, 1H), 8.1 (d, 1H), 13.4 (br.s, 1H) ppm.

EXAMPLE 16A

N-{1-[3-(4-Bromophenyl)-5-oxo-4,5-dihydro-1,2,4-triazin-6-yl]propyl}acetamide

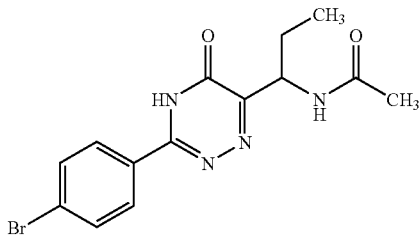

In analogy to the procedure for Example 10A, 10.2 g (43.3 mmol) 4-bromobenzenecarboximidamide hydrochloride and proportionate amounts of the other reagents are used.

Yield: 5.23 g (34%)

¹H-NMR (400 MHz, CD₃OD): δ=1.01 (t, 3H), 1.66–1.79 (m, 1H), 1.91–2.06 (m, 4H, s at 1.99), 5.02–5.09 (m, 1H), 7.75 (d, 2H), 7.93 (d, 2H) ppm.

EXAMPLE 17A

N-[1-(3-Cyclopropyl-5-oxo-4,5-dihydro-1,2,4-triazin-6-yl)propyl]acetamide

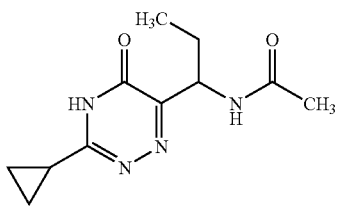

In analogy to the procedure for Example 10A, 7.30 g (60.5 mmol) cyclopropanecarboximidamide hydrochloride and proportionate amounts of the other reagents are used. The crude product is used in the next step without further purification.

Yield: 4.9 g (34%) crude product.

EXAMPLE 18A

N-[1-(3-Cyclopentyl-5-oxo-4,5-dihydro-1,2,4-triazin-6-yl)propyl]acetamide

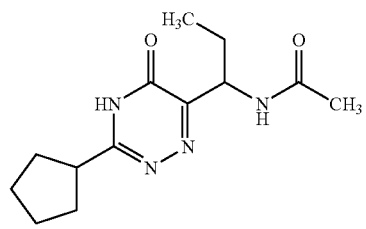

In analogy to the procedure for Example 10A, 3.50 g (23.6 mmol) cyclopentanecarboximidamide hydrochloride and proportionate amounts of the other reagents are used.

Yield: 1.7 g (27%)

LC/MS (method A): retention time 1.60 min., m/z 265 [M+H]⁺

EXAMPLE 19A

N-[1-(3-tert-Butyl-5-oxo-4,5-dihydro-1,2,4-triazin-6-yl)propyl]acetamide

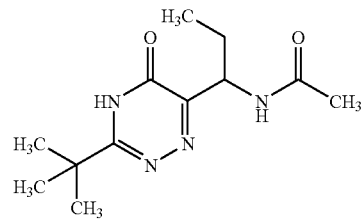

In analogy to the procedure for Example 10A, 6.0 g (11.0 mmol) 2,2-dimethylpropanimidamide hydrochloride and proportionate amounts of the other reagents are used.

Yield: 1.77 g (64%)

LC/MS (method A): retention time 1.59 min., m/z 253 [M+H]⁺

EXAMPLE 20A

N-{1-[3-(3-Nitrophenyl)-5-oxo-4,5-dihydro-1,2,4-triazin-6-yl]propyl}acetamide

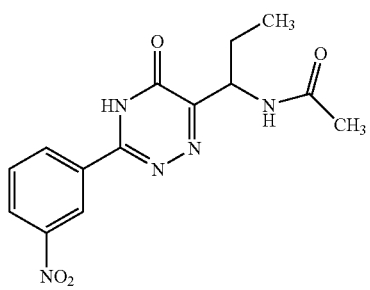

In analogy to the procedure for Example 10A, 35.0 g (174 mmol) 3-nitrobenzenecarboximidamide hydrochloride and proportionate amounts of the other reagents are used.

Yield: 13.6 g (25%)

¹H-NMR (200 MHz, CDCl₃): δ=0.97 (t, 3H), 1.83–2.08 (m, 5H, s at 2.02), 5.09 (m, 1H), 7.76 (t, 1H), 8.45 (d, 1H), 8.58 (d, 1H), 9.12 (s, 1H) ppm.

EXAMPLE 21A

N-[1-(5-Oxo-3-phenyl-4,5-dihydro-1,2,4-triazin-6-yl)propyl]acetamide

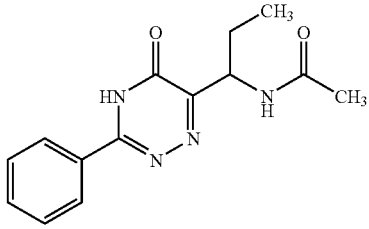

In analogy to the procedure for Example 10A, 7.26 g (46.8 mmol) benzenecarboximidamide hydrochloride and proportionate amounts of the other reagents are used.

Yield: 10.1 g (80%)

$^1$H-NMR (DMSO-$d_6$, 300 MHz): δ=0.9 (t, 3H), 1.5 (m, 1H), 1.8 (m, 1H), 1.9 (s, 3H), 4.9 (m, 1H), 7.5 (m, 3H), 8.1 (m, 3H), 14.1 (br. s, 1H) ppm.

EXAMPLE 22A

N-{(1-[3-(1-Naphthyl)-5-oxo-4,5-dihydro-1,2,4-triazin-6-yl]propyl}acetamide

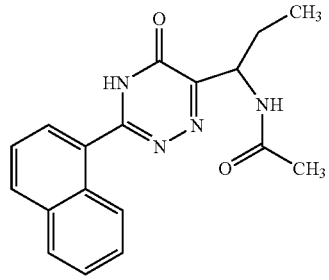

1.0 g (4.84 mmol, 1 equiv.) 1-naphthalenecarboximidamide hydrochloride are suspended in 2 ml of DMSO and 0.29 g (5.81 mmol, 1.2 equiv.) hydrazine hydrate are added. After stirring at room temperature for 16 hours, 1.45 g (7.3 mmol, 1.5 equiv) of the compound of Example 2A, dissolved in 10 ml of ethanol, are added. The reaction mixture is stirred at reflux for 1 hour and then at 60° C. (bath temperature) for 4 hours and then at room temperature over night. The mixture is evaporated to dryness in vacuo and the product is purified by flash chromatography.

Yield: 7.1 g (70%)

$^1$H-NMR (DMSO-$d_6$, 300 MHz): δ=1.0 (t, 3H), 1.6–1.7 (m, 2H), 1.9 (s, 3H), 5.0 (m, 1H), 7.5–8.2 (m, 8H), 14.0 (br. s, 1H) ppm.

EXAMPLE 23A 6-(1-Aminopropyl)-3-(3-bromophenyl)-1,2,4-triazin-5(4H)-one

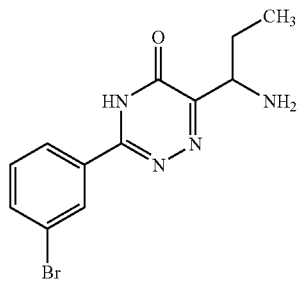

749 mg (2.13 mmol) Example 10A are heated to reflux in 20 ml 2 N hydrochloric acid for 18 hours. After cooling down to room temperature, the mixture is neutralized with 10% NaOH and, after addition of ethanol, evaporated to dryness in vacuo. The residue is treated with methanol and the filtrate separated from salts. The filtrate is evaporated to dryness in vacuo and the product purified by chromatography (flash or column chromatography or preparative HPLC).

Yield: 320 mg (49%)

$^1$H-NMR (DMSO-$d_6$, 200 MHz): δ=0.9 (t, 3H), 1.9 (m, 2H), 4.3 (d/d, 1H), 7.4 (m, 1H), 7.6 (m, 1H), 8.1 (br, s, 2H), 8.2 (m, 1H), 8.4 (m, 1H) ppm.

EXAMPLE 24A 6-(1-Aminopropyl)-3-(4-fluorophenyl)-1,2,4-triazin-5(4H)-one

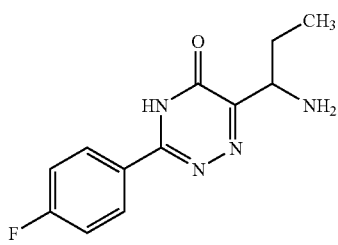

In analogy to the procedure for Example 23A, 1.46 g (5.0 mmol) of Example 11A and proportionate amounts of the other reagents are used.

Yield: 970 mg (78%)

LC/MS (A): MS (ESI): 249 (M+H$^+$), retention time 0.50 min

EXAMPLE 25A 6-(1-Aminopropyl)-3-(3-fluorophenyl)-1,2,4-triazin-5(4H)-one

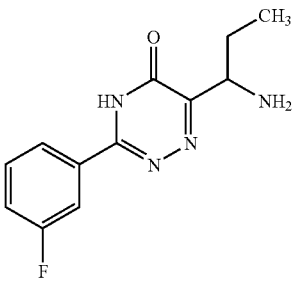

In analogy to the procedure for Example 23A, 1.1 g (3.8 mmol) of Example 12A and proportionate amounts of the other reagents are used.

Yield: 594 mg (63%)

LC/MS (A): MS (ESI): 249 (M+H$^+$), retention time 0.49 min

EXAMPLE 26A 6-(1-Aminopropyl)-3-(3-chlorophenyl)-1,2,4-triazin-5(4H)-one

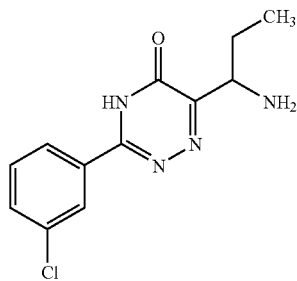

In analogy to the procedure for Example 23A, 419 mg (1.4 mmol) of Example 13A and proportionate amounts of the other reagents are used.

Yield: 280 mg (77%)

$^1$H-NMR (DMSO-$d_6$, 300 MHz): δ=0.9 (t, 3H), 1.9 (m, 1H), 2.0 (m, 1H), 4.3 (d/d, 1H), 7.5 (m, 2H), 8.2 (br. m, 4H) ppm.

EXAMPLE 27A 6-(1-Aminopropyl)-3-(2-bromophenyl)-1,2,4-triazin-5(4H)-one

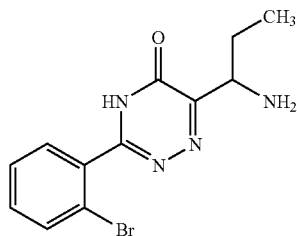

In analogy to the procedure for Example 23A, 1.00 g (2.85 mmol) of Example 14A and proportionate amounts of the other reagents are used.

Yield: 152 mg (17%)

$^1$H-NMR (DMSO-$d_6$, 300 MHz): δ=0.9 (t, 3H), 1.9 (m, 1H), 2.0 (m, 1H), 4.3 (d/d, 1H), 7.3 (m, 1H), 7.4 (m, 1H), 7.5 (m, 1H), 7.7 (m, 1H) ppm.

EXAMPLE 28A 6-(1-Aminopropyl)-3-cyclohexyl-1,2,4-triazin-5(4H)-one

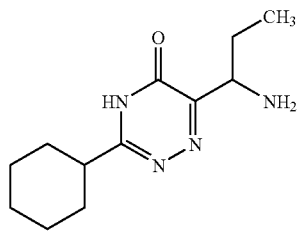

In analogy to the procedure for Example 23A, 1.14 g (4.10 mmol) of Example 15A and proportionate amounts of the other reagents are used.

Yield: 128 mg (13%)

$^1$H-NMR (DMSO-$d_6$, 300 MHz): δ=0.9 (t, 3H), 1.3 (m, 3H), 1.5 (m, 2H), 1.7 (m, 1H), 1.8 (m, 4H), 2.6 (m, 1H), 4.3 (m, 1H) ppm.

EXAMPLE 29A 6-(1-Aminopropyl)-3-(4-bromophenyl)-1,2,4-triazin-5(4H)-one

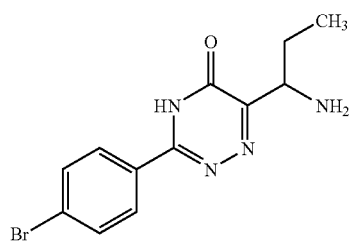

In analogy to the procedure for Example 23A, 5.0 g (14.2 mmol) N-{1-[3-(4-bromophenyl)-5-oxo-4,5-dihydro-1,2,4-triazin-6-yl]propyl}acetamide and proportionate amounts of the other reagents are used.

Yield: 3.4 g (77%)

$^1$H-NMR (300 MHz, CD$_3$OD): δ=1.02 (t, 3H), 1.87–2.22 (m, 5H, s at 1.96), 4.42–4.53 (t, 1H), 7.63 (d, 2H), 8.09 (d, 2H) ppm.

EXAMPLE 30A 6-(1-Aminopropyl)-3-cyclopropyl-1,2,4-triazin-5(4H)-one

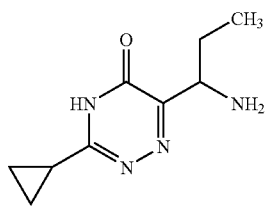

In analogy to the procedure for Example 23A, 4.90 g (20.7 mmol) N-[1-(3-cyclopropyl-5-oxo-4,5-dihydro-1,2,4-triazin-6-yl)propyl]acetamide and proportionate amounts of the other reagents are used.

Yield: 1.6 g (40%)

LC/MS (method A): retention time 0.362 min., m/z 195 [M+H]⁺

EXAMPLE 31A 6-(1-Aminopropyl)-3-tert-butyl-1,2,4-triazin-5(4H)-one

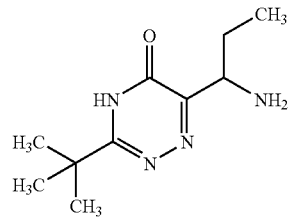

In analogy to the procedure for Example 23A, 1.77 g (4.42 mmol) N-[1-(3-tert-butyl-5-oxo-4,5-dihydro-1,2,4-triazin-6-yl)propyl]acetamide and proportionate amounts of the other reagents are used.

Yield: 850 mg (91%)

$^1$H-NMR (400 MHz, CD$_3$OD): δ=0.99 (t, 3H), 1.34 (s, 9H), 1.82–2.12 (m, 2H), 4.34 (t, 1H) ppm.

EXAMPLE 32A 6-(1-Aminopropyl)-3-cyclopentyl-1,2,4-triazin-5(4H)-one

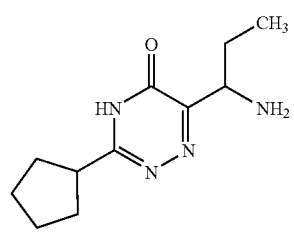

In analogy to the procedure for Example 23A, 1.65 g (6.24 mmol) N-[1-(3-cyclopentyl-5-oxo-4,5-dihydro-1,2,4-triazin-6-yl)propyl]acetamide and proportionate amounts of the other reagents are used.

Yield: 900 mg (65%)

$^1$H-NMR (300 MHz, CD$_3$OD): δ=0.99 (t, 3H), 1.64–2.11 (m, 10H), 3.03 (quin., 1H), 4.30 (t, 1H) ppm.

EXAMPLE 33A 6-(1-Aminopropyl)-3-(3-nitrophenyl)-1,2,4-triazin-5(4H)-one

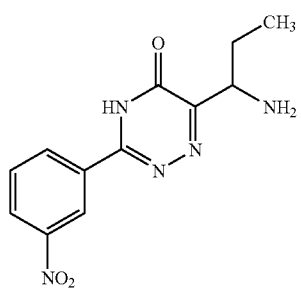

In analogy to the procedure for Example 23A, 13.5 g (42.5 mmol) N-{1-[3-(3-nitrophenyl)-5-oxo-4,5-dihydro-1,2,4-triazin-6-yl]propyl}acetamide and proportionate amounts of the other reagents are used.

Yield: 6.2 g (41%)

LC/MS (method A): retention time 0.497 min., m/z 276 [M+H]⁺

EXAMPLE 34A 6-(1-Aminopropyl)-3-phenyl-1,2,4-triazin-5(4H)-one

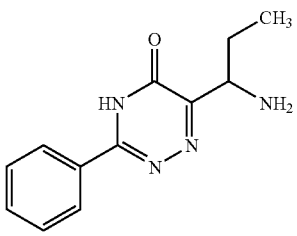

In analogy to the procedure for Example 23A, 10.00 g (36.7 mmol) of Example 21A and proportionate amounts of the other reagents are used.

Yield: 6.7 g (77%)

$^1$H-NMR (DMSO-d$_6$, 200 MHz): δ=0.9 (t, 3H), 1.9 (m, 2H), 4.1 (m, 1H), 4.3 (dd, 1H), 7.4 (m, 3H), 8.2 (m., 2H), 8.3 (bs, 2H) ppm.

EXAMPLE 35A 6-(1-Aminopropyl)-3-(1-naphthyl)-1,2,4-triazin-5(4H)-one

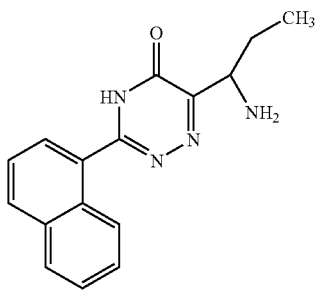

In analogy to the procedure for Example 23A, 700 mg (2.17 mmol) of Example 22A and proportionate amounts of the other reagents are used.

Yield: 557 mg (91%)

$^1$H-NMR (DMSO-d$_6$, 300 MHz): δ=0.9 (t, 3H), 1.8–2.2 (m, 2H), 4.4 (d/d, 1H), 7.4–8.7 (m, 10H) ppm.

EXAMPLE 36A

N-{1-[3-(3-Bromophenyl)-5-oxo-4,5-dihydro-1,2,4-triazin-6-yl]propyl}cyclopentanecarboxamide

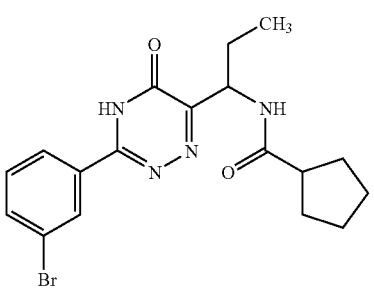

133 mg (0.43 mmol, 1 equiv.) Example 23A are suspended in 10 ml dichloromethane, 0.12 ml (0.86 mmol, 2 equiv.) triethylamine and 0.05 ml (0.43 mmol, 1 equiv.) cyclopentanecarbonyl chloride are added. The reaction mixture is stirred at room temperature until completion of reaction (1–2 hours). The reaction mixture is added to the same volume of 1N hydrochloric acid, the organic phase is washed with 1N hydrochloric acid and brine, dried over sodium sulfate and evaporated to dryness. The product is used without further purification or purified by chromatography (flash or column chromatography or preparative HPLC).

Yield: 97 mg (56%)

LC/MS (A): MS (ESI): 405, 407 (M+H$^+$), retention time 2.41 min.

EXAMPLE 37A

N-{1-[3-(4-Fluorophenyl)-5-oxo-4,5-dihydro-1,2,4-triazin-6-yl]propyl}cyclopentanecarboxamide

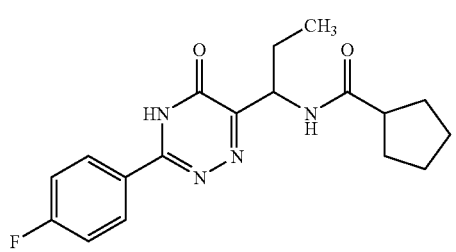

In analogy to the procedure for Example 36A, 464 mg (1.87 mmol) of Example 24A, 0.23 ml (1.87 mmol) cyclopentanecarbonyl chloride and proportionate amounts of the other reagents are used.

Yield: 365 mg (56%)

LC/MS (A): MS (ESI): 345 (M+H$^+$), retention time 2.22 min

EXAMPLE 38A

N-{1-[3-(4-Fluorophenyl)-5-oxo-4,5-dihydro-1,2,4-triazin-6-yl]propyl}cyclobutanecarboxamide

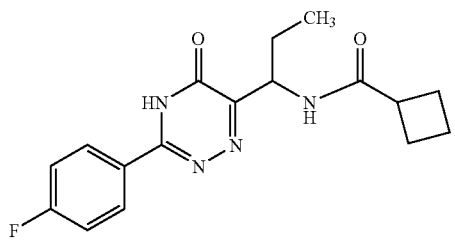

In analogy to the procedure for Example 36A, 475 mg (1.91 mmol) of Example 24A, 0.22 ml (1.91 mmol) cyclobutanecarbonyl chloride and proportionate amounts of the other reagents are used.

Yield: 142 mg (22%)

LC/MS (A): MS (ESI): 331 (M+H$^+$), retention time 2.09 min

EXAMPLE 39A

N-{1-[3-(3-Bromophenyl)-5-oxo-4,5-dihydro-1,2,4-triazin-6-yl]propyl}cyclobutanecarboxamide

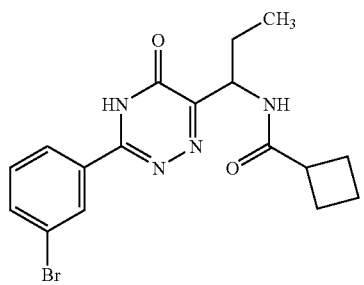

In analogy to the procedure for Example 36A, 135 mg (0.44 mmol) of Example 23A, 0.049 ml (0.44 mmol) cyclobutanecarbonyl chloride and proportionate amounts of the other reagents are used.

Yield: 110 mg (64%)

LC/MS (A): MS (ESI): 391, 393 (M+H$^+$), retention time 2.28 min

EXAMPLE 40A

N-{1-[3-(3-Fluorophenyl)-5-oxo-4,5-dihydro-1,2,4-triazin-6-yl]propyl}cyclobutanecarboxamide

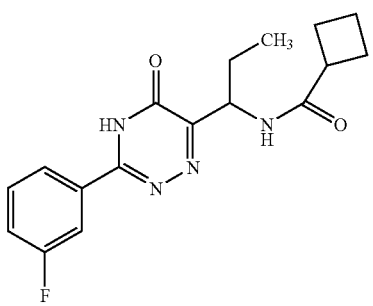

In analogy to the procedure for Example 36A, 326 mg (1.31 mmol) of Example 25A, 0.15 ml (1.31 mmol) cyclobutanecarbonyl chloride and proportionate amounts of the other reagents are used.

LC/MS (A): MS (ESI): 331 (M+H⁺), retention time 2.08 min

EXAMPLE 41A

N-{1-[3-(3-Fluorophenyl)-5-oxo-4,5-dihydro-1,2,4-triazin-6-yl]propyl}cyclopentanecarboxamide

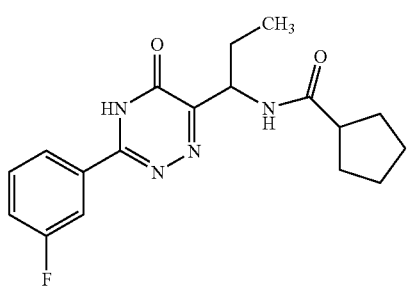

In analogy to the procedure for Example 36A, 326 mg (1.01 mmol) of Example 25A, 0.12 ml (1.01 mmol) cyclopentanecarbonyl chloride and proportionate amounts of the other reagents are used.

LC/MS (A): MS (ESI): 345 (M+H⁺), retention time 2.25 min.

EXAMPLE 42A

N-{1-[3-(3-Chlorophenyl)-5-oxo-4,5-dihydro-1,2,4-triazin-6-yl]propyl}cyclopentanecarboxamide

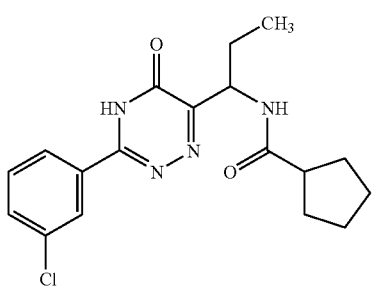

In analogy to the procedure for Example 36A, 158 mg (0.60 mmol) of Example 26A, 0.072 ml (0.60 mmol) cyclopentanecarbonyl chloride and proportionate amounts of the other reagents are used.

LC/MS (A): MS (ESI): 361 (M+H⁺), retention time 2.41 min.

EXAMPLE 43A

N-{1-[3-(3-Chlorophenyl)-5-oxo-4,5-dihydro-1,2,4-triazin-6-yl]propyl}cyclobutanecarboxamide

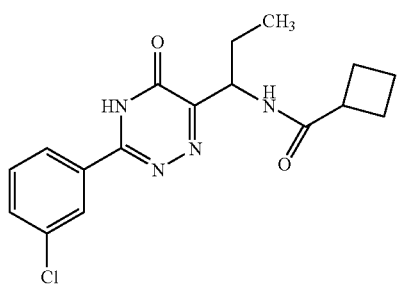

In analogy to the procedure for Example 36A, 100 mg (0.38 μmmol) of Example 26A, 0.043 ml (0.38 mmol) cyclobutanecarbonyl chloride and proportionate amounts of the other reagents are used.

LC/MS (A): MS (ESI): 347 (M+H⁺), retention time 2.27 min.

EXAMPLE 44A

N-{(1-[3-(3-Bromophenyl)-5-oxo-4,5-dihydro-1,2,4-triazin-6-yl]propyl}-3-methylbutanamide

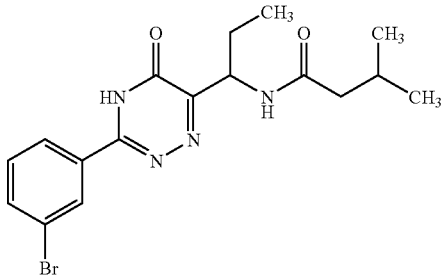

In analogy to the procedure for Example 36A, 500 mg (1.62 mmol) of Example 23A, 0.198 ml (1.62 mmol) 3-methylbutanoyl chloride and proportionate amounts of the other reagents are used.

LC/MS (A): MS (ESI): 393, 395 (M+H⁺), retention time 2.37 min.

EXAMPLE 45A

N-{1-[3-(2-Bromophenyl)-5-oxo-4,5-dihydro-1,2,4-triazin-6-yl]propyl}cyclopentanecarboxamide

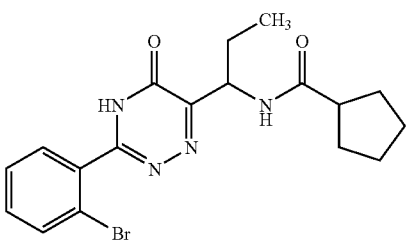

In analogy to the procedure for Example 36A, 143 mg (0.46 mmol) of Example 27A, 0.056 ml (0.46 mmol) cyclopentanecarbonyl chloride and proportionate amounts of the other reagents are used.

LC/MS (B): MS (ES+): 405, 407 (M+H$^+$), retention time 3.25 min.

EXAMPLE 46A

N-[1-(3-Cyclohexyl-5-oxo-4,5-dihydro-1,2,4-triazin-6-yl)propyl]cyclopentanecarboxamide

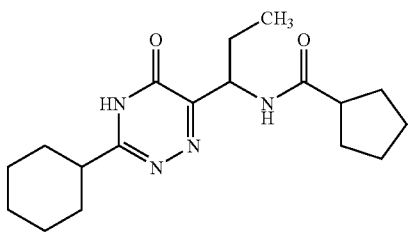

In analogy to the procedure for Example 36A, 120 mg (0.51 mmol) of Example 28A, 0.062 ml (0.51 mmol) cyclopentanecarbonyl chloride and proportionate amounts of the other reagents are used.

LC/MS (A): MS (ESI): 333 (M+H$^+$), retention time 2.29 min.

EXAMPLE 47A

N-{1-[3-(4-Bromophenyl)-5-oxo-4,5-dihydro-1,2,4-triazin-6-yl]propyl}cyclopentanecarboxamide

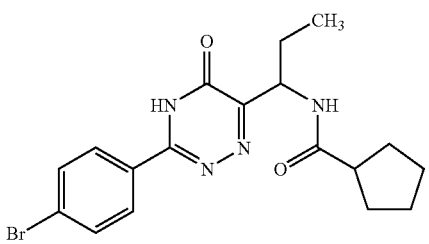

In analogy to the procedure for Example 36A, 3.35 g (10.8 mmol) 6-(1-aminopropyl)-3-(4-bromophenyl)-1,2,4-triazin-5(4H)-one, 2.16 g (16.3 mmol) cyclopentanecarbonyl chloride and proportionate amounts of the other reagents are used.

Yield: 2.35 g (54%)

$^1$H-NMR (300 MHz, CD3OD): δ=1.01 (t, 3H), 1.51–2.07 (m, 10H), 2.75 (quint, 1H), 5.00–5.10 (m, 1H), 7.75 (d, 2H), 7.93 (d, 2H)

EXAMPLE 48A

N-[1-(3-Cyclopropyl-5-oxo-4,5-dihydro-1,2,4-triazin-6-yl)propyl]cyclobutanecarboxamide

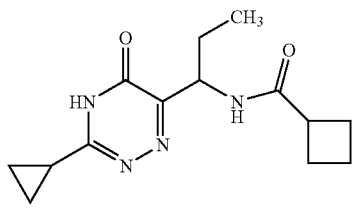

In analogy to the procedure for Example 36A, 250 mg (1.29 mmol) 6-(1-aminopropyl)-3-cyclopropyl-1,2,4-triazin-5(4H)-one, 150 mg (1.29 mmol) cyclobutanecarbonyl chloride and proportionate amounts of the other reagents are used. The crude product is used in the next step without further purification.

Yield: 350 mg crude product.

EXAMPLE 49A

N-[1-(3-Cyclopropyl-5-oxo-4,5-dihydro-1,2,4-triazin-6-yl)propyl]cyclopentanecarboxamide

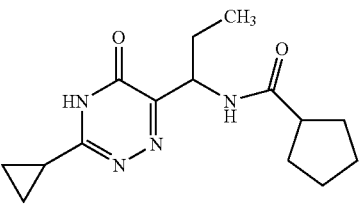

In analogy to the procedure for Example 36A, 250 mg (1.29 mmol) 6-(1-aminopropyl)-3-cyclopropyl-1,2,4-triazin-5(4H)-one, 170 mg (1.29 mmol) cyclopentanecarbonyl chloride and proportionate amounts of the other reagents are used. The crude product is used in the next step without further purification.

Yield: 370 mg crude product.

EXAMPLE 50A

N-[1-(3-Cyclopentyl-5-oxo-4,5-dihydro-1,2,4-triazin-6-yl)propyl]cyclobutanecarboxamide

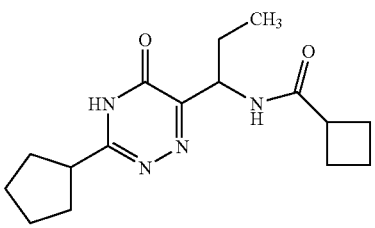

In analogy to the procedure for Example 36A, 200 mg (0.90 mmol) 6-(1-aminopropyl)-3-cyclopentyl-1,2,4-triazin- 5(4H)-one, 110 mg (0.90 mmol) cyclobutanecarbonyl chloride and proportionate amounts of the other reagents are used. The crude product is used in the next step without further purification.

Yield: 274 mg crude product.

EXAMPLE 51A

N-[1-(3-Cyclopentyl-5-oxo-4,5-dihydro-1,2,4-triazin-6-yl)propyl]cyclobutanecarboxamide

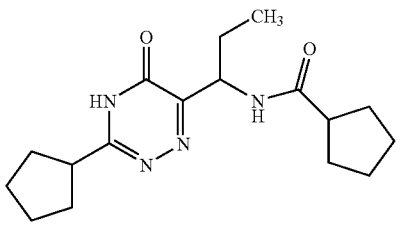

In analogy to the procedure for Example 36A, 200 mg (0.90 mmol) 6-(1-aminopropyl)-3-cyclopentyl-1,2,4-triazin-5(4H)-one, 120 mg (0.90 mmol) cyclopentanecarbonyl chloride and proportionate amounts of the other reagents are used. The crude product is used in the next step without further purification.

Yield: 290 mg crude product.

EXAMPLE 52A

N-[1-(3-tert-Butyl-5-oxo-4,5-dihydro-1,2,4-triazin-6-yl)propyl]cyclopentanecarboxamide

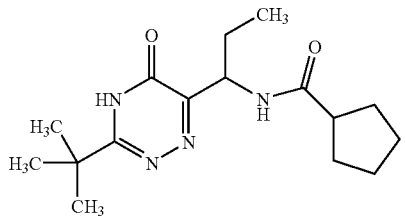

In analogy to the procedure for Example 36A, 110 mg (0.50 mmol) 6-(1-aminopropyl)-3-tert-butyl-1,2,4-triazin-5(4H)-one, 70 mg (0.50 mmol) cyclopentanecarbonyl chloride and proportionate amounts of the other reagents are used. The crude product is used in the next step without further purification.

Yield: 150 mg crude product.

EXAMPLE 53A

N-{1-[3-(3-Nitrophenyl)-5-oxo-4,5-dihydro-1,2,4-triazin-6-yl]propyl}cyclopentanecarboxamide

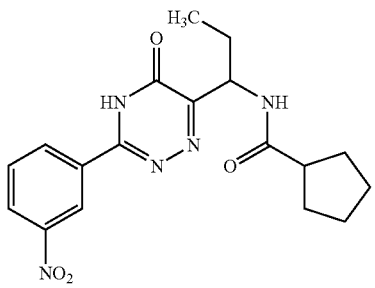

In analogy to the procedure for Example 36A, 3.0 g (10.9 mmol) 6-(1-aminopropyl)-3-(3-nitrophenyl)-1,2,4-triazin-5(4H)-one, 2.2 g (16.3 mmol) cyclopentanecarbonyl chloride and proportionate amounts of the other reagents are used.

Yield: 3.9 g (93%)

$^1$H-NMR (200 MHz, CDCl$_3$): δ=0.91 (t, 3H), 1.54–2.09 (m, 10H), 2.71 (quint, 1H), 5.25 (m, 1H), 7.74 (t, 1H), 8.48 (d, 1H), 8.64 (d, 1H), 9.25 (s, 1H) ppm.

EXAMPLE 54A

N-[1-(5-Oxo-3-phenyl-4,5-dihydro-1,2,4-triazin-6-yl)propyl]cyclopentanecarboxamide

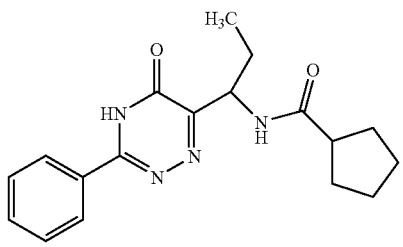

3.5 g (22.3 mmol, 1 equiv.) benzenecarboximidamide hydrochloride are suspended in 10 ml of ethanol and 1.37 g (26.8 mmol, 1.2 equiv.) hydrazine hydrate are added. After stirring at room temperature for 1 hour, 6.28 g (24.6 mmol, 1.1 equiv) of ethyl 3-[(cyclopentylcarbonyl)amino]-2-oxopentanoate (Example 99A), dissolved in 40 ml of ethanol, are added. The reaction mixture is stirred at 70° C. (bath temperature) for 4 hours. The mixture is evaporated to dryness in vacuo and the product is purified by chromatography (flash or column chromatography or preparative HPLC).

Yield: 658 mg (9%)

$^1$H-NMR (DMSO-d$_6$, 300 MHz): δ=0.9 (t, 3H), 1.4–1.9 (m, 10H), 2.7 (m, 1H), 4.9 (m, 1H), 7.6 (m, 3H), 8.0 (m, 3H), 14.1 (br. s, 1H) ppm.

EXAMPLE 55A

2-Methyl-N-[1-(5-oxo-3-phenyl-4,5-dihydro-1,2,4-triazin-6-yl)propyl]cyclopropanecarboxamide

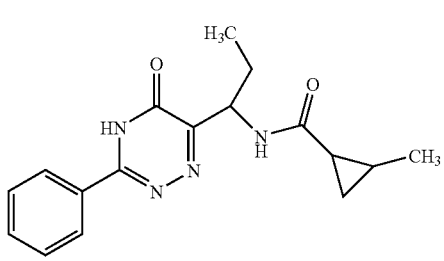

In analogy to the procedure for Example 36A, 100 mg (0.43 mmol) of Example 34A, 57 mg (0.48 mmol) 2-methylcyclopropanecarbonyl chloride and proportionate amounts of the other reagents are used.

Yield: 37 mg (28%)

LC/MS (A): MS (ESI): 313 (M+H$^+$), retention time 2.86 min

EXAMPLE 56A

N-[1-(5-Oxo-3-phenyl-4,5-dihydro-1,2,4-triazin-6-yl)propyl]cyclobutanecarboxamide

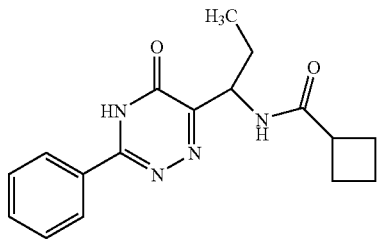

In analogy to the procedure for Example 36A, 100 mg (0.43 mmol) of Example 34A, 57 mg (0.48 mmol) cyclobutanecarbonyl chloride and proportionate amounts of the other reagents are used.

Yield: 160 mg (96%)

LC/MS (A): MS (ESI): 313 (M+H$^+$), retention time 2.83 min.

EXAMPLE 57A

N-[1-(5-Oxo-3-phenyl-4,5-dihydro-1,2,4-triazin-6-yl)propyl]tetrahydro-3-furancarboxamide

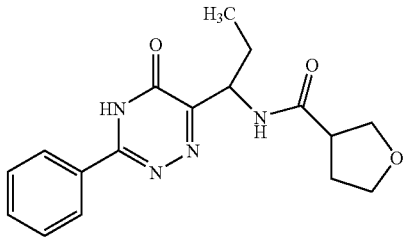

In analogy to the procedure for Example 36A, 100 mg (0.43 mmol) of Example 34A, 64 mg (0.48 mmol) 3-tetrahydrofuranecarbonyl chloride and proportionate amounts of the other reagents are used.

Yield: 150 mg (84%)

LC/MS (A): MS (ESI): 329 (M+H$^+$), retention time 2.26 min.

EXAMPLE 58A

N-[1-(5-Oxo-3-phenyl-4,5-dihydro-1,2,4-triazin-6-yl)propyl]tetrahydro-2-furancarboxamide

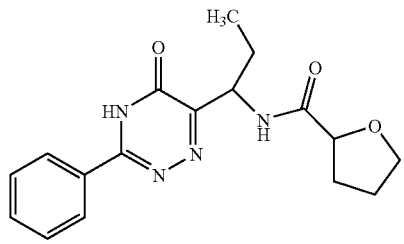

50 mg (0.43 mmol, 1 equiv.) 2-tetrahydrofurancarboxylic acid are suspended in dichloromethane at 0° C. and 62 mg (0.456 mmol, 1.05 equiv.) 1-hydroxy-1H-benzotriazol and 87 mg (0.456 mmol, 1.05 equiv.) 1-(3-dimethylaminopropyl)-3-ethylcarbodiimide hydrochloride are consecutively added. After stirring at room temperature for 30 min, 100 mg (0.43 mmol) of Example 34A are added. The reaction mixture is stirred at room temperature for 2 hours. The mixture is diluted with dichloromethane, washed twice with 1N sulfuric acid and once with saturated sodium bicarbonate solution, dried over magnesium sulfate and evaporated to dryness in vacuo. The product is used without further purification.

Yield: 82 mg (57%)

LC/MS (A): MS (ESI): 329 (M+H$^+$), retention time 2.7 min.

EXAMPLE 59A

N-[1-(5-Oxo-3-phenyl-4,5-dihydro-1,2,4-triazin-6-yl)propyl]cyclopropanecarboxamide

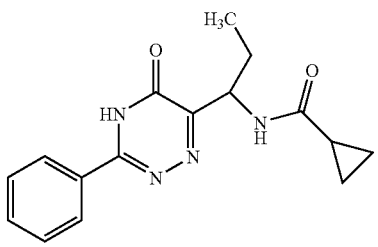

In analogy to the procedure for Example 36A, 100 mg (0.43 mmol) of Example 34A, 57 mg (0.48 mmol) cyclopropanecarbonyl chloride and proportionate amounts of the other reagents are used.

Yield: 130 mg (100%)

LC/MS (A): MS (ESI): 299 (M+H$^+$), retention time 2.61 min.

EXAMPLE 60A

N-[1-(5-Oxo-3-phenyl-4,5-dihydro-1,2,4-triazin-6-yl)propyl]tetrahydro-2H-pyran-4-carboxamide

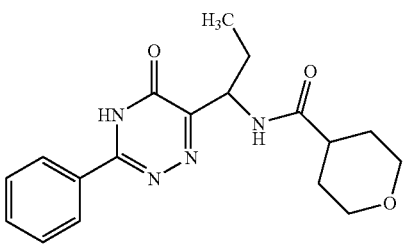

In analogy to the procedure for Example 36A, 100 mg (0.43 mmol) of Example 34A, 71 mg (0.48 mmol) tetrahydro-2H-pyran-4-carbonyl chloride and proportionate amounts of the other reagents are used.

Yield: 250 mg crude product

LC/MS (A): MS (ESI): 343 (M+H$^+$), retention time 2.59 min.

EXAMPLE 61A

N-[1-(5-Oxo-3-phenyl-4,5-dihydro-1,2,4-triazin-6-yl)propyl]cyclohexanecarboxamide

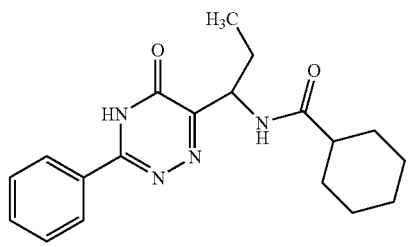

In analogy to the procedure for Example 36A, 100 mg (0.43 mmol) of Example 34A, 70 mg (0.48 mmol) cyclohexanecarbonyl chloride and proportionate amounts of the other reagents are used.

Yield: 250 mg crude product

LC/MS (A): MS (ESI): 341 (M+H$^+$), retention time 3.43 min.

EXAMPLE 62A

4-Methoxy-N-[1-(5-oxo-3-phenyl-4,5-dihydro-1,2,4-triazin-6-yl)propyl]cyclohexanecarboxamide

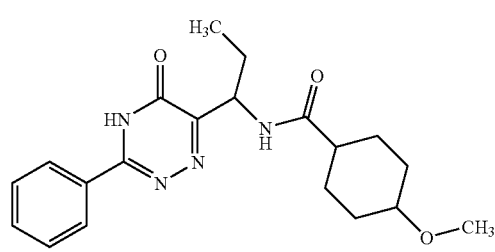

In analogy to the procedure for Example 36A, 100 mg (0.43 mmol) of Example 34A, 80 mg (0.48 mmol) 4-methoxycyclohexanecarbonyl chloride and proportionate amounts of the other reagents are used.

Yield: 150 mg (93%)

LC/MS (A): MS (ESI): 371 (M+H$^+$), retention time 2.78 min.

EXAMPLE 63A

N-[1-(5-Oxo-3-phenyl-4,5-dihydro-1,2,4-triazin-6-yl)propyl]bicyclo[2.2.1]hept-5-ene-2-carboxamide

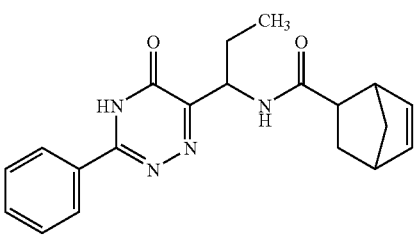

In analogy to the procedure for Example 36A, 100 mg (0.43 mmol) of Example 34A, 70 mg (0.48 mmol) bicyclo[2.2.1]hept-5-ene-2-carbonyl chloride and proportionate amounts of the other reagents are used.

Yield: 150 mg (98%)

LC/MS (A): MS (ESI): 351 (M+H$^+$), retention time 3.18 min.

EXAMPLE 64A

N-[1-(5-Oxo-3-phenyl-4,5-dihydro-1,2,4-triazin-6-yl)propyl]cycloheptanecarboxamide

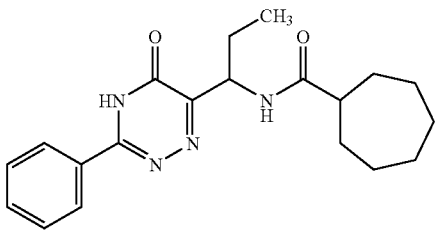

In analogy to the procedure for Example 36A, 100 mg (0.43 mmol) of Example 34A, 80 mg (0.48 mmol) cycloheptanecarbonyl chloride and proportionate amounts of the other reagents are used.

Yield: 150 mg (97%)

LC/MS (A): MS (ESI): 355 (M+H$^+$), retention time 3.47 min.

EXAMPLE 65A 2,2-Dimethyl-N-[1-(5-oxo-3-phenyl-4,5-dihydro-1,2,4-triazin-6-yl)propyl]propanamide

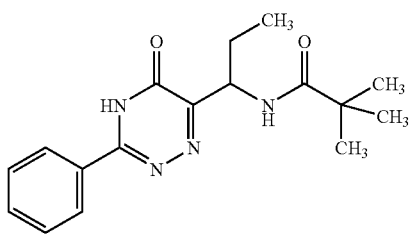

In analogy to the procedure for Example 36A, 100 mg (0.43 mmol) of Example 34A, 60 mg (0.48 mmol) 2,2-dimethylpropanoyl chloride and proportionate amounts of the other reagents are used.

Yield: 130 mg (95%)

LC/MS (A): MS (ESI): 315 (M+H$^+$), retention time 3.07 min.

EXAMPLE 66A

2-Methyl-N-[1-(5-oxo-3-phenyl-4,5-dihydro-1,2,4-triazin-6-yl)propyl]butanamide

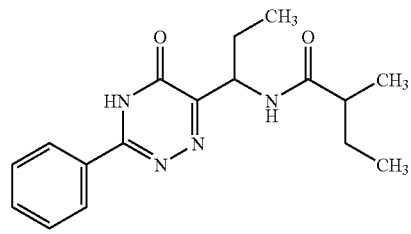

In analogy to the procedure for Example 36A, 100 mg (0.43 mmol) of Example 34A, 60 mg (0.48 mmol) 2-methylbutanoyl chloride and proportionate amounts of the other reagents are used.

Yield: 130 mg (95%)

LC/MS (A): MS (ESI): 315 (M+H$^+$), retention time 2.90 min.

EXAMPLE 67A

2-Ethyl-N-[1-(5-oxo-3-phenyl-4,5-dihydro-1,2,4-triazin-6-yl)propyl]butanamide

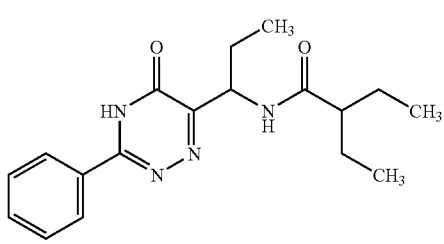

In analogy to the procedure for Example 36A, 100 mg (0.43 mmol) of Example 34A, 60 mg (0.48 mmol) 2-ethylbutanoyl chloride and proportionate amounts of the other reagents are used.

Yield: 130 mg (91%)

LC/MS (A): MS (ESI): 329 (M+H$^+$), retention time 3.09 min.

EXAMPLE 68A 2,2-Dimethyl-N-[1-(5-oxo-3-phenyl-4,5-dihydro-1,2,4-triazin-6-yl)propyl]butanamide

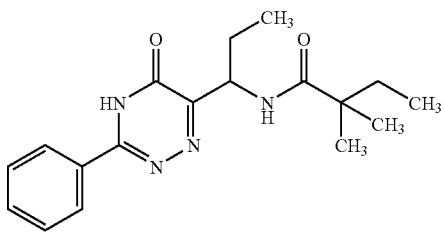

In analogy to the procedure for Example 58A, 100 mg (0.43 mmol) of Example 34A, 50 mg (0.43 mmol) 2,2-dimethylbutyric acid and proportionate amounts of the other reagents are used.

Yield: 130 mg (91%)

LC/MS (A): MS (ESI): 329 (M+H$^+$), retention time 3.27 min.

EXAMPLE 69A

2-Oxo-N-[1-(5-oxo-3-phenyl-4,5-dihydro-1,2,4-triazin-6-yl)propyl]bicyclo[2.2.1]heptane-7-carboxamide

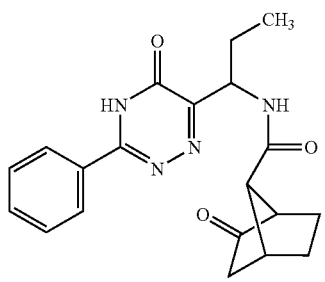

In analogy to the procedure for Example 58A, 100 mg (0.43 mmol) of Example 34A, 70 mg (0.43 mmol) 2-oxo-bicyclo[2.2.1]heptane-7-carboxylic acid and proportionate amounts of the other reagents are used.

Yield: 150 mg (94%)

LC/MS (A): MS (ESI): 367 (M+H$^+$), retention time 2.69 min.

EXAMPLE 70A 3,3,3-Trifluoro-N-[1-(5-oxo-3-phenyl-4,5-dihydro-1,2,4-triazin-6-yl)propyl]propanamide

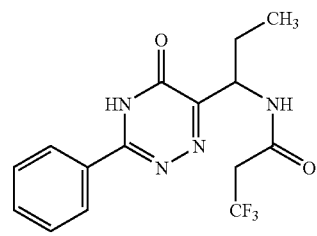

In analogy to the procedure for Example 36A, 100 mg (0.43 mmol) of Example 34A, 70 mg (0.48 mmol) 3,3,3-trifluoromethylpropanoyl chloride and proportionate amounts of the other reagents are used.

Yield: 150 mg crude product

LC/MS (A): MS (ESI): 341 (M+H⁺), retention time 2.84 min.

EXAMPLE 71A

1-Methyl-N-[1-(5-oxo-3-phenyl-4,5-dihydro-1,2,4-triazin-6-yl)propyl]cyclohexanecarboxamide

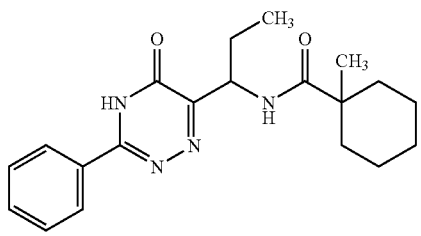

In analogy to the procedure for Example 36A, 100 mg (0.43 mmol) of Example 34A, 80 mg (0.48 mmol) 1-methylcyclohexanecarbonyl chloride and proportionate amounts of the other reagents are used.

Yield: 150 mg (97%)

LC/MS (A): MS (ESI): 355 (M+H⁺), retention time 3.56 min.

EXAMPLE 72A

3-Fluoro-2,2-dimethyl-N-[1-(5-oxo-3-phenyl-4,5-dihydro-1,2,4-triazin-6-yl)propyl]propanamide

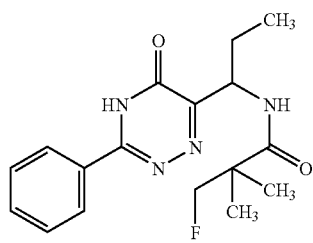

In analogy to the procedure for Example 36A, 100 mg (0.43 mmol) of Example 34A, 80 mg (0.48 mmol) 3-fluoro-2,2-dimethylpropanoyl chloride and proportionate amounts of the other reagents are used.

Yield: 150 mg crude product

LC/MS (A): MS (ESI): 333 (M+H⁺), retention time 3.01 min.

EXAMPLE 73A

2-Bicyclo[2.2.1]hept-2-yl-N-[1-(5-oxo-3-phenyl-4,5-dihydro-1,2,4-triazin-6-yl)propyl]acetamide

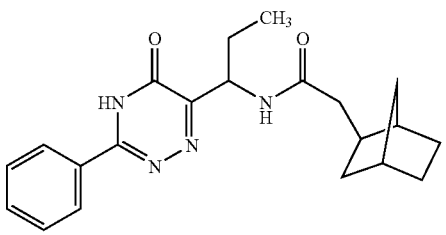

In analogy to the procedure for Example 36A, 100 mg (0.43 mmol) of Example 34A, 80 mg (0.48 mmol) bicyclo[2.2.1]hept-2-ylacetyl chloride and proportionate amounts of the other reagents are used.

Yield: 150 mg (94%)

LC/MS (A): MS (ESI): 367 (M+HF), retention time 3.53 min.

EXAMPLE 74A

3-Methyl-N-[1-(5-oxo-3-phenyl-4,5-dihydro-1,2,4-triazin-6-yl)propyl]butanamide

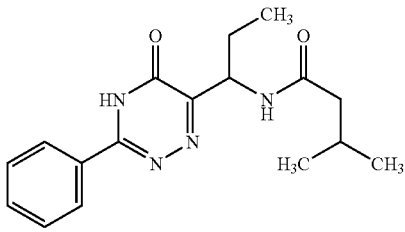

In analogy to the procedure for Example 36A, 100 mg (0.43 mmol) of Example 34A, 60 mg (0.48 mmol) 3-methylbutanoyl chloride and proportionate amounts of the other reagents are used.

Yield: 140 mg crude product

LC/MS (A): MS (ESI): 315 (M+H⁺), retention time 2.92 min.

EXAMPLE 75A

N-[1-(5-Oxo-3-phenyl-4,5-dihydro-1,2,4-triazin-6-yl)propyl]-4-(trifluoromethyl)cyclohexanecarboxamide

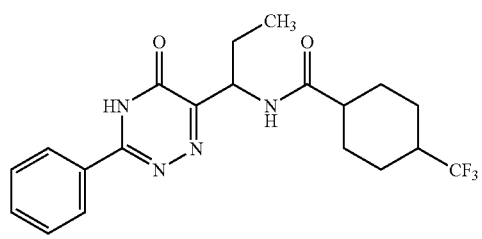

In analogy to the procedure for Example 36A, 100 mg (0.43 mmol) of Example 34A, 90 mg (0.48 mmol) 4-trifluoromethylcyclohexanecarbonyl chloride and proportionate amounts of the other reagents are used. A mixture of isomers is obtained.

Yield: 170 mg (96%)

LC/MS (A): MS (ESI): 409 (M+H$^+$), retention time 3.54 min.

EXAMPLE 76A

N-[1-(5-Oxo-3-phenyl-4,5-dihydro-1,2,4-triazin-6-yl)propyl]-3-(tdfluoromethyl)cyclohexanecarboxamide

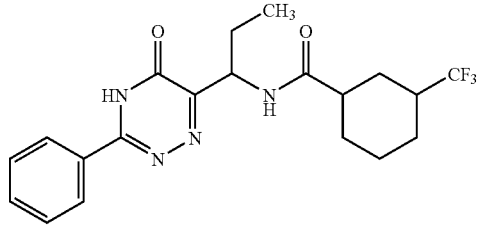

In analogy to the procedure for Example 36A, 100 mg (0.43 mmol) of Example 34A, 90 mg (0.48 mmol) 3-trifluoromethylcyclohexanecarbonyl chloride and proportionate amounts of the other reagents are used. A mixture of isomers is obtained.

Yield: 170 mg (96%)

LC/MS (A): MS (ESI): 409 (M+H$^+$), retention time 3.58 min.

EXAMPLE 77A 1,4-Dimethyl-N-[1-(5-oxo-3-phenyl-4,5-dihydro-1,2,4-triazin-6-yl)propyl]cyclohexanecarboxamide

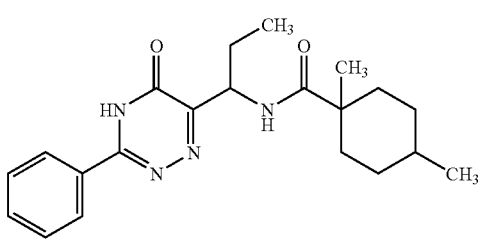

In analogy to the procedure for Example 36A, 100 mg (0.43 mmol) of Example 34A, 80 mg (0.48 mmol) 1,4-dimethylcyclohexanecarbonyl chloride and proportionate amounts of the other reagents are used. A mixture of isomers is obtained.

Yield: 160 mg (96%)

LC/MS (A): MS (ESI): 369 (M+H$^+$), retention time 3.81 and 3.85 min.

EXAMPLE 78A

4-Methyl-N-[1-(5-oxo-3-phenyl-4,5-dihydro-1,2,4-triazin-6-yl)propyl]cyclohexanecarboxamide

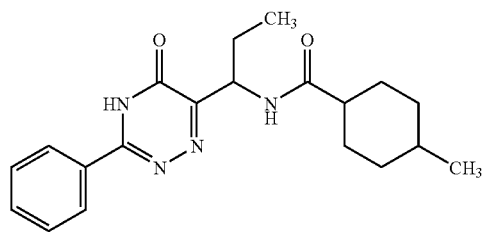

In analogy to the procedure for Example 58A, 100 mg (0.43 mmol) of Example 34A, 60 mg (0.48 mmol) 4-methylcyclohexanecarboxylic acid and proportionate amounts of the other reagents are used.

Yield: 150 mg (97%)

LC/MS (A): MS (ESI): 355 (M+H$^+$), retention time 3.54 min.

EXAMPLE 79A

2-Cyclohexyl-N-[1-(5-oxo-3-phenyl-4,5-dihydro-1,2,4-triazin-6-yl)propyl]acetamide

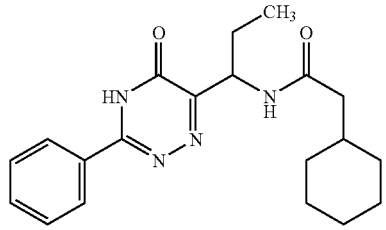

In analogy to the procedure for Example 58A, 100 mg (0.43 mmol) of Example 34A, 80 mg (0.48 mmol) 2-cyclohexylacetic acid and proportionate amounts of the other reagents are used.

Yield: 150 mg (97%)

LC/MS (A): MS (ESI): 355 (M+H$^+$), retention time 3.48 min.

EXAMPLE 80A

N-[1-(5-Oxo-3-phenyl-4,5-dihydro-1,2,4-triazin-6-yl)propyl]propanamide

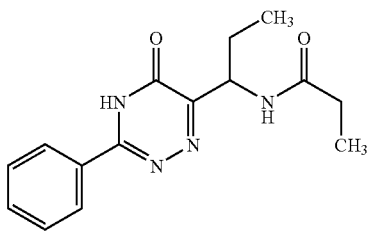

In analogy to the procedure for Example 36A, 100 mg (0.43 mmol) of Example 34A, 40 mg (0.48 mmol) propanoyl chloride and proportionate amounts of the other reagents are used.

Yield: 120 mg (96%)

LC/MS (A): MS (ESI): 287 (M+H$^+$), retention time 2.42 min.

EXAMPLE 81A

N-[1-(5-Oxo-3-phenyl-4,5-dihydro-1,2,4-triazin-6-yl)propyl]pentanamide

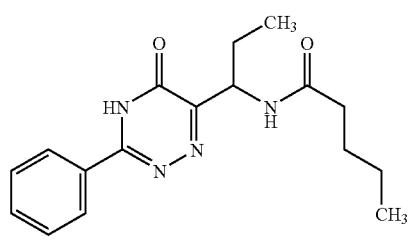

In analogy to the procedure for Example 36A, 100 mg (0.43 mmol) of Example 34A, 60 mg (0.48 mmol) pentanoyl chloride and proportionate amounts of the other reagents are used.

Yield: 130 mg (95%)

LC/MS (A): MS (ESI): 315 (M+H$^+$), retention time 3.02 min.

EXAMPLE 82A

N-[1-(5-Oxo-3-phenyl-4,5-dihydro-1,2,4-triazin-6-yl)propyl]hexanamide

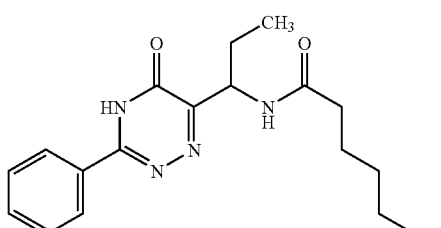

In analogy to the procedure for Example 36A, 100 mg (0.43 mmol) of Example 34A, 60 mg (0.48 mmol) hexanoyl chloride and proportionate amounts of the other reagents are used.

Yield: 140 mg (98%)

LC/MS (A): MS (ESI): 329 (M+H$^+$), retention time 3.30 min.

EXAMPLE 83A

N-[1-(5-Oxo-3-phenyl-4,5-dihydro-1,2,4-triazin-6-yl)propyl]octanamide

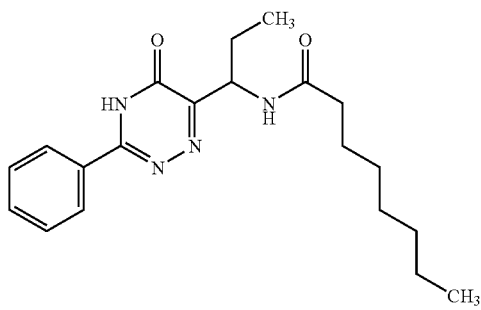

In analogy to the procedure for Example 36A, 100 mg (0.43 mmol) of Example 34A, 80 mg (0.48 mmol) octanoyl chloride and proportionate amounts of the other reagents are used.

Yield: 150 mg (97%)

LC/MS (A): MS (ES): 357 (M+H$^+$), retention time 3.82 min.

EXAMPLE 84A

N-[1-(5-Oxo-3-phenyl-4,5-dihydro-1,2,4-triazin-6-yl)propyl]heptanamide

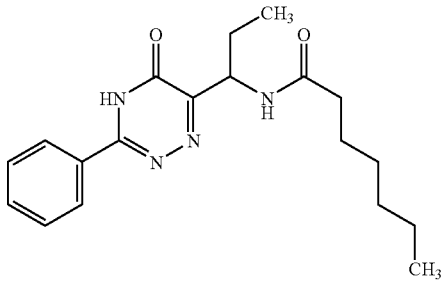

In analogy to the procedure for Example 36A, 100 mg (0.43 mmol) of Example 34A, 70 mg (0.48 mmol) heptanoyl chloride and proportionate amounts of the other reagents are used.

Yield: 140 mg (94%)

LC/MS (A): MS (ESI): 343 (M+H$^+$), retention time 3.56 min.

EXAMPLE 85A

2-Methyl-N-[1-(5-oxo-3-phenyl-4,5-dihydro-1,2,4-triazin-6-yl)propyl]propanamide

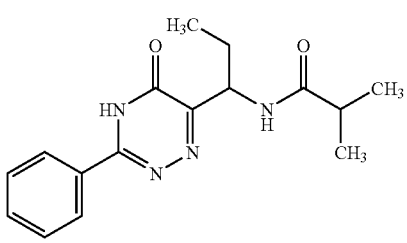

In analogy to the procedure for Example 36A, 100 mg (0.43 mmol) of Example 34A, 60 mg (0.48 mmol) 2-methylpropanoyl chloride and proportionate amounts of the other reagents are used.
Yield: 130 mg (99%)
LC/MS (A): MS (ESI): 301 (M+H$^+$), retention time 2.68 min.

EXAMPLE 86A 3,3-Dimethyl-N-[1-(5-oxo-3-phenyl-4,5-dihydro-1,2,4-triazin-6-yl)propyl]butanamide

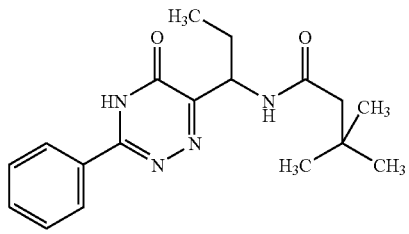

In analogy to the procedure for Example 36A, 100 mg (0.43 mmol) of Example 34A, 60 mg (0.48 mmol) 3,3-dimethylbutanoyl chloride and proportionate amounts of the other reagents are used.
Yield: 140 mg (98%)
LC/MS (A): MS (ESI): 329 (M+H$^+$), retention time 3.23 min.

EXAMPLE 87A

2-Methoxy-N-[1-(5-oxo-3-phenyl-4,5-dihydro-1,2,4-triazin-6-yl)propyl]acetamide

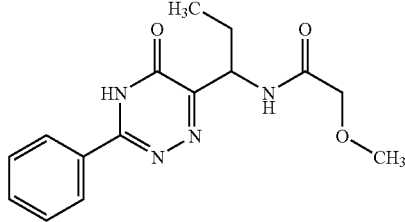

In analogy to the procedure for Example 36A, 100 mg (0.43 mmol) of Example 34A, 50 mg (0.48 mmol) 2-methoxyacetyl chloride and proportionate amounts of the other reagents are used.
Yield: 130 mg (99%)
LC/MS (A): MS (ESI): 303 (M+H$^+$), retention time 2.55 min.

EXAMPLE 88A

3-Methoxy-N-[1-(5-oxo-3-phenyl-4,5-dihydro-1,2,4-triazin-6-yl)propyl]cyclohexanecarboxamide

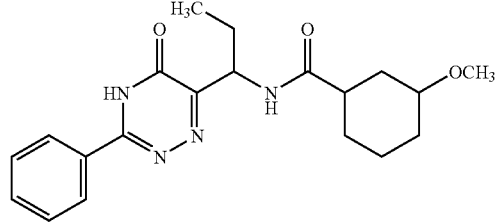

In analogy to the procedure for Example 36A, 100 mg (0.43 mmol) of Example 34A, 80 mg (0.48 mmol) 3-methoxycyclohexanecarbonyl chloride and proportionate amounts of the other reagents are used.

Yield: 160 mg (99%)

LC/MS (A): MS (ESI): 371 (M+H$^+$), retention time 3.02 min.

EXAMPLE 89A

2-Methyl-N-[1-(5-oxo-3-phenyl-4,5-dihydro-1,2,4-triazin-6-yl)propyl]pentanamide

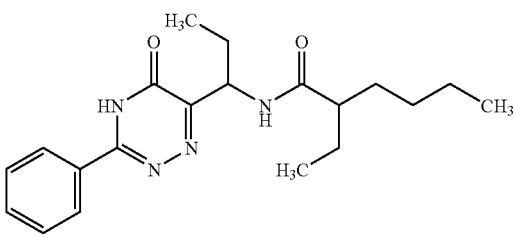

In analogy to the procedure for Example 36A, 100 mg (0.43 mmol) of Example 34A, 80 mg (0.48 mmol) 2-ethylhexanoyl chloride and proportionate amounts of the other reagents are used.

Yield: 140 mg (98%)

LC/MS (A): MS (ESI): 357 (M+H$^+$), retention time 3.64 min.

EXAMPLE 90A

2-Methyl-N-[1-(5-oxo-3-phenyl-4,5-dihydro-1,2,4-triazin-6-yl)propyl]pentanamide

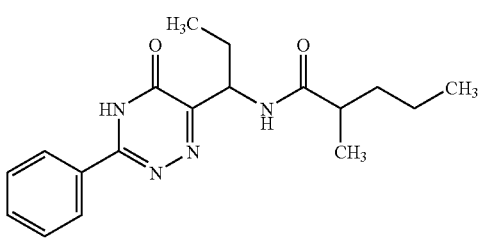

In analogy to the procedure for Example 36A, 100 mg (0.43 mmol) of Example 34A, 50 mg (0.48 mmol) 2-methylpentanoyl chloride and proportionate amounts of the other reagents are used.

Yield: 140 mg (98%)
LC/MS (A): MS (ESI): 329 (M+H⁺), retention time 3.26 min.

EXAMPLE 91A

3-Cyclopentyl-N-[1-(5-oxo-3-phenyl-4,5-dihydro-1,2,4-triazin-6-yl)propyl]propanamide

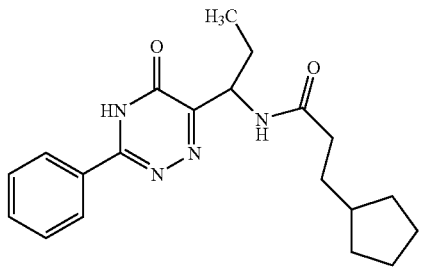

In analogy to the procedure for Example 36A, 100 mg (0.43 mmol) of Example 34A, 50 mg (0.48 mmol) 3-cyclopentylpropanoyl chloride and proportionate amounts of the other reagents are used.
Yield: 150 mg (97%)
LC/MS (A): MS (ESI): 355 (M+H⁺), retention time 3.61 min.

EXAMPLE 92A

N-[1-(5-Oxo-3-phenyl-4,5-dihydro-1,2,4-triazin-6-yl)propyl]butanamide

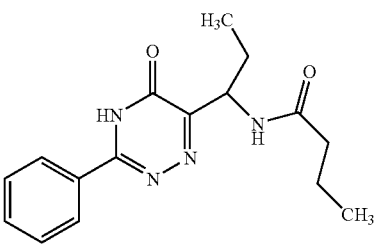

In analogy to the procedure for Example 36A, 100 mg (0.43 mmol) of Example 34A, 50 mg (0.48 mmol) butanoyl chloride and proportionate amounts of the other reagents are used.
Yield: 130 mg (99%)
LC/MS (A): MS (ESI): 301 (M+H⁺), retention time 2.73 min.

EXAMPLE 93A

4-Ethyl-N-[1-(5-oxo-3-phenyl-4,5-dihydro-1,2,4-triazin-6-yl)propyl]cyclohexanecarboxamide

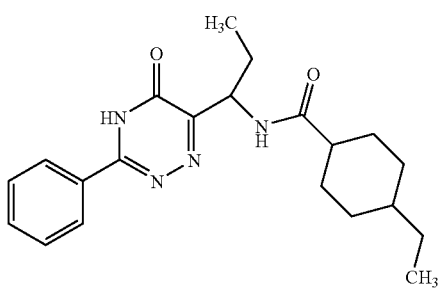

In analogy to the procedure for Example 58A, 100 mg (0.43 mmol) of Example 34A, 70 mg (0.43 mmol) 3,3,5-trimethylcyclohexanecarboxylic acid and proportionate amounts of the other reagents are used.
Yield: 150 mg (94%)
LC/MS (A): MS (ESI): 369 (M+H⁺), retention time 3.84 min.

EXAMPLE 94A 3,3,5-Trimethyl-N-[1-(5-oxo-3-phenyl-4,5-dihydro-1,2,4-triazin-6-yl)propyl]cyclohexanecarboxamide

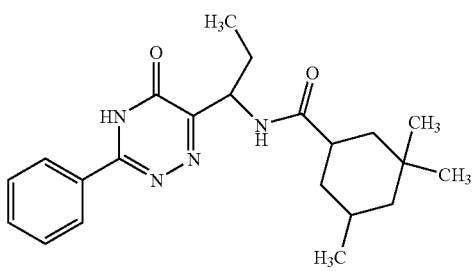

In analogy to the procedure for Example 58A, 100 mg (0.43 mmol) of Example 34A, 70 mg (0.43 mmol) 3,3,5-trimethylcyclohexanecarboxylic acid and proportionate amounts of the other reagents are used.
Yield: 150 mg (90%)
LC/MS (A): MS (ESI): 383 (M+H⁺), retention time 3.98 min.

EXAMPLE 95A 4,4-Dimethyl-N-[1-(5-oxo-3-phenyl-4,5-dihydro-1,2,4-triazin-6-yl)propyl]cyclohexanecarboxamide

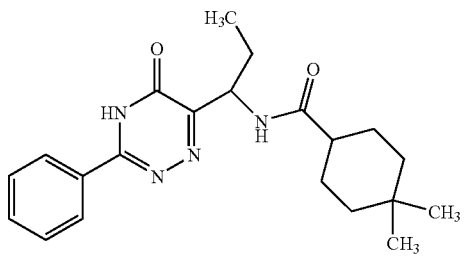

In analogy to the procedure for Example 58A, 100 mg (0.43 mmol) of Example 34A, 68 mg (0.43 mmol) 4,4-dimethylcyclohexanecarboxylic acid and proportionate amounts of the other reagents are used.

Yield: 150 mg (94%)
LC/MS (A): MS (ESI): 369 (M+H⁺), retention time 3.76 min.

EXAMPLE 96A

N-{1-[3-(1-Naphthyl)-5-oxo-4,5-dihydro-1,2,4-triazin-6-yl]propyl}cyclopentanecarboxamide

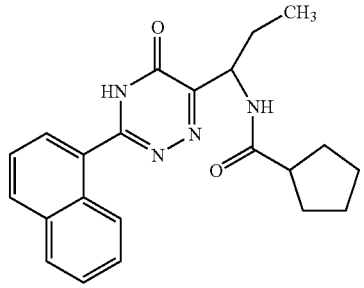

In analogy to the procedure for Example 36A, 550 mg (1.96 mmol) of Example 35A, 312 mg (2.35 mmol) cyclopentanecarbonyl chloride and proportionate amounts of the other reagents are used. The crude product is recrystallized from diethyl ether.

Yield: 610 mg (82%)
$^1$H-NMR (DMSO-$d_6$, 300 MHz): δ=1.0 (t, 3H), 1.4–2.0 (m, 10H), 2.7 (m, 1H), 5.0 (m, 1H), 7.6–8.3 (m, 8H), 14.1 (br. s, 1H) ppm.

EXAMPLE 97A

N-{1-[3-(1-Naphthyl)-5-oxo-4,5-dihydro-1,2,4-triazin-6-yl]propyl}cyclobutanecarboxamide

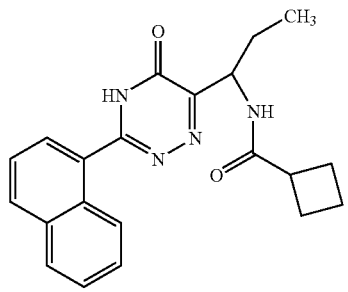

In analogy to the procedure for Example 36A, 230 mg (0.82 mmol) of Example 35A, 117 mg (0.98 mmol) cyclobutanecarbonyl chloride and proportionate amounts of the other reagents are used.

Yield: 210 mg (63%)
$^1$H-NMR (DMSO-$d_6$, 200 MHz): δ=0.9 (t, 3H), 1.5–2.3 (m, 8H), 3.1 (m, 1H), 5.0 (m, 1H), 7.6–8.3 (m, 8H), 14.1 (br. s, 1H) ppm.

EXAMPLE 98A

2-[(Cyclopentylcarbonyl)amino]butanoic acid

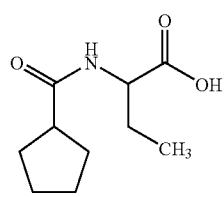

35 g (339 mmol) 2-aminobutanoic acid and 75.6 g (747 mmol) triethylamine are suspended in 300 ml of dichloromethane and stirred at 0° C. 81 g (747 mmol) chlorotrimethylsilane are added dropwise, then the mixture is stirred for 1 hour at room temperature and 1 hour at 40° C. After cooling down at −10° C., 45 g (339 mmol) cyclopentanecarbonyl chloride are added slowly. The reaction mixture is stirred for 2 hours at −10° C. and then 1 hour at room temperature. At 0° C., 50 ml of water are added. The mixture is diluted with water and dichloromethane, filtered and the solid product washed with water/dichloromethane 9/1, toluene and diethylether.

Yield: 52.4 g (77%)

$^1$H-NMR (DMSO-$d_6$, 300 MHz): δ=0.9 (t, 3H), 1.6 (m, 10H), 2.6 (m, 1H), 4.1 (m, 2H), 7.9 (d, 1H), 12.4 (s, 1H) ppm.

EXAMPLE 99A

Ethyl 3-[(cyclopentylcarbonyl)amino]-2-oxopentanoate

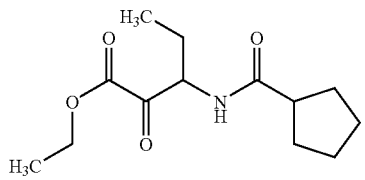

1.6 g (8 mmol) 2-[(cyclopentylcarbonyl)amino]butanoic acid are suspended in 30 ml tetrahydrofurane and heated to reflux together with 1.91 g (24 mmol) pyridine and a bit of N,N-dimethylaminopyridine. While heating at reflux, 2.19 g (16 mmol) ethyl chloro(oxo)acetate are added dropwise. The reaction mixture is heated at reflux until no more evolution of gas can be observed. After cooling down to room temperature, the reaction mixture is added to ice water and the organic phase extracted with ethyl acetate. The dried organic phase is evaporated to dryness in vacuo, dissolved in ethanol and the solution directly used for the next reaction.

EXAMPLE 100A

4-Methyl-1-naphthalenecarboximidamide hydrochloride

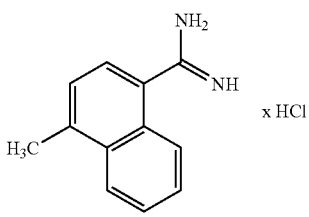

In analogy to the procedure for Example 3A, 13 g (78 mmol) 4-methyl-1-naphthonitrile and proportionate amounts of the other reagents are used.

Yield: 4.6 g (27%).

EXAMPLE 101A

4-Nitrobenzenecarboximidamide hydrochloride

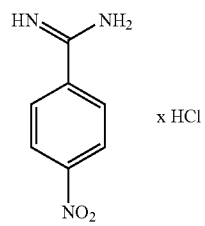

In analogy to the procedure for Example 3A, 10.0 g (67.5 mmol) 4-nitrobenzonitrile and proportionate amounts of the other reagents are used.

Yield: 12.64 g (93%)

$^1$H-NMR (DMSO-d$_6$, 200 MHz): δ=8.1 (m, 2H), 8.4 (m, 2H) ppm.

EXAMPLE 102A

3-Cyanobenzenecarboximidamide hydrochloride

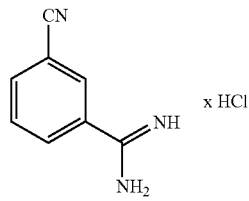

In analogy to the procedure for Example 3A, 20.0 g (125.9 mmol) 3-cyanobenzoic acid and proportionate amounts of the other reagents are used.

Yield: 4.27 g (17%)

$^1$H-NMR (DMSO-d$_6$, 300 MHz): δ=7.8 (m, 1H), 8.1 (m, 1H), 8.2 (m, 1H), 8.3 (m, 1H), 9.4 (br.s, 4H) ppm.

EXAMPLE 103A

N-{1-[3-(4-Methyl-1-naphthyl)-5-oxo-4,5-dihydro-1,2,4-triazin-6-yl]propyl}acetamide

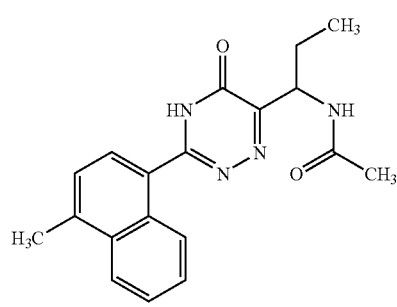

In analogy to the procedure for Example 10A, 11.0 g (50 mmol) 4-methyl-1-naphthalenecarboximidamide hydrochloride and proportionate amounts of the other reagents are used.

Yield: 8.0 g (48%)

$^1$H-NMR (200 MHz, CDCl$_3$): δ=0.88 (t, 3H), 1.77–2.06 (m, 5H, s at 1.80), 2.74 (s, 3H), 5.00 (m, 1H), 7.12 (d, 1H, NH), 7.36 (d, 1H), 7.48–7.71 (m, 3H), 8.01–8.11 (m, 1H), 8.25–8.34 (m, 1H) 13.05 (s, 1H, NH) ppm.

EXAMPLE 104A

N-{1-[3-(4-Methylphenyl)-5-oxo-4,5-dihydro-1,2,4-triazin-6-yl]propyl}acetamide

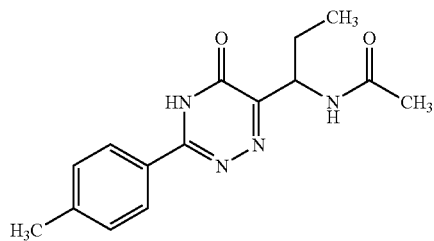

In analogy to the procedure for Example 10A, 3.0 g (17.6 mmol) 4-methylbenzenecarboximidamide hydrochloride and proportionate amounts of the other reagents are used.

Yield: 2.74 g (54%)

$^1$H-NMR (DMSO-d$_6$, 400 MHz): δ=0.9 (t, 3H), 1.6 (m, 1H), 1.9 (m, 1H; s, 3H), 2.4 (s, 3H), 4.9 (m, 1H), 7.4 (m, 2H), 7.9 (m, 2H), 14.0 (s, 1H) ppm.

EXAMPLE 105A

N-{1-[3-(4-Nitrophenyl)-5-oxo-4,5-dihydro-1,2,4-triazin-6-yl]propyl}acetamide

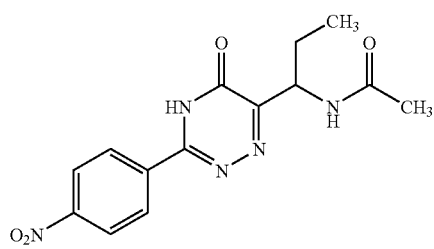

In analogy to the procedure for Example 10A, 7.29 g (36.16 mmol) of Example 101A and proportionate amounts of the other reagents are used.

Yield: 3.35 g (29%)

$^1$H-NMR (DMSO-d$_6$, 400 MHz): δ=0.9 (t, 3H), 1.6 (m, 1H), 1.9 (m, 1H; s, 3H), 5.0 (m, 1H), 8.1 (d, 1H), 8.3 (m, 2H), 8.4 (m, 2H) ppm.

EXAMPLE 106A

N-{1-[3-(4-Butylphenyl)-5-oxo-4,5-dihydro-1,2,4-triazin-6-yl]propyl}acetamide

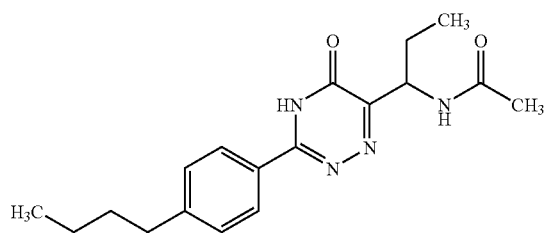

In analogy to the procedure for Example 10A, 6.27 g (29.5 mmol) 4-butylbenzenecarboximidamide hydrochloride and proportionate amounts of the other reagents are used.

Yield: 4.24 g (44%)

LC/MS (A): MS (ESI): 329 (M+H$^+$), retention time 2.30 min

EXAMPLE 107A

N-{-[3-(3-Cyanophenyl)-5-oxo-4,5-dihydro-1,2,4-triazin-6-yl]propyl}acetamide

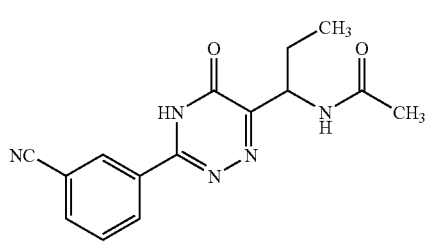

In analogy to the procedure for Example 10A, 4.27 g (23.5 mmol) of Example 102A and proportionate amounts of the other reagents are used.

Yield: 2.41 g (34%)

$^1$H-NMR (DMSO-d$_6$, 300 MHz): δ=0.9 (t, 3H), 1.6 (m, 1H), 1.9 (m, 1H; s, 3H), 4.9 (m, 1H), 7.8 (m, 1H), 8.1 (m, 2H), 8.3 (m, 1H), 8.4 (m, 1H), 14.2 (br.s, 1H) ppm.

EXAMPLE 108A 6-(1-Aminopropyl)-3-(4-methyl-1-naphthyl)-1,2,4-triazin-5(4H)-one

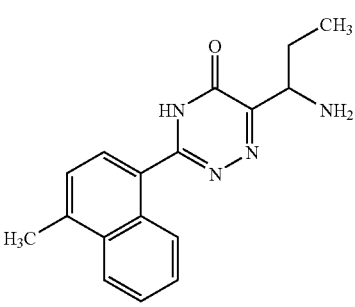

In analogy to the procedure for Example 23A, 8.0 g (23.8 mmol) N-{1-[3-(4-methyl-1-naphthyl)-5-oxo-4,5-dihydro-1,2,4-triazin-6-yl]propyl}acetamide and proportionate amounts of the other reagents are used.

$^1$H-NMR (300 MHz, DMSO-d$_6$): δ=0.94 (t, 3H), 1.82–2.10 (m, 2H), 2.70 (s, 3H), 4.28 (m, 1H), 7.42 (d, 1H), 7.46–7.60 (m, 2H), 7.67 (d, 1H), 8.06 (d, 1H), 8.53 (d, 1H) ppm.

EXAMPLE 109A 6-(1-Aminopropyl)-3-(4-methylphenyl)-1,2,4-triazin-5(4H)-one

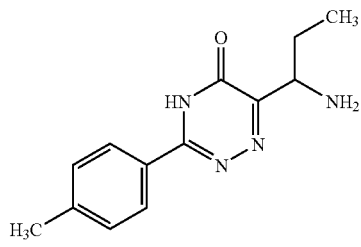

In analogy to the procedure for Example 23A, 2.74 g (9.57 mmol) of Example 104A and proportionate amounts of the other reagents are used. The product is used in the next step without further purification.

$^1$H-NMR (DMSO-d$_6$, 300 MHz): δ=0.9 (t, 3H), 1.8 (m, 1H), 1.9 (m, 1H), 2.3 (s, 3H), 4.1 (d/d, 1H), 7.2 (m, 2H), 8.1 (m, 2H) ppm.

EXAMPLE 110A 6-(1-Aminopropyl)-3-(4-nitrophenyl)-1,2,4-triazin-5(4H)-one

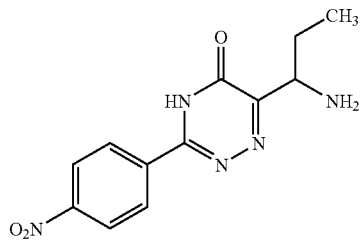

In analogy to the procedure for Example 23A, 3.33 g (10.51 mmol) of Example 105A and proportionate amounts of the other reagents are used.

Yield: 1.29 g (45%)

LC/MS (A): MS (ESI): 276 (M+H$^+$), retention time 0.49 min.

EXAMPLE 111A 6-(1-Aminopropyl)-3-(4-butylphenyl)-1,2,4-triazin-5(4H)-one

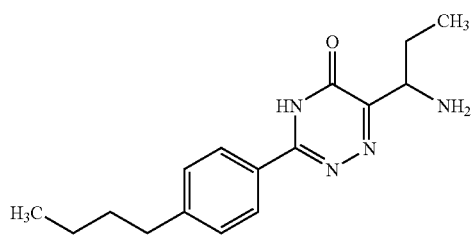

In analogy to the procedure for Example 23A, 4.24 g (12.9 mmol) of Example 106A and proportionate amounts of the other reagents are used.

Yield: 3.03 g (82%)

$^1$H-NMR (DMSO-d$_6$, 300 MHz): δ=0.9 (t, 3H), 0.9 (t, 3H), 1.3 (m, 2H), 1.6 (m, 2H), 1.9 (m, 1H), 2.0 (m, 1H), 2.6 (m, 2H), 4.2 (m, 1H), 7.2 (m, 2H), 8.1 (m, 2H) ppm.

EXAMPLE 112A

3-[6-(1-Aminopropyl)-5-oxo-4,5-dihydro-1,2,4-triazin-3-yl]benzonitrile

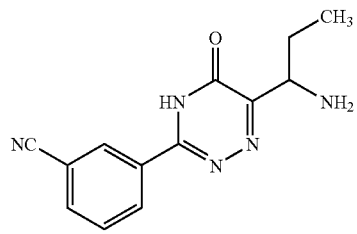

In analogy to the procedure for Example 23A, 2.41 g (8.11 mmol) of Example 107A and proportionate amounts of the other reagents are used.

Yield: 1.1 g (53%)

LC/MS (A): MS (ESI): 256 (M+H$^+$), retention time 1.27 min.

EXAMPLE 113A

N-{1-[3-(4-Methyl-1-naphthyl)-5-oxo-4,5-dihydro-1,2,4-triazin-6-yl]propyl}cyclopentanecarboxamide

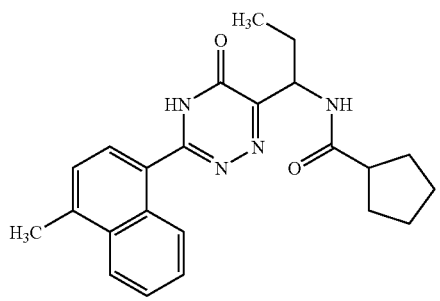

In analogy to the procedure for Example 36A, 600 mg (2.04 mmol) 6-(1-aminopropyl)-3-(4-methyl-1-naphthyl)-1,2,4-triazin-5(4H)-one, 270 mg (2.04 mmol) cyclopentanecarbonyl chloride and proportionate amounts of the other reagents are used. The crude product is used in the next step without further purification.

Yield: 82 mg (57%)

LC/MS (A): MS (ESI): 329 (M+H$^+$), retention time 2.7 min.

EXAMPLE 114A

N-{1-[3-(4-Methylphenyl)-5-oxo-4,5-dihydro-1,2,4-triazin-6-yl]propyl}cyclobutanecarboxamide

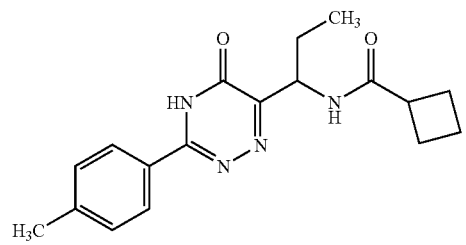

In analogy to the procedure for Example 36A, 400 mg (1.64 mmol) of Example 109A, 213 mg (1.80 mmol) cyclobutanecarbonyl chloride and proportionate amounts of the other reagents are used.

Yield: 422 mg (79%)

LC/MS (A): MS (ESI): 327 (M+H$^+$), retention time 2.20 min.

EXAMPLE 115A

N-{1-[3-(4-Methylphenyl)-5-oxo-4,5-dihydro-1,2,4-triazin-6-yl]propyl}cyclopentanecarboxamide

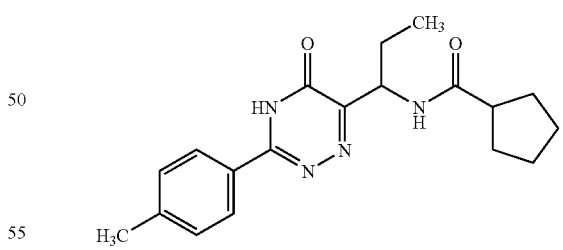

In analogy to the procedure for Example 36A, 400 mg (1.64 mmol) of Example 109A, 213 mg (1.80 mmol) cyclopentanecarbonyl chloride and proportionate amounts of the other reagents are used.

Yield: 323 mg (58%)

LC/MS (A): MS (ESI): 341 (M+H$^+$), retention time 2.34 min.

EXAMPLE 116A

N-[1-(3-Cyclopentyl-5-oxo-4,5-dihydro-1,2,4-triazin-6-yl)propyl]-2-methylcyclopropanecarboxamide

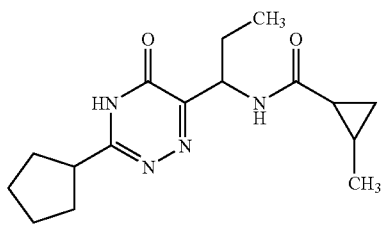

In analogy to the procedure for Example 36A, 150 mg (0.67 mmol) 6-(1-aminopropyl)-3-cyclopentyl-1,2,4-triazin-5(4H)-one, 90 mg (0.74 mmol) 2-methyl-cyclopropylcarbonyl chloride and proportionate amounts of the other reagents are used. The crude product is used in the next step without further purification.

LC/MS (B): MS (ESI): 305 (M+H$^+$), retention time 3.06 min.

EXAMPLE 117A

N-[1-(3-Cyclopentyl-5-oxo-4,5-dihydro-1,2,4-triazin-6-yl)propyl]cyclopropanecarboxamide

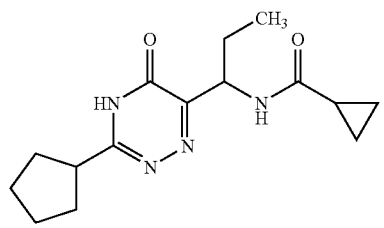

In analogy to the procedure for Example 36A, 150 mg (0.67 mmol) 6-(1-aminopropyl)-3-cyclopentyl-1,2,4-triazin-5(4H)-one, 80 mg (0.74 mmol) cyclopropylcarbonyl chloride and proportionate amounts of the other reagents are used. The crude product is used in the next step without further purification.

LC/MS (B): MS (ESI): 291 (M+H$^+$), retention time 2.77 min.

EXAMPLE 118A

N-[1-(3-Cyclopentyl-5-oxo-4,5-dihydro-1,2,4-triazin-6-yl)propyl]-1,4-dimethylcyclohexanecarboxamide

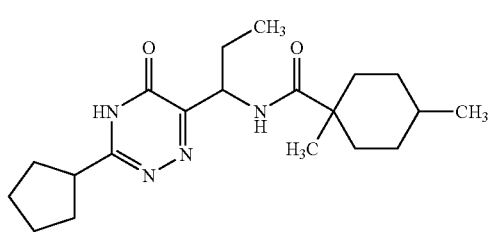

In analogy to the procedure for Example 36A, 150 mg (0.67 mmol) 6-(1-aminopropyl)-3-cyclopentyl-1,2,4-triazin-5(4H)-one, 130 mg (0.74 mmol) 1,4-dimethylcyclohexanecarbonyl chloride and proportionate amounts of the other reagents are used. The crude product is used in the next step without further purification.

LC/MS (B): MS (ESI): 361 (M+H$^+$), retention time 4.09 min.

EXAMPLE 119A

N-[1-(3-Cyclopentyl-5-oxo-4,5-dihydro-1,2,4-triazin-6-yl)propyl]bicyclo[2.2.1]hept-5-ene-2-carboxamide

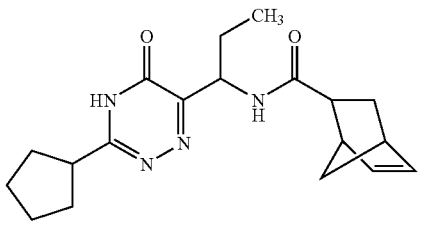

In analogy to the procedure for Example 36A, 150 mg (0.67 mmol) 6-(1-aminopropyl)-3-cyclopentyl-1,2,4-triazin-5(4H)-one, 120 mg (0.74 mmol) bicyclo[2.2.1]hept-5-ene-2-carbonyl chloride and proportionate amounts of the other reagents are used. The crude product is used in the next step without further purification.

LC/MS (B): MS (ESI): 343 (M+H$^+$), retention time 3.40 min.

EXAMPLE 120A

2-Bicyclo[2.2.1]hept-2-yl-N-[1-(3-cyclopentyl-5-oxo-4,5-dihydro-1,2,4-triazin-6-yl)propyl]acetamide

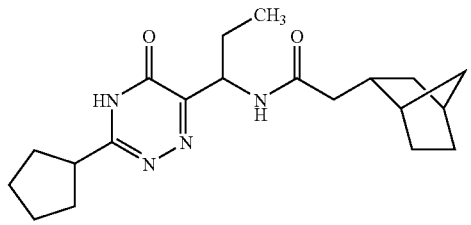

In analogy to the procedure for Example 36A, 150 mg (0.67 mmol) 6-(1-aminopropyl)-3-cyclopentyl-1,2,4-triazin-5(4H)-one, 130 mg (0.74 mmol) bicyclo[2.2.1]hept-2-ylacetyl chloride and proportionate amounts of the other reagents are used. The crude product is used in the next step without further purification.

LC/MS (B): MS (ESI): 358 (M+H$^+$), retention time 3.78 min.

EXAMPLE 121A

N-[1-(3-Cyclopentyl-5-oxo-4,5-dihydro-1,2,4-triazin-6-yl)propyl]-2-methylcyclohexanecarboxamide

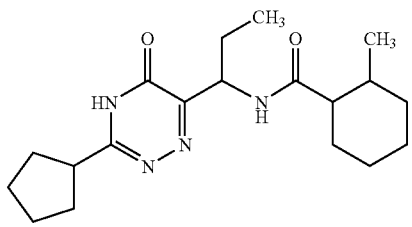

In analogy to the procedure for Example 36A, 150 mg (0.67 mmol) 6-(1-aminopropyl)-3-cyclopentyl-1,2,4-triazin-5(4H)-one, 120 mg (0.74 mmol) 2-methylcyclohexanecarbonyl chloride and proportionate amounts of the other reagents are used. The crude product is used in the next step without further purification.

LC/MS (B): MS (ESI): 347 (M+H$^+$), retention time 3.64 min.

EXAMPLE 122A

N-[1-(3-Cyclopentyl-5-oxo-4,5-dihydro-1,2,4-triazin-6-yl)propyl]-3-methylbutanamide

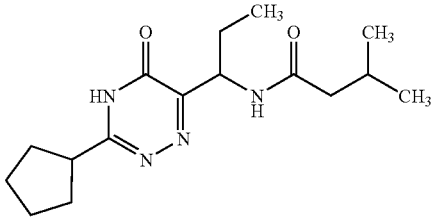

In analogy to the procedure for Example 36A, 150 mg (0.67 mmol) 6-(1-aminopropyl)-3-cyclopentyl-1,2,4-triazin-5(4H)-one, 90 mg (0.74 mmol) 3-methylbutanoyl chloride and proportionate amounts of the other reagents are used. The crude product is used in the next step without further purification.

LC/MS (B): MS (ESI): 307 (M+H$^+$), retention time 3.12 min.

EXAMPLE 123A

N-[1-(3-Cyclopentyl-5-oxo-4,5-dihydro-1,2,4-triazin-6-yl)propyl]-1-methylcyclohexanecarboxamide

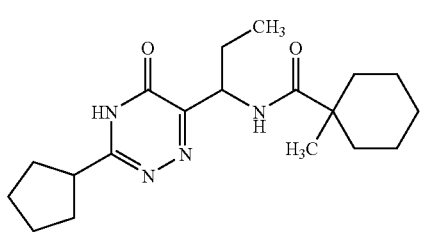

In analogy to the procedure for Example 36A, 150 mg (0.67 mmol) 6-(1-aminopropyl)-3-cyclopentyl-1,2,4-triazin-5(4H)-one, 120 mg (0.74 mmol) 1-methylcyclohexanecarbonyl chloride and proportionate amounts of the other reagents are used. The crude product is used in the next step without further purification.

LC/MS (B): MS (ESI): 347 (M+H$^+$), retention time 3.81 min.

EXAMPLE 124A

N-[1-(3-Cyclopentyl-5-oxo-4,5-dihydro-1,2,4-triazin-6-yl)propyl]pentanamide

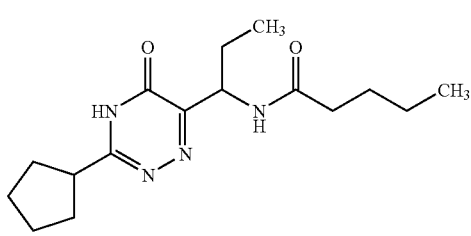

In analogy to the procedure for Example 36A, 150 mg (0.67 mmol) 6-(1-aminopropyl)-3-cyclopentyl-1,2,4-triazin-5(4H)-one, 90 mg (0.74 mmol) pentanoyl chloride and proportionate amounts of the other reagents are used. The crude product is used in the next step without further purification.

LC/MS (B): MS (ESI): 307 (M+H$^+$), retention time 3.20 min.

EXAMPLE 125A

N-[1-(3-Cyclopentyl-5-oxo-4,5-dihydro-1,2,4-triazin-6-yl)propyl]-1-adamantanecarboxamide

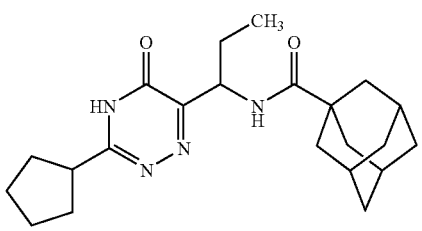

In analogy to the procedure for Example 36A, 150 mg (0.67 mmol) 6-(1-aminopropyl)-3-cyclopentyl-1,2,4-triazin-5(4H)-one, 150 mg (0.74 mmol) 1-adamantanecarbonyl chloride and proportionate amounts of the other reagents are used. The crude product is used in the next step without further purification.

LC/MS (B): MS (ESI): 385 (M+H$^+$), retention time 4.14 min.

EXAMPLE 126A

N-[1-(3-Cyclopentyl-5-oxo-4,5-dihydro-1,2,4-triazin-6-yl)propyl]-2,2-dimethylpropanamide

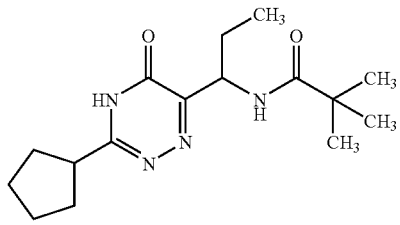

In analogy to the procedure for Example 36A, 150 mg (0.67 mmol) 6-(1-aminopropyl)-3-cyclopentyl-1,2,4-triazin-5(4H)-one, 90 mg (0.74 mmol) 2,2-dimethylpropanoyl chloride and proportionate amounts of the other reagents are used. The crude product is used in the next step without further purification.

LC/MS (B): MS (ESI): 307 (M+H$^+$), retention time 3.29 min.

EXAMPLE 127A

2-Cyclohexyl-N-[1-(3-cyclopentyl-5-oxo-4,5-dihydro-1,2,4-triazin-6-yl)propyl]acetamide

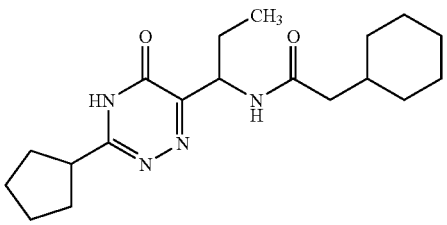

In analogy to the procedure for Example 58A, 150 mg (0.67 mmol) 6-(1-aminopropyl)-3-cyclopentyl-1,2,4-triazin-5(4H)-one, 96 mg (0.67 mmol) cyclo-hexylacetic acid and proportionate amounts of the other reagents are used. The crude product is used in the next step without further purification.

LC/MS (B): MS (ESI): 347 (M+H$^+$), retention time 3.69 min.

EXAMPLE 128A

N-[1-(3-Cyclopentyl-5-oxo-4,5-dihydro-1,2,4-triazin-6-yl)propyl]-2-ethylhexanamide

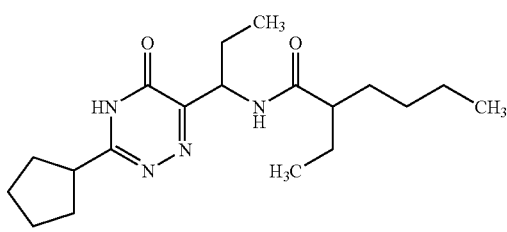

In analogy to the procedure for Example 58A, 150 mg (0.67 mmol) 6-(1-aminopropyl)-3-cyclopentyl-1,2,4-triazin-5(4H)-one, 97 mg (0.67 mmol) 2-ethyl-hexanoic acid and proportionate amounts of the other reagents are used. The crude product is used in the next step without further purification.

LC/MS (B): MS (ESI): 349 (M+H$^+$), retention time 3.86 min.

EXAMPLE 129A

N-[1-(3-Cyclopentyl-5-oxo-4,5-dihydro-1,2,4-triazin-6-yl)propyl]-2,2-dimethylbutanamide

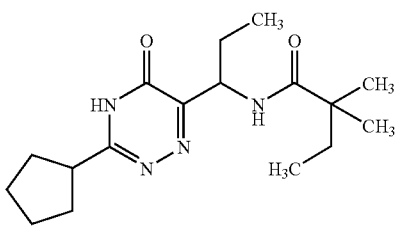

In analogy to the procedure for Example 58A, 150 mg (0.67 mmol) 6-(1-aminopropyl)-3-cyclopentyl-1,2,4-triazin-5(4H)-one, 78 mg (0.67 mmol) 2,2-dimethylbutanoic acid and proportionate amounts of the other reagents are used. The crude product is used in the next step without further purification.

LC/MS (A): MS (ESI): 321 (M+H$^+$), retention time 2.28 min.

EXAMPLE 130A

Benzyl 4-({[1-(3-cyclopentyl-5-oxo-4,5-dihydro-1,2,4-triazin-6-yl)propyl]amino}carbonyl)-1-piperidinecarboxylate

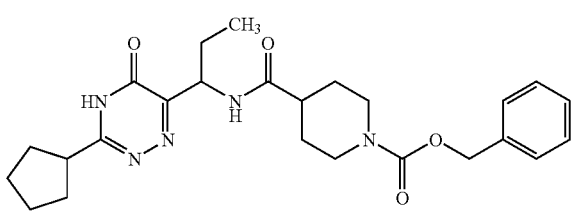

In analogy to the procedure for Example 58A, 300 mg (1.35 mmol) 6-(1-aminopropyl)-3-cyclopentyl-1,2,4-triazin-5(4H)-one, 355 mg (1.35 mmol) 1-[(benzyloxy)carbonyl]-4-piperidinecarboxylic acid and proportionate amounts of the other reagents are used. The crude product is used in the next step without further purification.

LC/MS (A): MS (ESI): 468 (M+H$^+$), retention time 2.34 min.

EXAMPLE 131A

N-[1-(5-Oxo-3-phenyl-4,5-dihydro-1,2,4-triazin-6-yl)propyl]-2-propylpentanamide

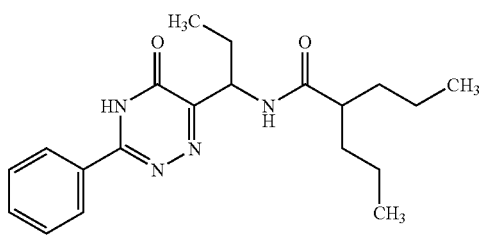

In analogy to the procedure for Example 36A, 100 mg (0.43 mmol) of Example 34A, 78 mg (0.48 mmol) 2-propylpentanoyl chloride and proportionate amounts of the other reagents are used.

Yield: 150 mg (97%)

LC/MS (B): MS (ESI): 329 (M+H$^+$), retention time 3.20 min.

EXAMPLE 132A

4-Isopropyl-N-[1-(5-oxo-3-phenyl-4,5-dihydro-1,2,4-triazin-6-yl)propyl]cyclohexanecarboxamide

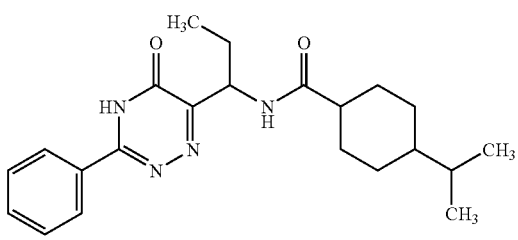

In analogy to the procedure for Example 58A, 100 mg (0.43 mmol) of Example 34A, 74 mg (0.43 mmol) 4-isopropylcyclohexanecarboxylic acid and proportionate amounts of the other reagents are used.

Yield: 150 mg (90%)

LC/MS (B): MS (ESI): 383 (M+H$^+$), retention time 4.03 min.

EXAMPLE 133A

2-Methyl-N-[1-(5-oxo-3-phenyl-4,5-dihydro-1,2,4-triazin-6-yl)propyl]bicyclo[2.2.1]heptane-2-carboxamide

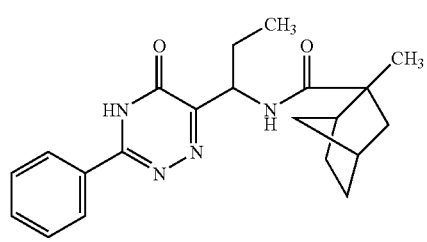

In analogy to the procedure for Example 36A, 100 mg (0.43 mmol) of Example 34A, 78 mg (0.48 mmol) 2-methylbicyclo[2.2.1]heptane-2-carbonyl chloride and proportionate amounts of the other reagents are used.

Yield: 150 mg (94%)

LC/MS (B): MS (ESI): 367 (M+H$^+$), retention time 3.68 min.

EXAMPLE 134A

4-Methyl-N-[1-(5-oxo-3-phenyl-4,5-dihydro-1,2,4-triazin-6-yl)propyl]cyclohexanecarboxamide

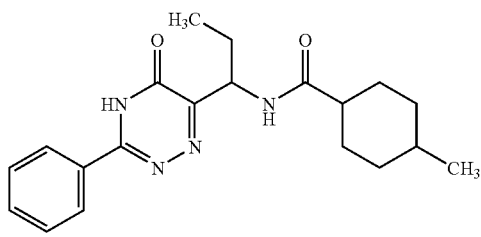

In analogy to the procedure for Example 58A, 200 mg (0.87 mmol) of Example 34A, 124 mg (0.87 mmol) 4-methylcyclohexanecarboxylic acid and proportionate amounts of the other reagents are used.

Yield: 260 mg (84%) of a cis/trans isomeric mixture

LC/MS (B): MS (ESI): 355 (M+H$^+$), retention time 3.56 min.

EXAMPLE 135A

2-Methyl-N-[1-(5-oxo-3-phenyl-4,5-dihydro-1,2,4-triazin-6-yl)propyl]cyclohexanecarboxamide

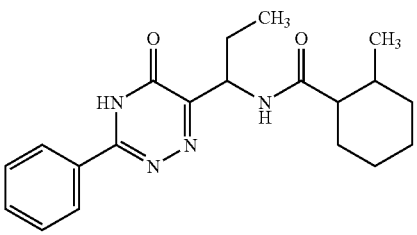

In analogy to the procedure for Example 36A, 100 mg (0.43 mmol) of Example 34A, 77 mg (0.48 mmol) 2-methylcyclohexanecarbonyl chloride and proportionate amounts of the other reagents are used.

Yield: 150 mg (97%)

LC/MS (B): MS (ESI): 355 (M+H$^+$), retention time 3.45 min and 3.54 min.

EXAMPLE 136A

N-{1-[3-(1-Naphthyl)-5-oxo-4,5-dihydro-1,2,4-triazin-6-yl]propyl}-3-(trifluoromethyl)cyclohexanecarboxamide

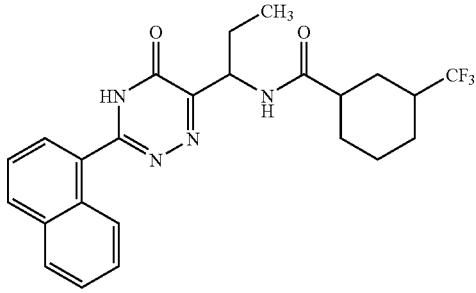

In analogy to the procedure for Example 58A, 100 mg (0.36 mmol) of Example 35A, 70 mg (0.36 mmol) 3-trifluoromethylcyclohexanecarboxylic acid and proportionate amounts of the other reagents are used.

Yield: 160 mg (98%) of a cis/trans isomeric mixture
LC/MS (B): MS (ESI): 459 (M+H$^+$), retention time 3.91 min and 4.00 min.

EXAMPLE 137A

N-{1-[3-(1-Naphthyl)-5-oxo-4,5-dihydro-1,2,4-triazin-6-yl]propyl} 4-(trifluoromethyl)cyclohexanecarboxamide

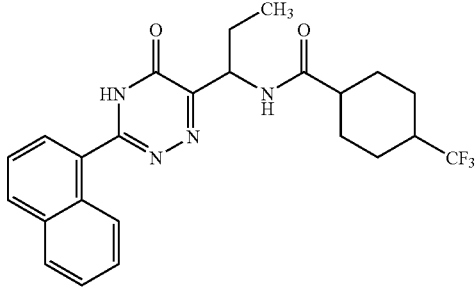

In analogy to the procedure for Example 58A, 100 mg (0.36 mmol) of Example 35A, 70 mg (0.36 mmol) 4-trifluoromethylcyclohexanecarboxylic acid and proportionate amounts of the other reagents are used.

Yield: 160 mg (98%)
LC/MS (B): MS (ESI): 459 (M+H$^+$), retention time 3.89 min.

EXAMPLE 138A 1,4-Dimethyl-N-{1-[3-(1-naphthyl)-5-oxo-4,5-dihydro-1,2,4-triazin-6-yl]propyl}cyclohexanecarboxamide

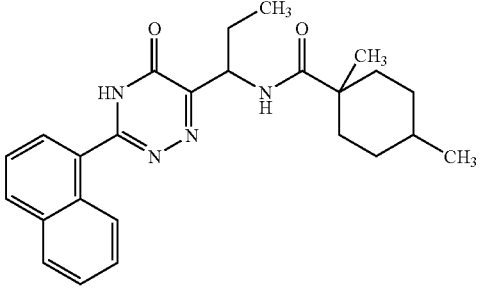

In analogy to the procedure for Example 36A, 100 mg (0.36 mmol) of Example 35A, 70 mg (0.39 mmol) 1,4-dimethylcyclohexanecarbonyl chloride and proportionate amounts of the other reagents are used.

Yield: 150 mg (99%)
LC/MS (B): MS (ESI): 419 (M+H$^+$), retention time 4.16 min.

EXAMPLE 139A

4-Methyl-N-{1-[3-(1-naphthyl)-5-oxo-4,5-dihydro-1,2,4-triazin-6-yl]propyl}cyclohexanecarboxamide

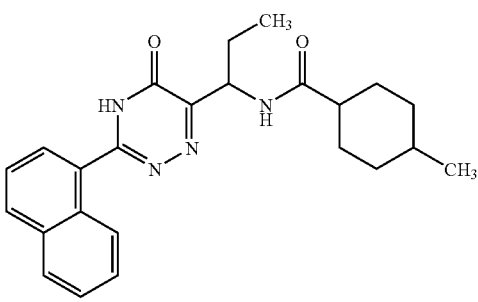

In analogy to the procedure for Example 58A, 100 mg (0.36 mmol) of Example 35A, 60 mg (0.36 mmol) 4-methylcyclohexanecarboxylic acid and proportionate amounts of the other reagents are used.

Yield: 140 mg (97%)
LC/MS (B): MS (ESI): 405 (M+H$^+$), retention time 3.89 min.

EXAMPLE 140A

2-Cyclohexyl-N-{1-[3-(1-naphthyl)-5-oxo-4,5-dihydro-1,2,4-triazin-6-yl]propyl}acetamide

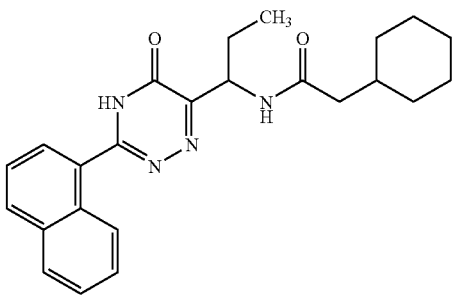

In analogy to the procedure for Example 36A, 100 mg (0.36 mmol) of Example 35A, 60 mg (0.36 mmol) cyclohexylacetyl chloride and proportionate amounts of the other reagents are used.

Yield: 140 mg (97%)
LC/MS (B): MS (ESI): 405 (M+H$^+$), retention time 3.81 min.

EXAMPLE 141A

3-Methyl-N-{1-[3-(1-naphthyl)-5-oxo-4,5-dihydro-1,2,4-triazin-6-yl]propyl}butanamide

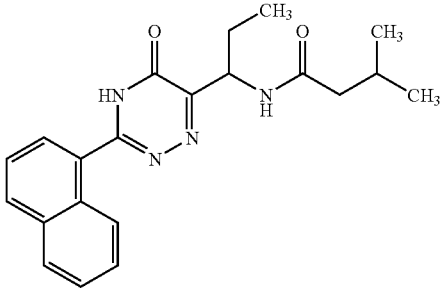

In analogy to the procedure for Example 36A, 100 mg (0.36 mmol) of Example 35A, 50 mg (0.39 mmol) 3-methylbutanoyl chloride and proportionate amounts of the other reagents are used.

Yield: 130 mg (99%)

LC/MS (B): MS (ESI): 365 (M+H$^+$), retention time 3.38 min.

EXAMPLE 142A

N-[1-(5-Oxo-3-phenyl-4,5-dihydro-1,2,4-triazin-6-yl)propyl]-1-adamantanecarboxamide

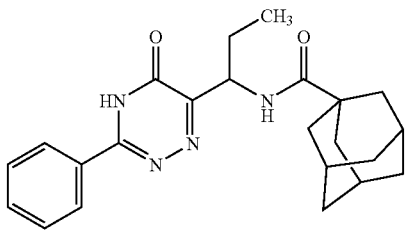

In analogy to the procedure for Example 36A, 100 mg (0.43 mmol) of Example 34A, 95 mg (0.48 mmol) 1-adamantanecarbonyl chloride and proportionate amounts of the other reagents are used.

Yield: 70 mg (41%)

LC/MS (B): MS (ESI): 393 (M+H$^+$), retention time 3.95 min.

EXAMPLE 143A

Benzyl 4-({[1-(5-oxo-3-phenyl-4,5-dihydro-1,2,4-triazin-6-yl)propyl]amino}carbonyl)-1-piperidinecarboxylate

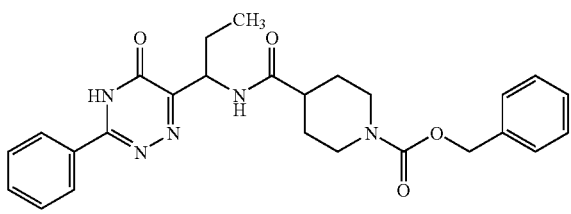

In analogy to the procedure for Example 58A, 1.64 g (7.14 mmol) of Example 34A, 1.88 g (7.14 mmol) 1-[(benzyloxy)carbonyl]4-piperidinecarboxylic acid and proportionate amounts of the other reagents are used.

Yield: 3.4 g (100%)

LC/MS (B): MS (ESI): 474 (M+H$^+$), retention time 3.58 min.

PREPARATION EXAMPLES

Example 1

2-(3-Bromophenyl)-7-cyclopentyl-5-ethylimidazo[5,1-f][1,2,4]triazin-4(3H)-one

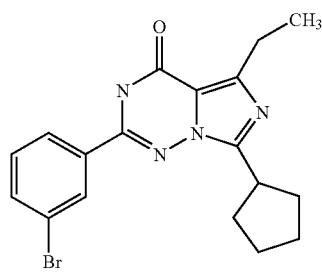

95 mg (0.23 mmol, 1 equiv.) of Example 36A are suspended in 10 ml dichloroethane, and 54 mg (0.35 mmol, 1.5 equiv.) phosphoroxychloride are added. The mixture is stirred at reflux for 1 hour. Then another 54 mg of phosphoric trichloride are added, and stirring at reflux is continued over night. After cooling down to room temperature, ethyl acetate and saturated NaHCO$_3$ (aq) are added. The organic phase is washed with saturated NaHCO$_3$ (aq), water and brine, dried over sodium sulfate and evaporated to dryness in vacuo. The product is purified by chromatography (flash or column chromatography or preparative HPLC).

Yield: 54 mg (60%)

$^1$H-NMR (DMSO-d$_6$, 200 MHz): δ=1.2 (t, 3H), 1.7 (m, 6H), 2.1 (m, 2H), 2.9 (q, 2H), 3.6 (m, 1H), 7.5 (m, 1H), 7.8 (m, 1H), 8.0 (m, 1H), 8.2 (m, 1H), 11.8 (br.s, 1H) ppm.

Example 2

7-Cyclopentyl-5-ethyl-2-(4-fluorophenyl)imidazo[5,1-f][1,2,4]triazin-4(3H)-one

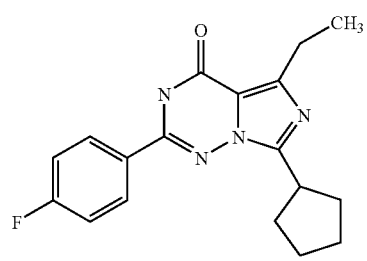

In analogy to the procedure for Example 1, 365 mg (1.06 mmol) of Example 37A, 244 mg (1.59 mmol) phosphoric trichloride are stirred at reflux for 3 hours, proportionate amounts of the solvents are used.

Yield: 182 mg (53%)

$^1$H-NMR (DMSO-$d_6$, 300 MHz): δ=1.2 (t, 3H), 1.7 (m, 2H), 1.8 (m, 4H), 2.1 (m, 2H), 2.9 (q, 2H), 3.6 (m, 1H), 7.4 (m, 2H), 8.0 (m, 2H), 11.8 (s, 1H) ppm.

Example 3

7-Cyclobutyl-5-ethyl-2-(4-fluorophenyl)imidazo[5,1-f][1,2,4]triazin-4(3H)-one

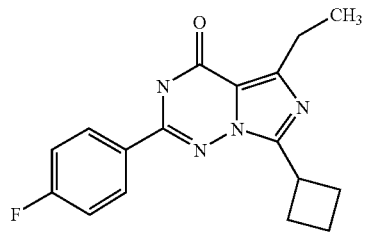

In analogy to the procedure for Example 1, 142 mg (0.43 mmol) of Example 38A, 99 mg (0.64 mmol) phosphoric trichloride are stirred at reflux for 3 hours, proportionate amounts of the solvents are used.

Yield: 37 mg (28%)

$^1$H-NMR (DMSO-$d_6$, 300 MHz): δ=1.2 (t, 3H), 1.9 (m, 1H), 2.0 (m, 1H), 2.4 (m, 4H), 2.9 (q, 2H), 4.0 (m, 1H), 7.4 (m, 2H), 8.0 (m, 2H), 11.8 (s, 1H) ppm.

Example 4

2-(3-Bromophenyl)-7-cyclobutyl-5-ethylimidazo[5,1-f][1,2,4]triazin-4(3H)-one

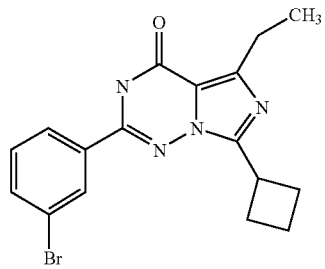

In analogy to the procedure for Example 1, 110 mg (0.28 mmol) of Example 39A, 117 mg (0.77 mmol) phosphoric trichloride are stirred at reflux for 3 hours, proportionate amounts of the solvents are used.

Yield: 55 mg (52%)

$^1$H-NMR (DMSO-$d_6$, 300 MHz): δ=1.2 (t, 3H), 1.4 (m, 1H), 2.1 (m, 1H), 2.4 (m, 4H), 2.4 (q, 2H), 4.0 (m, 1H), 7.5 (m, 1H), 7.8 (m, 1H), 8.0 (m, 1H), 8.2 (m, 1H), 11.9 (s, 1H) ppm.

Example 5

7-Cyclobutyl-5-ethyl-2-(3-fluorophenyl)imidazo[5,1-f][1,2,4]triazin-4(3H)-one

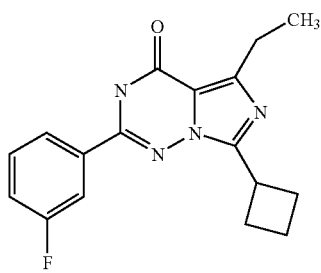

In analogy to the procedure for Example 1, 430 mg (1.30 mmol) of Example 40A, 200 mg (1.30 mmol) phosphoric trichloride are stirred at reflux for 3 hours, proportionate amounts of the solvents are used.

Yield: 149 mg (36%)

$^1$H-NMR (DMSO-$d_6$, 300 MHz): δ=1.2 (t, 3H), 1.9 (m, 1H), 2.1 (m, 1H), 2.4 (m, 4H), 2.9 (q, 2H), 4.0 (m, 1H), 7.4 (m, 1H), 7.6 (m, 1H), 7.8 (m, 2H), 11.9 (s, 1H) ppm.

Example 6

7-Cyclopentyl-5-ethyl-2-(3-fluorophenyl)imidazo[5,1-f][1,2,4]triazin-4(3H)-one

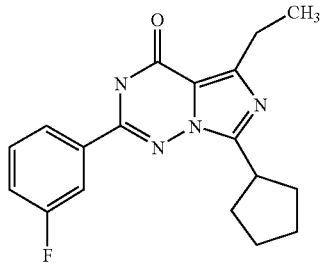

In analogy to the procedure for Example 1, 345 mg (1.00 mmol) of Example 41A, 154 mg (1.00 mmol) phosphoric trichloride are stirred at reflux for 3 hours, proportionate amounts of the solvents are used.

Yield: 181 mg (55%)

$^1$H-NMR (DMSO-$d_6$, 300 MHz): δ=1.2 (t, 3H), 1.7 (m, 2H), 1.8 (m, 4H), 2.1 (m, 2H), 2.9 (q, 2H), 3.6 (m, 1H), 7.4 (m, 1H), 7.6 (m, 1H), 7.8 (m, 2H), 11.9 (s, 1H) ppm.

Example 7

2-(3-Chlorophenyl)-7-cyclopentyl-5-ethylimidazo[5,1-f][1,2,4]triazin-4(3H)-one

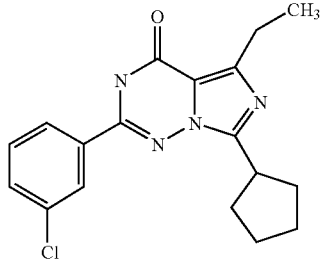

In analogy to the procedure for Example 1, 215 mg (0.60 mmol) of Example 42A, 91 mg (0.60 mmol) phosphoric trichloride are stirred at reflux for 3 hours, proportionate amounts of the solvents are used.

Yield: 97 mg (47%)

$^1$H-NMR (DMSO-d$_6$, 200 MHz): δ=1.2 (t, 3H), 1.8 (m, 6H), 2.1 (m, 2H), 2.9 (q, 2H), 3.6 (m, 1H), 7.6 (m, 2H), 7.9 (m, 1H), 8.0 (m, 1H), 11.9 (s, 1H) ppm.

Example 8

2-(3-Chlorophenyl)-7-cyclobutyl-5-ethylimidazo[5,1-f][1,2,4]triazin-4(3H)-one

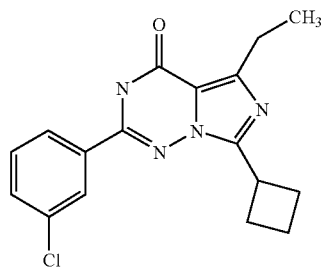

In analogy to the procedure for Example 1, 131 mg (0.38 mmol) of Example 43A, 58 mg (0.38 mmol) phosphoric trichloride are stirred at reflux for 6 hours, then another 58 mg (0.38 mmol) phosphoric trichloride are added, stirring at reflux is continued for 2 hours. Proportionate amounts of the solvents are used.

Yield: 55 mg (44%)

$^1$H-NMR (DMSO-d$_6$, 300 MHz): δ=1.2 (t, 3H), 1.9 (m, 1H), 2.1 (m, 1H), 2.9 (m, 4H), 2.9 (q, 2H), 4.0 (m, 1H), 7.6 (m, 1H), 7.7 (m, 1H), 7.9 (m, 1H), 8.0 (m, 1H), 11.9 (s, 1H) ppm.

Example 9

2-(3-Bromophenyl)-5-ethyl-7-isobutylimidazo[5,1-f][1,2,4]triazin-4(3H)-one

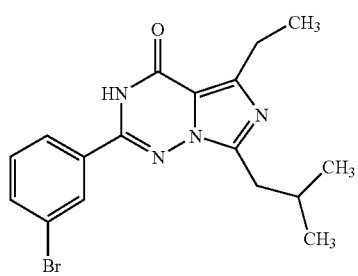

In analogy to the procedure for Example 1, 635 mg (1.61 mmol) of Example 44A, 248 mg (1.61 mmol) phosphoric trichloride are stirred at reflux for 3 hours, proportionate amounts of the solvents are used.

Yield: 312 mg (52%)

$^1$H-NMR (DMSO-d$_6$, 200 MHz): δ=0.9 (d, 6H), 1.3 (t, 3H), 2.2 (m, 1H), 3.0 (m, 4H), 7.5 (m, 1H), 7.9 (m, 1H), 8.0 (m, 1H), 8.2 (m, 1H) ppm.

Example 10

2-(2-Bromophenyl)-7-cyclopentyl-5-ethylimidazo[5,1-f][1,2,4]triazin-4(3H)-one

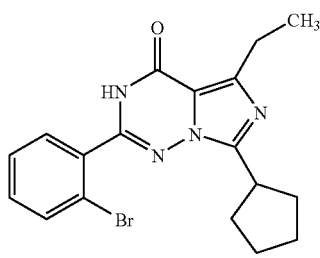

In analogy to the procedure for Example 1, 185 mg (0.46 mmol) of Example 45A, 67 mg (0.46 mmol) phosphoric trichloride are stirred at reflux for 3 hours, then another 630 mg (4.14 mmol) phosphoric trichloride are added, and the reaction mixture is stirred for 48 hours. Proportionate amounts of the solvents are used.

Yield: 36 mg (21%)

$^1$H-NMR (DMSO-d$_6$, 300 MHz): δ=1.2 (t, 3H), 1.6 (m, 2H), 1.7 (m, 2H), 1.9 (m, 2H), 2.0 (m, 2H), 2.9 (q, 2H), 3.5 (m, 1H), 7.5 (m, 2H), 7.7 (m, 1H), 7.8 (m, 1H), 11.9 (s, 1H) ppm.

Example 11

2-Cyclohexyl-7-cyclopentyl-5-ethylimidazo[5,1-f][1,2,4]triazin-4(3H)-one

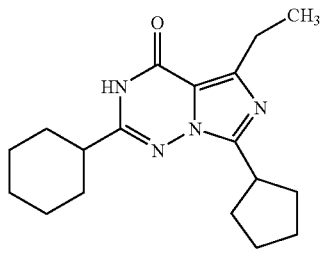

In analogy to the procedure for Example 1, 132 mg (0.40 mmol) of Example 46A, 91 mg (0.60 mmol) phosphoric trichloride are stirred at reflux for 18 hours, proportionate amounts of the solvents are used.

Yield: 94 mg (75%)

$^1$H-NMR (DMSO-d$_6$, 300 MHz): δ=1.2 (t, 3H), 1.3 (m, 2H), 1.5 (m, 2H), 1.7 (m, 4H), 1.8 (m, 6H), 1.9 (m, 4H), 2.5 (m, 1H), 2.8 (q, 2H), 3.5 (m, 1H), 11.3 (s, 1H) ppm.

Example 12

2-(4-Bromophenyl)-7-cyclopentyl-5-ethylimidazo[5,1-f][1,2,4]triazin-4(3H)-one

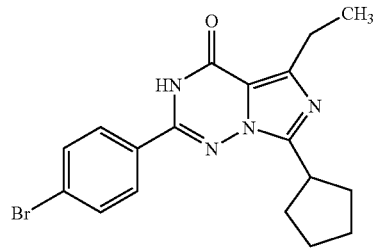

In analogy to the procedure for Example 1, 2.34 g (5.77 mmol) N-{1-[3-(4-bromophenyl)-5-oxo-4,5-dihydro-1,2,4-triazin-6-yl]propyl}cyclopentanecarboxamide, 4.43 g (28.9 mmol) phosphoric trichloride are stirred at reflux for 3 hours, proportionate amounts of the solvents are used.

Yield: 2.05 g (91%)

$^1$H-NMR (400 MHz, CD$_3$OD): δ=1.28 (t, 3H), 1.69–2.19 (m, 8H), 2.98 (q, 2H), 3.68 (quint, 1H), 7.72 (d, 2H), 7.86 (d, 2H) ppm.

Example 13

7-Cyclobutyl-2-cyclopropyl-5-ethylimidazo[5,1-f][1,2,4]triazin-4(3H)-one

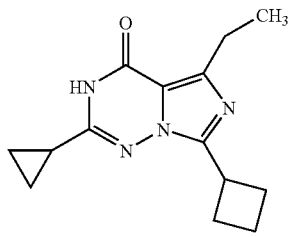

In analogy to the procedure for Example 1, 350 mg (1.28 mmol) crude N-[1-(3-cyclopropyl-5-oxo-4,5-dihydro-1,2,4-triazin-6-yl)propyl]cyclobutanecarboxamide, 200 mg (1.28 mmol) phosphoric trichloride are stirred at reflux for 3 hours, proportionate amounts of the solvents are used.

Yield: 0.1 g (30%)

$^1$H-NMR (400 MHz, CD$_3$OD): δ=0.99–1.13 (m, 4H), 1.25 (t, 3H), 1.74–1.81 (m, 1H), 1.93–2.00 (m, 1H), 2.06–2.17 (m, 1H), 2.28–2.39 (m, 2H), 2.41–2.54 (m, 2H), 2.92 (q, 2H), 3.96 (quint, 1H) ppm.

Example 14

7-Cyclopentyl-2-cyclopropyl-5-ethylimidazo[5,1-f][1,2,4]triazin-4(3H)-one

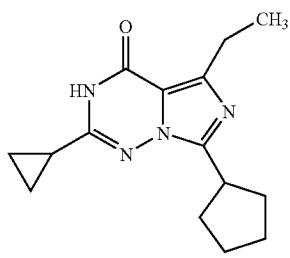

In analogy to the procedure for Example 1, 370 mg (1.28 mmol) crude N-[1-(3-cyclopropyl-5-oxo-4,5-dihydro-1,2,4-triazin-6-yl)propyl]cyclopentanecarboxamide, 200 mg (1.28 mmol) phosphoric trichloride are stirred at reflux for 3 hours, proportionate amounts of the solvents are used.

Yield: 113 mg (32%)

$^1$H-NMR (400 MHz, CD$_3$OD): δ=0.99–1.13 (m, 4H), 1.25 (t, 3H), 1.64–1.94 (m, 9H), 2.00–2.12 (m, 2H), 2.91 (q, 2H), 3.50 (quint, 1H) ppm.

Example 15

7-Cyclobutyl-5-ethyl-2-(1-naphthyl)imidazo[5,1-f][1,2,4]triazin-4(3H)-one

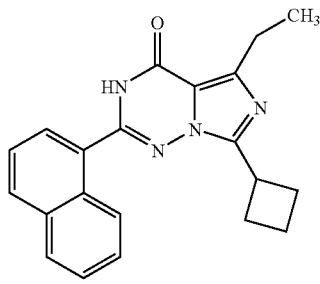

A solution of 190 mg (0.52 mmol) of Example 97A and 96 mg (0.63 mmol) phosphoric trichloride in 10 ml 1,2-dichloroethane is stirred at reflux for 4 h. After work-up analogously to the procedure given for Example 1, the product is obtained as a solid.

Yield: 140 mg (76%)

Melting point: 166° C.

$^1$H-NMR (DMSo-d$_6$, 200 MHz): δ=11.9 (s, 1H) 8.3–7.5 (m, 7H), 3.5 (m, 1H), 2.9 (q, J=7.5 Hz, 2H), 2.5–1.7 (m, 6H), 1.3 (t, J=7.5 Hz, 3H) ppm.

Example 16

2-tert-Butyl-7-cyclopentyl-5-ethylimidazo[5,1-f][1,2,4]triazin-4(3H)-one

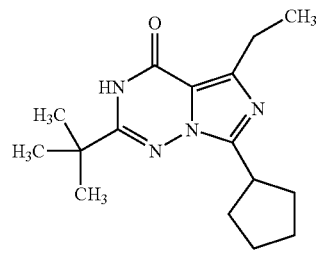

In analogy to the procedure for Example 1, 150 mg (0.50 mmol) crude N-[1-(3-tert-butyl-5-oxo-4,5-dihydro-1,2,4-triazin-6-yl)propyl]cyclopentanecarboxamide, 80 mg (0.50 mmol) phosphoric trichloride are stirred at reflux for 3 hours, proportionate amounts of the solvents are used.

Yield: 70 mg (49%)

$^1$H-NMR (400 MHz, CD$_3$OD): δ=1.25 (t, 3H), 1.36 (m, 9H), 1.67–1.77 (m, 2H), 1.84–1.97 (m, 4H), 2.04–2.13 (m, 2H), 2.92 (q, 2H), 3.58 (quin., 1H) ppm.

Example 17

7-Cyclobutyl-2-cyclopentyl-5-ethylimidazo[5,1-f][1,2,4]triazin-4(3H)-one

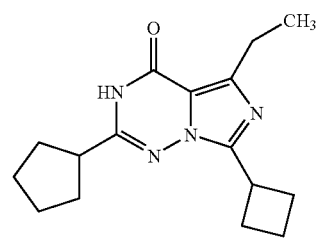

In analogy to the procedure for Example 1, 270 mg (0.90 mmol) crude N-[1-(3-cyclopentyl-5-oxo-4,5-dihydro-1,2,4-triazin-6-yl)propyl]cyclobutanecarboxamide, 140 mg (0.90 mmol) phosphoric trichloride are stirred at reflux for 3 hours, proportionate amounts of the solvents are used.

Yield: 156 mg (61%)

¹H-NMR (300 MHz, CD₃OD): δ=1.26 (t, 3H), 1.62–2.44 (m, 15H), 2.45–2.62 (m, 2H), 2.94 (q, 2H), 4.01 (m, 1H) ppm.

Example 18

2,7-Dicyclopentyl-5-ethylimidazo[5,1-f][1,2,4]triazin-4(3H)-one

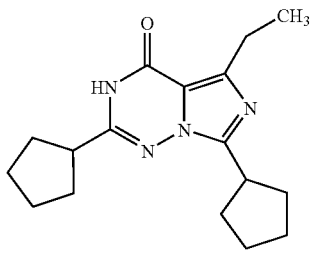

In analogy to the procedure for Example 1, 290 mg (0.90 mmol) crude N-[1-(3-cyclopentyl-5-oxo-4,5-dihydro-1,2,4-triazin-6-yl)propyl]cyclopentanecarboxamide, 140 mg (0.90 mmol) phosphoric trichloride are stirred at reflux for 3 hours, proportionate amounts of the solvents are used.

Yield: 190 mg (70%)

¹H-NMR (300 MHz, CD₃OD): δ=1.25 (t, 3H), 1.62–2.14 (m, 16H), 2.87–3.03 (m, 3H), 3.56 (quin., 1H) ppm.

Example 19

7-Cyclopentyl-5-ethyl-2-(3-nitrophenyl)imidazo[5,1-f][1,2,4]triazin-4(3H)-one

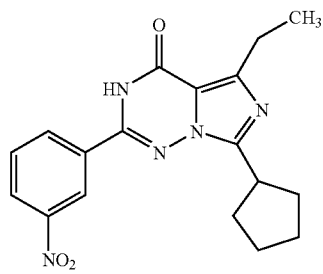

In analogy to the procedure for Example 1, 3.5 g (9.4 mmol) N-{1-[3-(3-nitrophenyl)-5-oxo-4,5-dihydro-1,2,4-triazin-6-yl]propyl}cyclopentanecarboxamide, 1.45 g (9.4 mmol) phosphoric trichloride are stirred at reflux for 3 hours, proportionate amounts of the solvents are used.

Yield: 1.8 g (54%)

¹H-NMR (200 MHz, CDCl₃): δ=1.33 (t, 3H), 1.63–2.22 (m, 8H), 3.03 (q, 2H), 3.68 (quin., 1H), 7.76 (t, 1H), 8.38–8.48 (m, 2H), 8.89–8.95 (s, 1H), 10.85 (s, 1H, NH) ppm.

Example 20

7-Cyclopentyl-5-ethyl-2-phenylimidazo[5,1-f][1,2,4]triazin-4(3H)-one

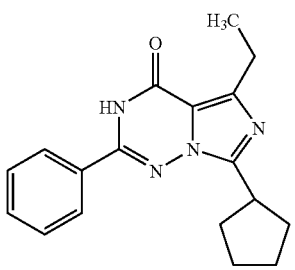

In analogy to the procedure for Example 1, 1.49 g (4.56 mmol) of Example 54A, 0.70 g (4.56 mmol) phosphoric trichloride are stirred at reflux for 3 hours, proportionate amounts of the solvents are used.

Yield: 737 mg (50%)

¹H-NMR (300 MHz, DMSO): δ=1.26 (t, 3H), 1.63–2.17 (m, 8H), 2.95 (q, 2H), 3.66 (quint, 1H), 7.49–7.70 (m, 3H), 7.91–8.01 (m, 2H), 12.18 (s, 1H) ppm.

Example 21

5-Ethyl-7-(2-methylcyclopropyl)-2-phenylimidazo[5,1-f][1,2,4]triazin-4(3H)-one

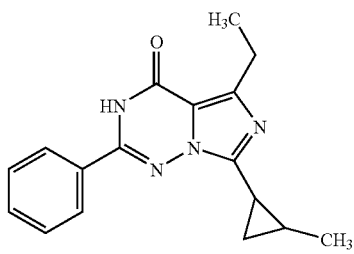

In analogy to the procedure for Example 1, 37 mg (0.12 mmol) of Example 55A, 20 mg (0.12 mmol) phosphoric trichloride are stirred at reflux for 3 hours, proportionate amounts of the solvents are used.

Yield: 20 mg (57%)

LC/MS (A): MS (ESI): 295 (M+H⁺), retention time 3.62 min.

Example 22

7-Cyclobutyl-5-ethyl-2-phenylimidazo[5,1-f][1,2,4]triazin-4(3H)-one

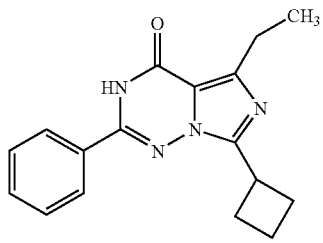

In analogy to the procedure for Example 1, 150 mg (0.48 mmol) of Example 56A, 74 mg (0.48 mmol) phosphoric trichloride are stirred at reflux for 3 hours, proportionate amounts of the solvents are used.

Yield: 25 mg (15%)

$^1$H-NMR (200 MHz, DMSO): δ=1.23 (t, 3H), 1.80–2.61 (m, 6H), 2.90 (q, 2H), 4.01 (quint, 1H), 7.44–7.64 (m, 3H), 7.88–8.02 (m, 2H), 11.83 (s, 1H) ppm.

Example 23

5-Ethyl-2-phenyl-7-tetrahydro-3-furanylimidazo[5,1-f][1,2,4]triazin-4(3H)-one

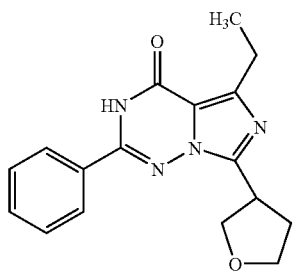

In analogy to the procedure for Example 1, 140 mg (0.43 mmol) of Example 57A, 65 mg (0.43 mmol) phosphoric trichloride are stirred at reflux for 3 hours, proportionate amounts of the solvents are used.

Yield: 20 mg (15%)

LC/MS (A): MS (ESI): 311 (M+H$^+$), retention time 3.14 min.

Example 24

5-Ethyl-2-phenyl-7-tetrahydro-2-furanylimidazo[5,1-f][1,2,4]triazin-4(3H)-one

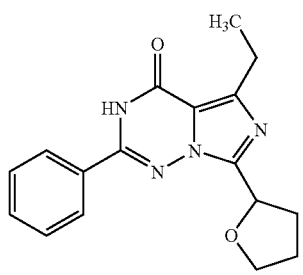

In analogy to the procedure for Example 1, 80 mg (0.24 mmol) of Example 58A, 37 mg (0.24 mmol) phosphoric trichloride are stirred at reflux for 3 hours, proportionate amounts of the solvents are used.

Yield: 32 mg (43%)

LC/MS (A): MS (ESI): 311 (M+H$^+$), retention time 3.36 min.

Example 25

7-Cyclopropyl-5-ethyl-2-phenylimidazo[5,1-f][1,2,4]triazin-4(3H)-one

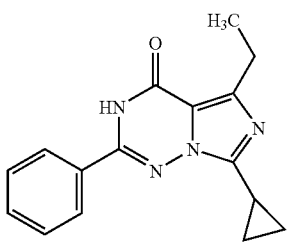

In analogy to the procedure for Example 1, 133 mg (0.45 mmol) of Example 59A, 70 mg (0.45 mmol) phosphoric trichloride are stirred at reflux for 3 hours, proportionate amounts of the solvents are used.

Yield: 19 mg (16%)

$^1$H-NMR (300 MHz, DMSO): δ=0.99–1.12 (m, 4H), 1.18 (t, 3H), 2.83 (q, 2H), 3.28–3.40 (m, 1H), 7.47–7.62 (m, 3H), 7.94–8.05 (m, 2H), 11.76 (s, 1H) ppm.

Example 26

5-Ethyl-2-phenyl-7-tetrahydro-2H-pyran-4-ylimidazo[5,1-f][1,2,4]triazin-4(3H)-one

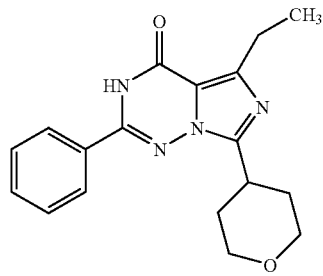

In analogy to the procedure for Example 1, 250 mg (0.73 mmol) of Example 60A, 112 mg (0.73 mmol) phosphoric trichloride are stirred at reflux for 3 hours, proportionate amounts of the solvents are used.

Yield: 15 mg (6%)

$^1$H-NMR (200 MHz, DMSO): δ=1.22 (t, 3H), 1.80–1.95 (m, 4H), 2.89 (q, 2H), 3.39–3.60 (m, 4H), 3.88–4.01 (m, 1H), 7.46–7.64 (m, 3H), 7.92–8.03 (m, 2H), 11.84 (s, 1H) ppm.

Example 27

7-Cyclohexyl-5-ethyl-2-phenylimidazo[5,1-f][1,2,4]triazin-4(3H)-one

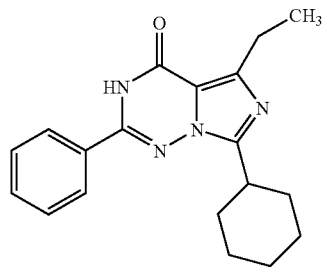

In analogy to the procedure for Example 1, 250 mg (0.73 mmol) of Example 61A, 112 mg (0.73 mmol) phosphoric trichloride are stirred at reflux for 3 hours, proportionate amounts of the solvents are used.

Yield: 18 mg (8%)

$^1$H-NMR (200 MHz, DMSO): δ=1.21 (t, 3H), 1.26–2.03 (m, 10H), 2.81–2.93 (m, 2H), 3.28–3.40 (m, 1H), 7.47–7.62 (m, 3H), 7.94–8.05 (m, 2H) ppm.

Example 28

5-Ethyl-7-(4-methoxycyclohexyl)-2-phenylimidazo[5,1-f][1,2,4]triazin-4(3H)-one

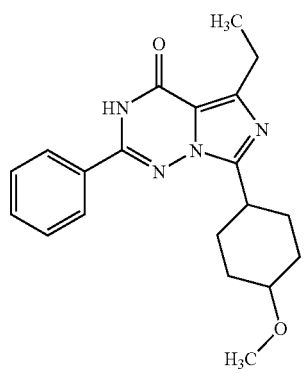

In analogy to the procedure for Example 1, 150 mg (0.40 mmol) of Example 62A, 250 mg (1.61 mmol) phosphoric trichloride are stirred at reflux for 3 hours, proportionate amounts of the solvents are used.

Yield: 19 mg (13%)

LC/MS (A): MS (ESI): 353 (M+H$^+$), retention time 3.26 min.

Example 29

7-Bicyclo[2.2.1]hept-5-en-2-yl-5-ethyl-2-phenylimidazo[5,1-f][1,2,4]triazin-4(3H)-one

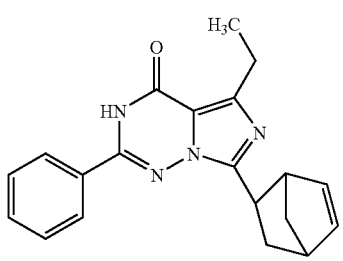

In analogy to the procedure for Example 1, 150 mg (0.43 mmol) of Example 63A, 250 mg (1.61 mmol) phosphoric trichloride are stirred at reflux for 3 hours, proportionate amounts of the solvents are used.

Yield: 25 mg (17%)

LC/MS (A): MS (ESI): 333 (M+H$^+$), retention time 3.49 min.

Example 30

7-Cycloheptyl-5-ethyl-2-phenylimidazo[5,1-f][1,2,4]triazin-4(3H)-one

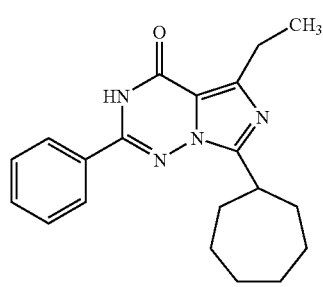

In analogy to the procedure for Example 1, 150 mg (0.42 mmol) of Example 64A, 250 mg (1.61 mmol) phosphoric trichloride are stirred at reflux for 3 hours, proportionate amounts of the solvents are used.

Yield: 72 mg (50%)

LC/MS (A): MS (ES): 337 (M+H$^+$), retention time 3.98 min.

Example 31

7-tert-Butyl-5-ethyl-2-phenylimidazo[5,1-f][1,2,4]triazin-4(3H)-one

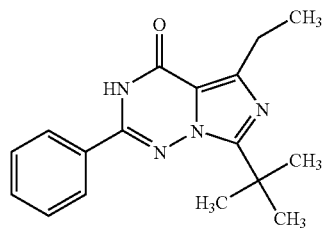

In analogy to the procedure for Example 1, 130 mg (0.41 mmol) of Example 65A, 250 mg (1.61 mmol) phosphoric trichloride are stirred at reflux for 3 hours, proportionate amounts of the solvents are used.

Yield: 28 mg (23%)

LC/MS (A): MS (ESI): 297 (M+H$^+$), retention time 3.45 min.

Example 32

7-sec-Butyl-5-ethyl-2-phenylimidazo[5,1-f][1,2,4]triazin-4(3H)-one

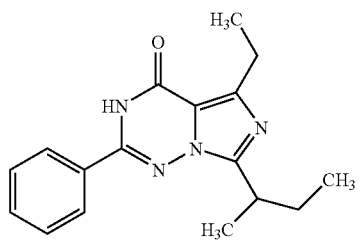

In analogy to the procedure for Example 1, 130 mg (0.41 mmol) of Example 66A, 250 mg (1.61 mmol) phosphoric trichloride are stirred at reflux for 3 hours, proportionate amounts of the solvents are used.

Yield: 52 mg (42%)

LC/MS (A): MS (ESI): 297 (M+H$^+$), retention time 3.41 min.

Example 33

5-Ethyl-7-(1-ethylpropyl)-2-phenylimidazo[5,1-f][1,2,4]triazin-4(3H)-one

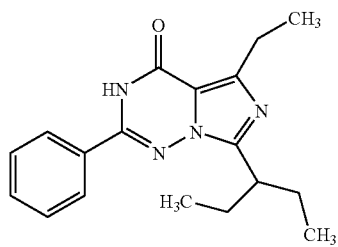

In analogy to the procedure for Example 1, 130 mg (0.40 mmol) of Example 67A, 250 mg (1.61 mmol) phosphoric trichloride are stirred at reflux for 3 hours, proportionate amounts of the solvents are used.

Yield: 52 mg (43%)

LC/MS (A): MS (ESI): 311 (M+H$^+$), retention time 3.64 min.

Example 34

5-Ethyl-7-tert-pentyl-2-phenylimidazo[5,1-f][1,2,4]triazin-4(3H)-one

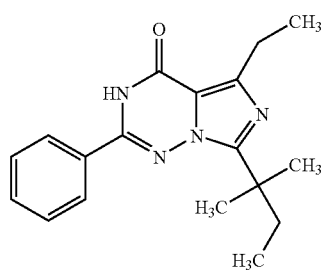

In analogy to the procedure for Example 1, 130 mg (0.40 mmol) of Example 68A, 250 mg (1.61 mmol) phosphoric trichloride are stirred at reflux for 3 hours, proportionate amounts of the solvents are used.

Yield: 21 mg (17%)

LC/MS (A): MS (ESI): 311 (M+H$^+$), retention time 3.66 min.

Example 35

5-Ethyl-7-(2-oxobicyclo[2.2.1]hept-7-yl)-2-phenylimidazo[5,1-f][1,2,4]triazin-4(3H)-one

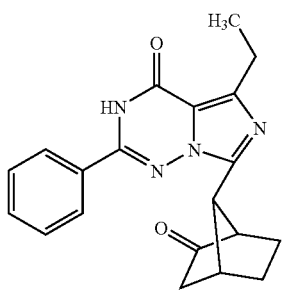

In analogy to the procedure for Example 1, 150 mg (0.41 mmol) of Example 69A, 250 mg (1.61 mmol) phosphoric trichloride are stirred at reflux for 3 hours, proportionate amounts of the solvents are used.

Yield: 1.5 mg (1%)

LC/MS (A): MS (ESI): 349 (M+H$^+$), retention time 3.44 min.

Example 36

5-Ethyl-2-phenyl-7-(2,2,2-trifluoroethyl)imidazo[5,1-f][1,2,4]triazin-4(3H)-one

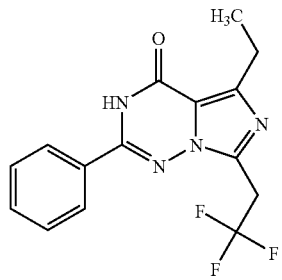

In analogy to the procedure for Example 1, 150 mg (0.44 mmol) of Example 70A, 250 mg (1.61 mmol) phosphoric trichloride are stirred at reflux for 3 hours, proportionate amounts of the solvents are used.

Yield: 32 mg (23%)

LC/MS (A): MS (ESI): 323 (M+H$^+$), retention time 3.70 min.

Example 37

5-Ethyl-7-(1-methylcyclohexyl)-2-phenylimidazo[5,1-f][1,2,4]triazin-4(3H)-one

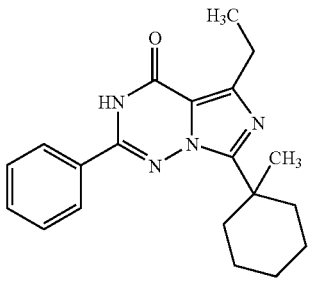

In analogy to the procedure for Example 1, 157 mg (0.44 mmol) of Example 71A, 250 mg (1.61 mmol) phosphoric trichloride are stirred at reflux for 3 hours, proportionate amounts of the solvents are used.

Yield: 62 mg (42%)

LC/MS (A): MS (ESI): 337 (M+H$^+$), retention time 4.13 min.

Example 38

5-Ethyl-7-(2-fluoro-1,1-dimethylethyl)-2-phenylimidazo[5,1-f][1,2,4]triazin-4(3H)-one

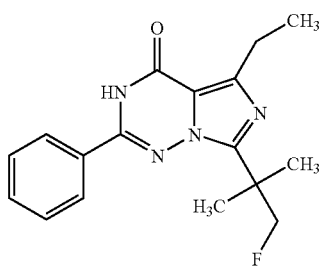

In analogy to the procedure for Example 1, 150 mg (0.45 mmol) of Example 72A, 250 mg (1.61 mmol) phosphoric trichloride are stirred at reflux for 3 hours, proportionate amounts of the solvents are used.

Yield: 46 mg (32%)

LC/MS (A): MS (ESI): 315 (M+H$^+$), retention time 3.76 min.

Example 39

7-(Bicyclo[2.2.1]hept-2-ylmethyl)-5-ethyl-2-phenylimidazo[5,1-f][1,2,4]triazin-4(3H)-one

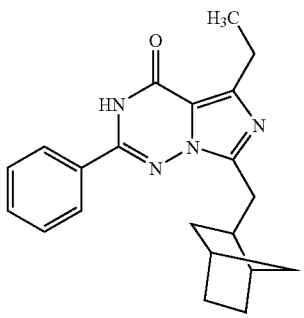

In analogy to the procedure for Example 1, 150 mg (0.41 mmol) of Example 73A, 250 mg (1.61 mmol) phosphoric trichloride are stirred at reflux for 3 hours, proportionate amounts of the solvents are used.

Yield: 50 mg (35%)

LC/MS (A): MS (ESI): 349 (M+H$^+$), retention time 4.02 min.

Example 40

5-Ethyl-7-isobutyl-2-phenylimidazo[5,1-f][1,2,4]triazin-4(3H)-one

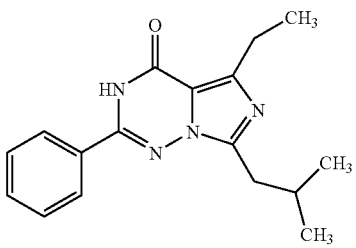

In analogy to the procedure for Example 1, 150 mg (0.48 mmol) of Example 74A, 250 mg (1.61 mmol) phosphoric trichloride are stirred at reflux for 3 hours, proportionate amounts of the solvents are used.

Yield: 20 mg (14%)

LC/MS (A): MS (ESI): 297 (M+H$^+$), retention time 3.37 min.

Example 41

5-Ethyl-2-phenyl-7-[4-(trifluoromethyl)cyclohexyl]imidazo[5,1-f][1,2,4]triazin-4(3H)-one (Isomer A)

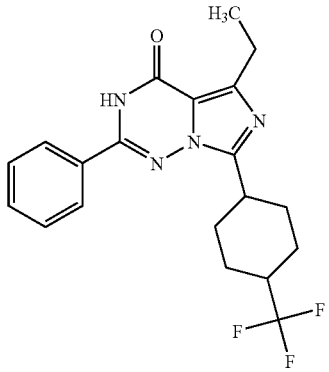

In analogy to the procedure for Example 1, 170 mg (0.42 mmol) of Example 75A, 250 mg (1.61 mmol) phosphoric trichloride are stirred at reflux for 3 hours, proportionate amounts of the solvents are used.

Yield: 7.5 mg (4.6%)

$^1$H-NMR (200 MHz, DMSO): 1.23 (t, 3H); 1.68–1.97 (m, 5H); 2.07–2.42 (m, 4H); 2.91 (quart., 2H); 3.50–3.73 (m, 1H); 7.57 (m, 3H); 7.98 (m, 2H); 11.89 (s, 1H) ppm.

Example 42

5-Ethyl-2-phenyl-7-[4-(trifluoromethyl)cyclohexyl]imidazo[5,1-f][1,2,4]triazin-4(3H)-one (Isomer B)

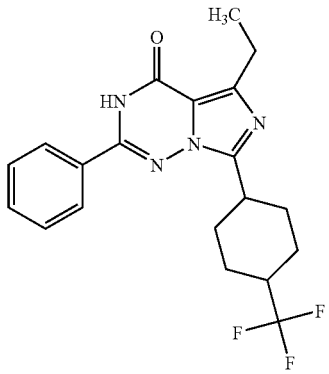

In analogy to the procedure for Example 1, 170 mg (0.42 mmol) of Example 75A, 165 mg (1.07 mmol) phosphoric trichloride are stirred at reflux for 3 hours, proportionate amounts of the solvents are used.

Yield: 6 mg (3.7%)

¹H-NMR (200 MHz, DMSO): 1.22 (t, 3H); 1.39–2.40 (m, 9H); 2.88 (m, 2H); 3.15–3.32 (m, 1H); 7.57 (m, 3H); 7.99 (m, 2H); 11.87 (s, 1H) ppm.

Example 43

5-Ethyl-2-phenyl-7-[3-(trifluoromethyl)cyclohexyl]imidazo[5,1-f][1,2,4]triazin-4(3H)-one (Isomer A)

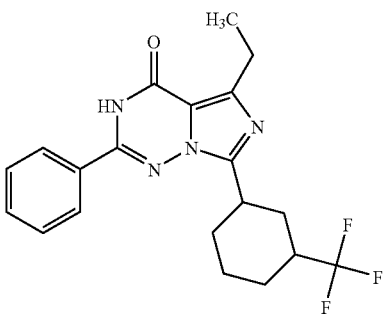

In analogy to the procedure for Example 1, 170 mg (0.42 mmol) of Example 76A, 165 mg (1.07 mmol) phosphoric trichloride are stirred at reflux for 3 hours, proportionate amounts of the solvents are used.

Yield: 7.5 mg (4.6%)

¹H-NMR (200 MHz, DMSO): 1.27 (t, 3H); 1.30–2.32 (m, 9H); 2.92 (m, 2H); 3.75 (m, 1H); 7.57 (m, 3H); 7.98 (m, 2H); 12.01 (s, 1H) ppm.

Example 44

5-Ethyl-2-phenyl-7-[3-(trifluoromethyl)cyclohexyl]imidazo[5,1-f][1,2,4]triazin-4(3H)-one (Isomer B)

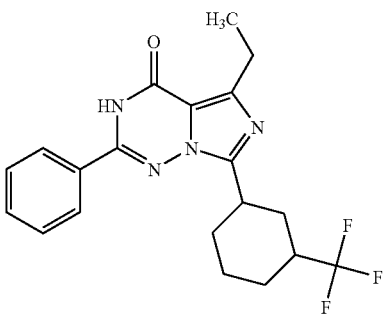

In analogy to the procedure for Example 1, 170 mg (0.42 mmol) of Example 76A, 165 mg (1.07 mmol) phosphoric trichloride are stirred at reflux for 3 hours, proportionate amounts of the solvents are used.

Yield: 23 mg (14%)

¹H-NMR (200 MHz, DMSO): 1.26 (t, 3H); 1.30–2.20 (m, 9H); 2.90 (quart., 2H); 3.38 (m, 1H); 7.57 (m, 3H); 7.98 (m, 2H); 11.94 (s, 1H) ppm.

Example 45

7-(1,4-Dimethylcyclohexyl)-5-ethyl-2-phenylimidazo[5,1-f][1,2,4]triazin-4(3H)-one (Isomer A)

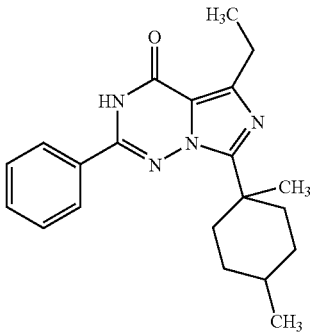

In analogy to the procedure for Example 1, 160 mg (0.43 mmol) of Example 77A, 165 mg (1.07 mmol) phosphoric trichloride are stirred at reflux for 3 hours, proportionate amounts of the solvents are used.

Yield: 14.6 mg (9.6%)

¹H-NMR (300 MHz, DMSO): 0.78 (d, 3H); 1.03 (m, 2H); 1.23 (t, 3H); 1.36 (s, 3H); 1.38–1.57 (m, 3H); 2.26–2.59 (m, 4H); 2.88 (quart., 2H); 7.57 (m, 3H); 7.96 (m, 2H); 11.91 (s, 1H) ppm.

Example 46

7-(1,4-Dimethylcyclohexyl)-5-ethyl-2-phenylimidazo[5,1-f][1,2,4]triazin-4(3H)-one (Isomer B)

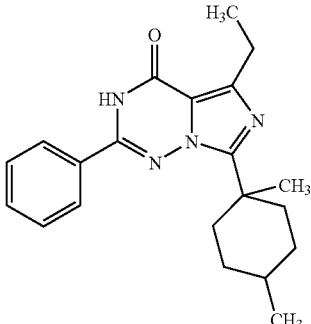

In analogy to the procedure for Example 1, 160 mg (0.43 mmol) of Example 77A, 165 mg (1.07 mmol) phosphoric trichloride are stirred at reflux for 3 hours, proportionate amounts of the solvents are used.

Yield: 28.8 mg (19%)

¹H-NMR (300 MHz, DMSO): 0.92 (dd, 3H); 1.22 (t, 3H); 1.41 (m, 1H); 1.49 (d, 3H); 1.58–1.72 (m, 4H); 1.81 (m, 1H); 1.97–2.10 (m, 3H); 2.91 (quart., 2H); 7.58 (m, 3H); 7.96 (m, 2H); 11.97 (s, 1H) ppm.

Example 47

5-Ethyl-7-(4-methylcyclohexyl)-2-phenylimidazo[5,1-f][1,2,4]triazin-4(3H)-one

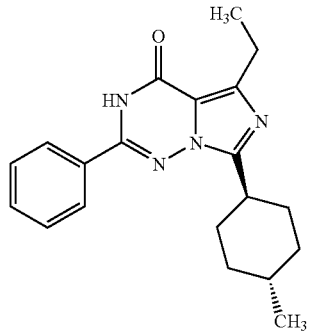

In analogy to the procedure for Example 1, 150 mg (0.42 mmol) of Example 78A, 165 mg (1.07 mmol) phosphoric trichloride are stirred at reflux for 3 hours, proportionate amounts of the solvents are used.

Yield: 41 mg (29%)

$^1$H-NMR (200 MHz, DMSO): 0.93 (d, 3H); 1.22 (t, 3H); 1.38–1.99 (m, 9H); 2.91 (quart., 2H); 3.14 (m, 1H); 7.57 (m, 3H); 7.97 (m, 2H); 11.98 (s, 1H) ppm.

Example 48

7-(Cyclohexylmethyl)-5-ethyl-2-phenylimidazo[5,1-f][1,2,4]triazin-4(3H)-one

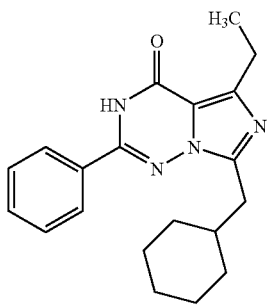

In analogy to the procedure for Example 1, 150 mg (0.42 mmol) of Example 79A, 165 mg (1.07 mmol) phosphoric trichloride are stirred at reflux for 3 hours, proportionate amounts of the solvents are used.

Yield: 23 mg (16%)

$^1$H-NMR (300 MHz, DMSO): 0.93–1.21 (m, 6H); 1.25 (t, 3H); 1.67 (m, 4H); 1.86 (m, 1H); 2.83–2.94 (m, 4H); 7.58 (m, 3H); 7.97 (dd, 2H); 11.93 (s, 1H) ppm.

Example 49

5,7-Diethyl-2-phenylimidazo[5,1-f][1,2,4]triazin-4(3H)-one

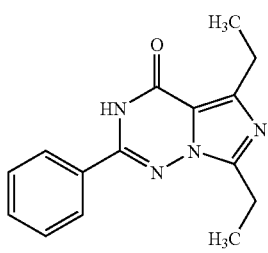

In analogy to the procedure for Example 1, 120 mg (0.42 mmol) of Example 80A, 165 mg (1.07 mmol) phosphoric trichloride are stirred at reflux for 3 hours, proportionate amounts of the solvents are used.

Yield: 10.5 mg (9.3%)

$^1$H-NMR (300 MHz, DMSO): 1.26–1.34 (m, 6H); 2.88–3.03 (m, 4H); 7.58 (m, 3H); 7.98 (dd, 2H); 12.02 (s, 1H) ppm.

Example 50

7-Butyl-5-ethyl-2-phenylimidazo[5,1-f][1,2,4]triazin-4(3H)-one

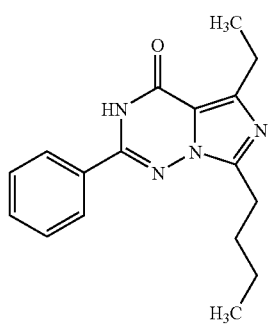

In analogy to the procedure for Example 1, 130 mg (0.41 mmol) of Example 81A, 165 mg (1.07 mmol) phosphoric trichloride are stirred at reflux for 4 hours, proportionate amounts of the solvents are used.

Yield: 27 mg (22%)

$^1$H-NMR (300 MHz, DMSO): 0.90 (t, 3H); 1.25 (t, 3H); 1.38 (sex., 2H); 1.75 (quin., 2H); 2.88–3.02 (m, 4H); 7.58 (m, 3H); 7.98 (dd, 2H); 12.03 (s, 1H) ppm.

Example 51

5-Ethyl-7-pentyl-2-phenylimidazo[5,1-f][1,2,4]triazin-4(3H)-one

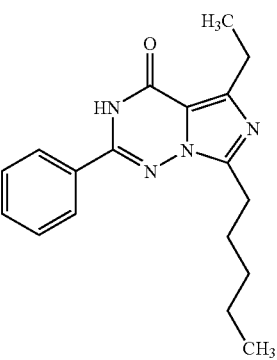

In analogy to the procedure for Example 1, 140 mg (0.42 mmol) of Example 82A, 165 mg (1.07 mmol) phosphoric trichloride are stirred at reflux for 4 hours, proportionate amounts of the solvents are used.

Yield: 31 mg (24%)

$^1$H-NMR (300 MHz, DMSO): 0.88 (t, 3H); 1.23 (t, 3H); 1.33 (m, 4H); 1.76 (quin., 2H); 2.87–2.99 (m, 4H); 7.58 (m, 3H); 7.98 (dd, 2H); 12.02 (s, 1H) ppm.

Example 52

5-Ethyl-7-heptyl-2-phenylimidazo[5,1-f][1,2,4]triazin-4(3H)-one

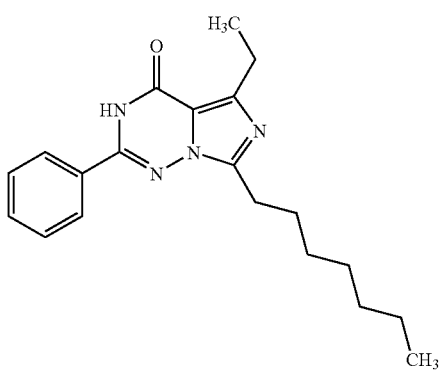

In analogy to the procedure for Example 1, 150 mg (0.42 mmol) of Example 83A, 165 mg (1.07 mmol) phosphoric trichloride are stirred at reflux for 4 hours, proportionate amounts of the solvents are used.

Yield: 31 mg (22%)

$^1$H-NMR (300 MHz, DMSO): 0.85 (t, 3H); 1.20–1.33 (m, 11H); 1.78 (quin., 2H); 2.92–3.07 (m, 4H); 7.58 (m, 3H); 7.98 (dd, 2H); 12.21 (s, 1H) ppm.

Example 53

5-Ethyl-7-hexyl-2-phenylimidazo[5,1-f][1,2,4]triazin-4(3H)-one

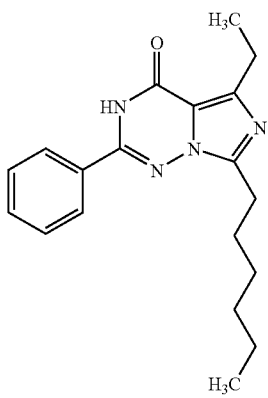

In analogy to the procedure for Example 1, 140 mg (0.41 mmol) of Example 84A, 165 mg (1.07 mmol) phosphoric trichloride are stirred at reflux for 4 hours, proportionate amounts of the solvents are used.

Yield: 25 mg (19%)

$^1$H-NMR (300 MHz, DMSO): 0.86 (t, 3H); 1.24 (t, 3H); 1.31 (m, 6H); 1.76 (quin., 2H); 2.88–3.00 (m, 4H); 7.56 (m, 3H); 7.97 (dd, 2H); 11.98 (s, 1H) ppm.

Example 54

5-Ethyl-7-isopropyl-2-phenylimidazo[5,1-f][1,2,4]triazin-4(3H)-one

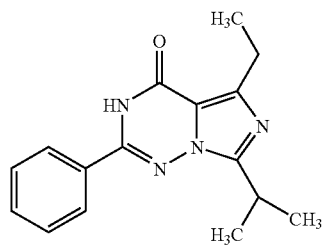

In analogy to the procedure for Example 1, 130 mg (0.43 mmol) of Example 85A, 165 mg (1.08 mmol) phosphoric trichloride are stirred at reflux for 4 hours, proportionate amounts of the solvents are used.

Yield: 51 mg (42%)

$^1$H-NMR (200 MHz, DMSO): 1.23 (t, 3H); 1.32 (d, 6H); 2.88 (quart., 2H); 3.49 (in, 1H); 7.55 (m, 3H); 7.97 (dd, 2H); 11.82 (s, 1H) ppm.

Example 55

5-Ethyl-7-neopentyl-2-phenylimidazo[5,1-f][1,2,4]triazin-4(3H)-one

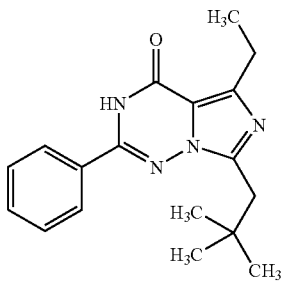

In analogy to the procedure for Example 1, 140 mg (0.43 mmol) of Example 86A, 165 mg (1.08 mmol) phosphoric trichloride are stirred at reflux for 4 hours, proportionate amounts of the solvents are used.

Yield: 37 mg (28%)

$^1$H-NMR (200 MHz, DMSO): 0.99 (s, 9H); 1.18 (m, 2H); 1.22 (t, 3H); 2.84 (m, 2H); 7.56 (m, 3H); 7.97 (m, 2H); 11.83 (s, 1H) ppm.

Example 56

5-Ethyl-7-(methoxymethyl)-2-phenylimidazo[5,1-f][1,2,4]triazin-4(3H)-one

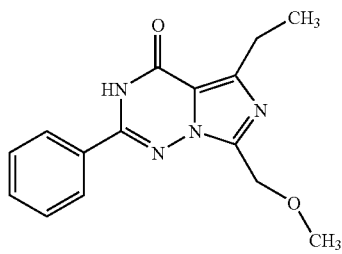

In analogy to the procedure for Example 1, 130 mg (0.43 mmol) of Example 87A, 165 mg (1.08 mmol) phosphoric trichloride are stirred at reflux for 4 hours, proportionate amounts of the solvents are used.

Yield: 26 mg (21%)

$^1$H-NMR (200 MHz, DMSO): 1.23 (t, 3H); 2.88 (quart., 2H); 3.30 (s, 2H); 3.50 (s, 3H), 7.55 (m, 3H); 7.97 (dd, 2H); 11.82 (s, 1H) ppm.

Example 57

5-Ethyl-7-(3-methoxycyclohexyl)-2-phenylimidazo[5,1-f][1,2,4]triazin-4(3H)-one

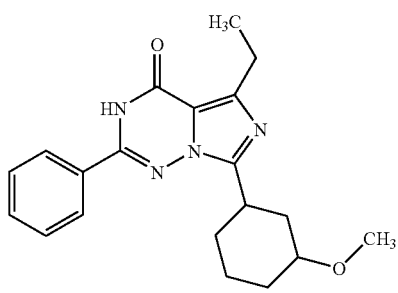

In analogy to the procedure for Example 1, 160 mg (0.43 mmol) of Example 88A, 165 mg (1.08 mmol) phosphoric trichloride are stirred at reflux for 4 hours, proportionate amounts of the solvents are used.

Yield: 54 mg (35%)

$^1$H-NMR (200 MHz, DMSO): 0.79 (quart., 4H); 1.24 (t, 3H); 1.76 (m, 4H); 2.93 (quart., 2H); 3.33 (m, 2H); 3.49 (s, 3H); 7.59 (m, 3H); 7.96 (m, 2H); 12.01 (s, 1H) ppm.

Example 58

5-Ethyl-7-(1-ethylpentyl)-2-phenylimidazo[5,1-f][1,2,4]triazin-4(3H)-one

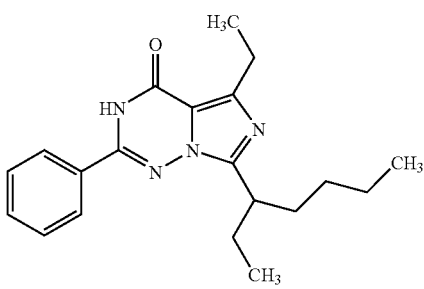

In analogy to the procedure for Example 1, 150 mg (0.42 mmol) of Example 89A, 165 mg (1.08 mmol) phosphoric trichloride are stirred at reflux for 4 hours, proportionate amounts of the solvents are used.

Yield: 36 mg (25%)

$^1$H-NMR (200 MHz, DMSO): 0.79 (m, 6H); 1.02–1.28 (m, 7H); 1.78 (m, 4H); 2.92 (quart., 2H); 3.31 (m, 1H); 7.57 (m, 3H); 7.96 (m, 2H); 12.01 (s, 1H) ppm.

Example 59

5-Ethyl-7-(1-methylbutyl)-2-phenylimidazo[5,1-f][1,2,4]triazin-4(3H)-one

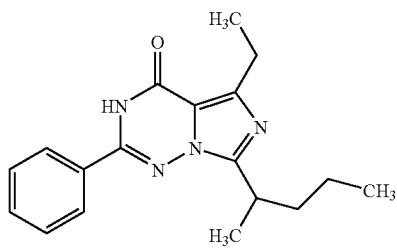

In analogy to the procedure for Example 1, 140 mg (0.43 mmol) of Example 90A, 165 mg (1.08 mmol) phosphoric trichloride are stirred at reflux for 4 hours, proportionate amounts of the solvents are used.

Yield: 38 mg (29%)

$^1$H-NMR (200 MHz, DMSO): 0.86 (t, 3H); 1.19–1.34 (m, 8H); 1.65 (m, 1H); 1.79 (m, 1H); 2.92 (quart., 2H); 3.47 (m, 1H); 7.59 (m, 3H); 7.97 (m, 2H); 12.00 (s, 1H) ppm.

Example 60

7-(2-Cyclopentylethyl)-5-ethyl-2-phenylimidazo[5,1-f][1,2,4]triazin-4(3H)-one

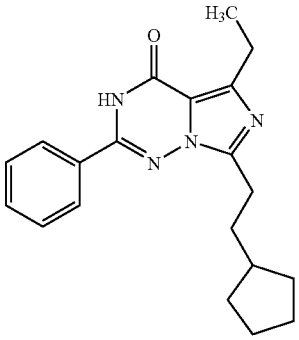

In analogy to the procedure for Example 1, 150 mg (0.43 mmol) of Example 91A, 165 mg (1.08 mmol) phosphoric trichloride are stirred at reflux for 4 hours, proportionate amounts of the solvents are used.

Yield: 62 mg (44%)

$^1$H-NMR (200 MHz, DMSO): 1.14 (m, 2H); 1.25 (t, 3H); 1.41–1.60 (m, 4H); 1.68–1.83 (m, 5H); 2.93 (m, 4H); 7.60 (m, 3H); 7.97 (m, 2H); 12.11 (s, 1H) ppm.

Example 61

5-Ethyl-2-phenyl-7-propylimidazo[5,1-f][1,2,4]triazin-4(3H)-one

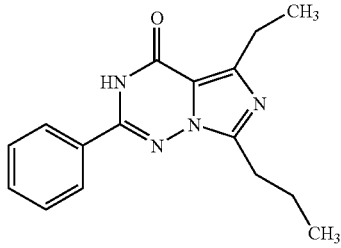

In analogy to the procedure for Example 1, 127 mg (0.42 mmol) of Example 92A, 165 mg (1.08 mmol) phosphorictrichloride are stirred at reflux for 4 hours, proportionate amounts of the solvents are used.

Yield: 35 mg (29%)

$^1$H-NMR (200 MHz, DMSO): 0.97 (t, 3H); 1.23 (t, 3H); 1.78 (sex., 2H); 2.82–2.97 (m, 4H); 7.57 (m, 3H); 7.96 (m, 2H); 11.98 (s, 1H) ppm.

Example 62

5-Ethyl-7-(4-ethylcyclohexyl)-2-phenylimidazo[5,1-f][1,2,4]triazin-4(3H)-one

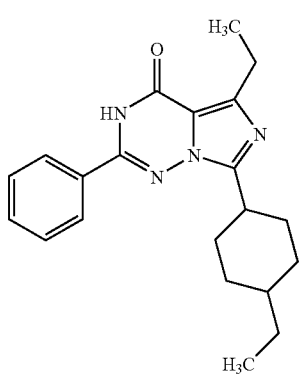

In analogy to the procedure for Example 1, 150 mg (0.41 mmol) of Example 93A, 165 mg (1.07 mmol) phosphoric trichloride are stirred at reflux for 4 hours, proportionate amounts of the solvents are used.

Yield: 46 mg (32%)

$^1$H-NMR (300 MHz, DMSO): 0.88 (m, 3H); 1.26 (m, 6H); 1.57–1.71 (m, 4H); 1.86 (m, 2H); 1.98 (m, 2H); 2.88 (quart., 2H); 3.13 (m, 1H); 7.55 (m, 3H); 7.96 (m, 2H); 11.78 (s, 1H) ppm.

Example 63

5-Ethyl-2-phenyl-7-(3,3,5-trimethylcyclohexyl)imidazo[5,1-f][1,2,4]triazin-4(3H)-one

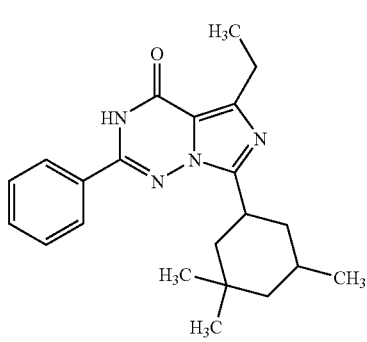

In analogy to the procedure for Example 1, 150 mg (0.39 mmol) of Example 94A, 165 mg (1.07 mmol) phosphoric trichloride are stirred at reflux for 4 hours, proportionate amounts of the solvents are used.

Yield: 27 mg (19%)

$^1$H-NMR (300 MHz, DMSO): 0.90 (m, 4H); 0.96 (s, 3H); 1.02 (s, 3H); 1.21 (m, 4H); 1.42 (m, 2H); 1.63 (m, 1H); 1.77 (m, 1H); 1.90 (m, 1H); 2.88 (quart., 2H); 3.42 (m, 1H); 7.55 (m, 3H); 7.97 (m, 2H); 11.78 (s, 1H) ppm.

Example 64

7-(4,4-Dimethylcyclohexyl)-5-ethyl-2-phenylimidazo[5,1-f][1,2,4]triazin-4(3H)-one

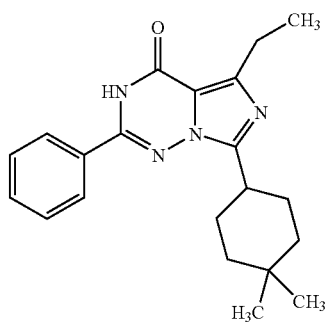

In analogy to the procedure for Example 1, 150 mg (0.41 mmol) of Example 95A, 165 mg (1.07 mmol) phosphoric trichloride are stirred at reflux for 4 hours, proportionate amounts of the solvents are used.

Yield: 25 mg (17%)

$^1$H-NMR (300 MHz, DMSO): 0.98 (d, 6H); 1.23 (m, 4H); 1.36 (m, 2H); 1.49 (m, 2H); 1.77 (m, 2H); 1.86 (m, 1H); 2.89 (q, 2H); 3.08 (m, 1H); 7.55 (m, 3H); 7.96 (m, 2H); 11.77 (s, 1H) ppm.

Example 65

7-Cyclopentyl-5-ethyl-2-(1-naphthyl)imidazo[5,1-f][1,2,4]triazin-4(3H)-one

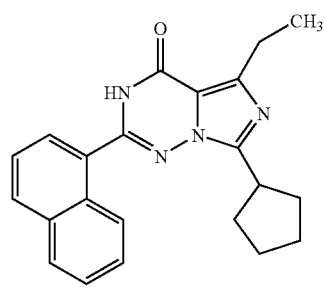

A solution of 600 mg (1.59 mmol) of Example 96A and 293 mg (1.91 mmol) phosphoric trichloride in 10 m 1,2-dichloroethane is stirred at reflux for 4 hours. After work-up analogously to the procedure given for Example 1, the product is obtained as a solid.

Yield: 375 mg (64%)

Melting point: 167° C.

$^1$H-NMR (DMSO-$d_6$, 200 MHz): δ=11.9 (s, 1H) 8.3–7.5 (m, 7H), 3.5 (m, 1H), 2.9 (q, J=7.5 Hz, 2H), 2.1–1.5 (m, 8H), 1.3 (t, J=7.5 Hz, 3H) ppm.

Example 66

7-Cyclopentyl-5-ethyl-2-(4-methyl-1-naphthyl)imidazo[5,1-f][1,2,4]triazin-4(3H)-one

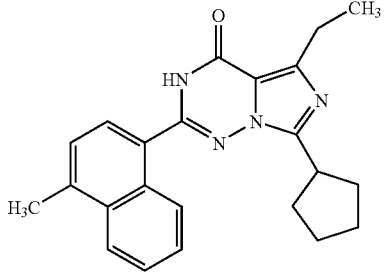

In analogy to the procedure for Example 1, 797 mg (2.04 mmol) crude N-{1-[3-(4-methyl-1-naphthyl)-5-oxo-4,5-dihydro-1,2,4-triazin-6-yl]propyl}cyclopentanecarboxamide, 469 mg (3.06 mmol) phosphoric trichloride are stirred at reflux for 3 hours, proportionate amounts of the solvents are used.

Yield: 360 mg (47%)

$^1$H-NMR (CD$_3$OD, 300 MHz): δ=1.14 (t, 3H), 1.43–1.99 (m, 8H), 2.60 (s, 3H), 2.84 (q, 2H), 3.44 (quin., 1H), 7.30 (d, 1H), 7.38–7.50 (m, 3H), 7.95–8.02 (m, 2H) ppm.

Example 67

7-Cyclopentyl-5-ethyl-2-(4-methylphenyl)imidazo[5,1-f][1,2,4]triazin-4(3H)-one

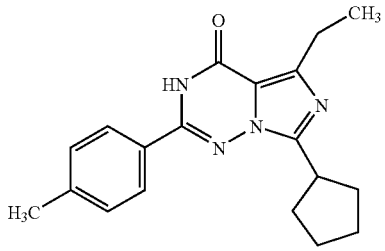

In analogy to the procedure for Example 1, 320 mg (0.94 mmol) of Example 115A, 216 mg (1.41 mmol) phosphoric trichloride are stirred at reflux over night, proportionate amounts of the solvents are used.

Yield: 271 mg (89%)

$^1$H-NMR (DMSO-d$_6$, 300 MHz): δ=1.2 (t, 3H), 1.7 (m, 2H), 1.8 (m, 2H), 1.9 (m, 2H), 2.1 (m, 2H), 2.4 (s, 3H), 3.0 (q, 2H), 3.7 (m, 1H), 7.4 (m, 2H), 7.9 (m, 2H), 12.2 (s, 1H) ppm.

Example 68

7-Cyclobutyl-5-ethyl-2-(4-methylphenyl)imidazo[5,1-f][1,2,4]triazin-4(3H)-one

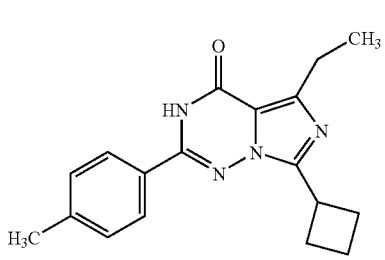

In analogy to the procedure for Example 1, 420 mg (1.29 mmol) of Example 114A, 296 mg (1.93 mmol) phosphoric trichloride are stirred at reflux over night, proportionate amounts of the solvents are used.

Yield: 400 mg (quant.)

$^1$H-NMR (DMSO-d$_6$, 300 MHz): δ=1.2 (t, 3H), 1.9 (m, 1H), 2.2 (m, 1H), 2.4 (m, 2H, s, 3H), 2.6 (m, 2H), 3.0 (q, 2H), 4.2 (m, 1H), 7.4 (m, 2H), 7.9 (m, 2H), 12.3 (s, 1H) ppm.

Example 69

7-Cyclopentyl-5-ethyl-2-(4-nitrophenyl)imidazo[5,1-f][1,2,4]triazin-4(3H)-one

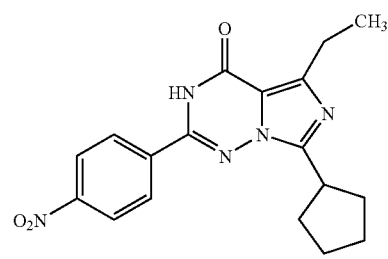

300 mg (1.09 mmol) of Example 110A are suspended in 10 ml dichloroethane, and 165 mg (1.63 mmol) triethylamine and 217 mg (1.09 mmol) cyclopentanecarbonyl chloride are added. The mixture is stirred at room temperature for one hour, then 167 mg (1.09 mmol) phosphoroxychloride are added. The mixture is stirred at reflux for 3 hours. After cooling down to room temperature, ethyl acetate and saturated NaHCO$_3$ (aq) are added. The organic phase is washed with saturated NaHCO$_3$ (aq), water and brine, dried over sodium sulfate and evaporated to dryness in vacuo. The product is purified by chromatography (flash or column chromatography or preparative HPLC).

Yield: 5 mg (2%)

LC/MS (A): MS (ESI): 354 (M+H$^+$), retention time 2.63 min.

Example 70

2-(4-Butylphenyl)-7-cyclopentyl-5-ethylimidazo[5,1-f][1,2,4]triazin-4(3H)-one

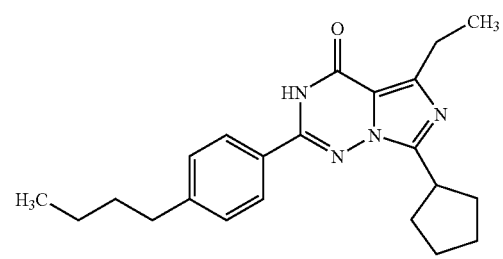

In analogy to the procedure for Example 69, 100 mg (0.35 mmol) of Example 111A, 46 mg (0.35 mmol) cyclopentanecarbonyl chloride and proportionate amounts of the other reagents are used.

Yield: 27 mg (21%)

$^1$H-NMR (DMSO-d$_6$, 300 MHz): δ=0.9 (t, 3H), 1.2 (t, 3H), 1.3 (m, 2H), 1.6 (m, 4H), 1.8 (m, 4H), 2.1 (m, 2H), 2.7 (t, 2H), 2.9 (q, 2H), 3.6 (m, 1H), 7.4 (m, 2H), 7.9 (m, 2H), 11.7 (s, 1H) ppm.

Example 71

2-Cyclopentyl-5-ethyl-7-(2-methylcyclopropyl)imidazo[5,1-f][1,2,4]triazin-4(3H)-one

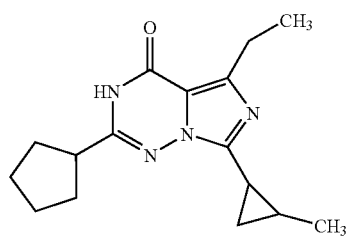

In analogy to the procedure for Example 1, 200 mg (0.66 mmol) crude N-[1-(3-cyclopentyl-5-oxo-4,5-dihydro-1,2,4-triazin-6-yl)propyl]-2-methylcyclopropanecarboxamide, 165 mg (1.1 mmol) phosphoric trichloride are stirred at reflux for 4 hours, proportionate amounts of the solvents are used. The isomers are purified by chromatography (preparative HPLC).

Yield: 44 mg (24%) major isomer, racemate

LC/MS (B): MS (ESI): 287 (M+H$^+$), retention time 3.51 min $^1$H-NMR (200 MHz, DMSO-d$_6$): δ=0.85 (m, 1H), 1.05–1.25 (m, 7H), 1.30–1.48 (m, 1H), 1.5–2.1 (m, 9H), 2.76 (q, 2H), 2.91 (quintett,1H), 11.30 (s, 1H) ppm.

Example 72

2-Cyclopentyl-5-ethyl-7-cyclopropylimidazo[5,1-f][1,2,4]triazin-4(3H)-one

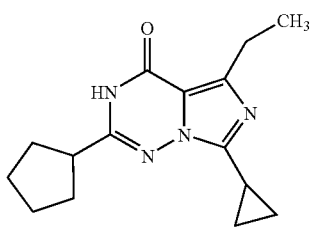

In analogy to the procedure for Example 1, 200 mg (0.66 mmol) crude N-[1-(3-cyclopentyl-5-oxo-4,5-dihydro-1,2,4-triazin-6-yl)propyl]cyclopropanecarboxamide, 165 mg (1.1 mmol) phosphoric trichloride are stirred at reflux for 4 hours, proportionate amounts of the solvents are used. The product is purified by chromatography (preparative HPLC).

Yield: 77 mg (44%)

LC/MS (B): MS (ESI): 273 (M+H$^+$), retention time 3.30 min $^1$H-NMR (200 MHz, DMSO-d$_6$): δ=0.95–1.06 (m, 4H), 1.14 (t, 3H), 1.54–2.02 (m, 8H), 2.32 (m, 1H), 2.77 (q, 2H), 2.92 (quintett, 1H), 11.32 (s, 1H) ppm.

Example 73 and Example 74

2-Cyclopentyl-7-(1,4-dimethylcyclohexyl)-5-ethylimidazo[5,1-f][1,2,4]triazin-4(3H)-one

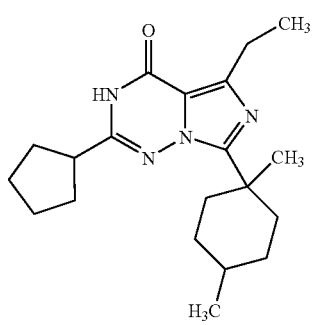

In analogy to the procedure for Example 1, 200 mg (0.55 mmol) crude N-[1-(3-cyclopentyl-5-oxo-4,5-dihydro-1,2,4-triazin-6-yl)propyl]-1,4-dimethylcyclohexanecarboxamide, 165 mg (1.1 mmol) phosphoric trichloride are stirred at reflux for 4 hours, proportionate amounts of the solvents are used. The isomers are purified by chromatography (preparative HPLC).

Yield: 86 mg (45%) major isomer (Example 73)

LC/MS (B): MS (ESI): 343 (M+H$^+$), retention time 4.38 min $^1$H-NMR (200 MHz, DMSO-d$_6$): δ=0.89 (m, 3H), 1.17 (t, 3H), 1.24–1.31 (m, 2H), 1.42 (d, 3H), 1.5–2.1 (m, 15H), 2.81 (q, 2H), 2.95 (quintett, 1H), 11.45 (s, 1H) ppm.

Yield: 39 mg (20%) minor isomer (Example 74)

LC/MS (B): MS (ESI): 343 (M+H$^+$), retention time 4.66 min $^1$H-NMR (200 MHz, DMSO-d$_6$): δ=0.7–2.05 (m, 24H), 2.65–3.05 (m, 5H), 11.46 (s, 1H) ppm.

Example 75 and Example 76

7-Bicyclo[2.2.1]hept-5-en-2-yl-2-cyclopentyl-5-ethylimidazo[5,1-f][1,2,4]triazin-4(3H)-one

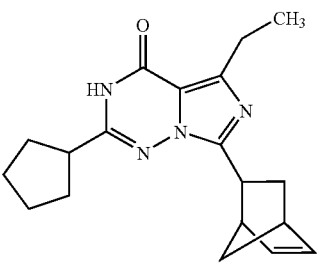

In analogy to the procedure for Example 1, 200 mg (0.58 mmol) crude N-[1-(3-cyclopentyl-5-oxo-4,5-dihydro-1,2,4-triazin-6-yl)propyl]bicyclo[2.2.1]hept-5-ene-2-carboxamide, 165 mg (1.1 mmol) phosphoric trichloride are stirred at reflux for 4 hours, proportionate amounts of the solvents are used. The isomers are purified by chromatography (preparative HPLC).

Yield: 44 mg (23%) major isomer (Example 75)
LC/MS (B): MS (ESI): 325 (M+H⁺), retention time 3.56 min Yield: 33 mg (18%) minor isomer (Example 76)
LC/MS (B): MS (ESI): 325 (M+H⁺), retention time 4.20 min.

Example 77

7-(Bicyclo[2.2.1]hept-2-ylmethyl)-2-cyclopentyl-5-ethylimidazo[5,1-f][1,2,4]triazin-4(3H)-one

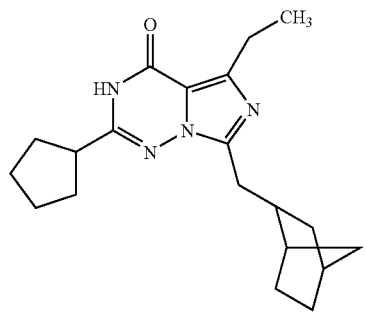

In analogy to the procedure for Example 1, 200 mg (0.56 mmol) crude 2-bicyclo[2.2.1]hept-2-yl-N-[1-(3-cyclopentyl-5-oxo-4,5-dihydro-1,2,4-triazin-6-yl)-propyl]acetamide, 165 mg (1.1 mmol) phosphoric trichloride are stirred at reflux for 4 hours, proportionate amounts of the solvents are used. The product is purified by chromatography (preparative HPLC).

Yield: 103 mg (54%)
LC/MS (B): MS (ESI): 341 (M+H⁺), retention time 4.16 min.

Example 78 and Example 79

2-Cyclopentyl-5-ethyl-7-(2-methylcyclohexyl)imidazo[5,1-f][1,2,4]triazin-4(3H)-one

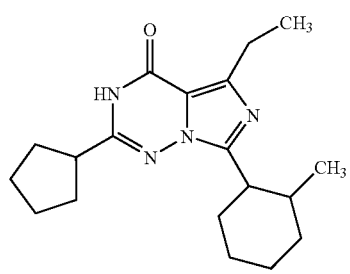

In analogy to the procedure for Example 1, 200 mg (0.58 mmol) crude N-[1-(3-cyclopentyl-5-oxo-4,5-dihydro-1,2,4-triazin-6-yl)propyl]-2-methylcyclohexanecarboxamide, 165 mg (1.1 mmol) phosphoric trichloride are stirred at reflux for 4 hours, proportionate amounts of the solvents are used. The isomers are purified by chromatography (preparative HPLC).

Yield: 51 mg (27%) cis-isomer, racemate (Example 78)
LC/MS (B): MS (ESI): 329 (M+H⁺), retention time 4.01 min
¹H-NMR (200 MHz, DMSO-d₆): δ=0.61 (d, 3H), 0.95–1.45 (m, 6H), 1.5–2.05 (m, 14H), 2.65–3.0 (m, 4H), 11.4 (s, 1H) ppm.

Yield: 32 mg (18%) trans-isomer, racemate (Example 79)
LC/MS (B): MS (ESI): 329 (M+H⁺), retention time 4.17 min
¹H-NMR (200 MHz, DMSO-d₆): δ=0.66 (d, 3H), 1.1–1.25 (m, 4H), 1.3–2.25 (m, 19H), 2.83 (q, 2H) 2.92 (m, 1H), 3.09 (d of q, 1H), 3.4 (m, 1H), 11.37 (s, 1H) ppm.

Example 80

2-Cyclopentyl-5-ethyl-7-isobutylimidazo[5,1-f][1,2,4]triazin-4(3H)-one

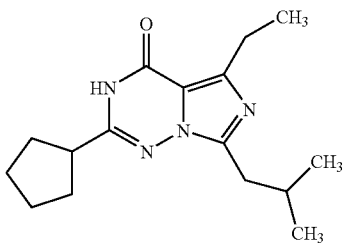

In analogy to the procedure for Example 1, 200 mg (0.65 mmol) crude N-[1-(3-cyclopentyl-5-oxo-4,5-dihydro-1,2,4-triazin-6-yl)propyl]-3-methylbutanamide, 165 mg (1.1 mmol) phosphoric trichloride are stirred at reflux for 4 hours, proportionate amounts of the solvents are used. The product is purified by chromatography (preparative HPLC).

Yield: 103 mg (55%)
LC/MS (B): MS (ESI): 289 (M+H⁺), retention time 3.46 min
¹H-NMR (200 MHz, DMSO-d₆): δ=0.89 (d, 6H), 1.18 (t, 3H), 1.55–2.02 (m, 8H), 2.11 (septett, 1H), 2.72 (d, 2H), 2.83 (q, 2H), 2.93 (quintett, 1H), 11.38 (s, 1H) ppm.

Example 81

2-Cyclopentyl-5-ethyl-7-(1-methylcyclohexyl)imidazo[5,1-f][1,2,4]triazin-4(3H)-one

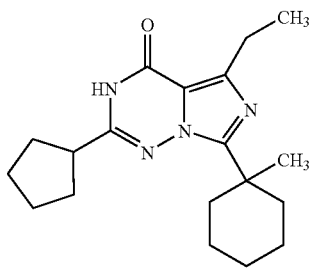

In analogy to the procedure for Example 1, 200 mg (0.58 mmol) crude N-[1-(3-cyclopentyl-5-oxo-4,5-dihydro-1,2,4-triazin-6-yl)propyl]-1-methylcyclohexanecarboxamide, 165 mg (1.1 mmol) phosphoric trichloride are stirred at reflux for 4 hours, proportionate amounts of the solvents are used. The product is purified by chromatography (preparative HPLC).

Yield: 105 mg (55%)

LC/MS (B): MS (ESI): 329 (M+H⁺), retention time 4.22 min

¹H-NMR (200 MHz, DMSO-d$_6$): δ=1.18 (t, 3H), 1.32 (s, 3H), 1.35–2.02 (m, 16H), 2.45 (m, 2H), 2.82 (q, 2H), 2.95 (quintett, 1H), 11.42 (s, 1H) ppm.

Example 82

7-Butyl-2-cyclopentyl-5-ethylimidazo[5,1-f][1,2,4]triazin-4(3H)-one

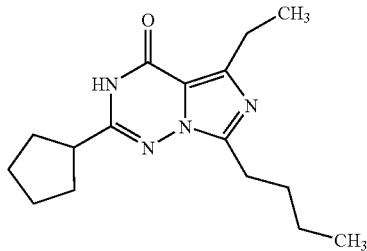

In analogy to the procedure for Example 1, 200 mg (0.65 mmol) crude N-[1-(3-cyclopentyl-5-oxo-4,5-dihydro-1,2,4-triazin-6-yl)propyl]pentanamide, 165 mg (1.1 mmol) phosphoric trichloride are stirred at reflux for 4 hours, proportionate amounts of the solvents are used. The product is purified by chromatography (preparative HPLC).

Yield: 73 mg (39%)

LC/MS (B): MS (ESI): 289 (M+H⁺), retention time 3.55 min

¹H-NMR (200 MHz, DMSO-d$_6$): δ=0.89 (t, 3H), 1.18 (t, 3H), 1.31 (sextett, 2H), 1.5–2.02 (m, 10H), 2.75–2.9 (m, 4H), 2.92 (quintett, 1H), 11.37 (s, 1H) ppm.

Example 83

7-(1-Adamantyl)-2-cyclopentyl-5-ethylimidazo[5,1-f][1,2,4]triazin-4(3H)-one

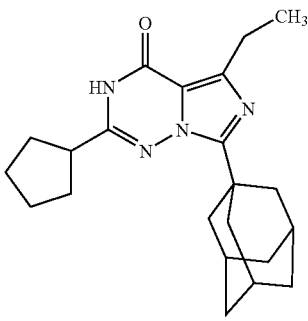

In analogy to the procedure for Example 1, 200 mg (0.52 mmol) crude N-[1-(3-cyclopentyl-5-oxo-4,5-dihydro-1,2,4-triazin-6-yl)propyl]-1-adamantanecarboxamide, 165 mg (1.1 mmol) phosphoric trichloride are stirred at reflux for 4 hours, proportionate amounts of the solvents are used. The product is purified by chromatography (preparative HPLC).

Yield: 146 mg (77%)

LC/MS (B): MS (ESI): 368 (M+H⁺), retention time 4.35 min.

Example 84

7-tert-Butyl-2-cyclopentyl-5-ethylimidazo[5,1-f][1,2,4]triazin-4(3H)-one

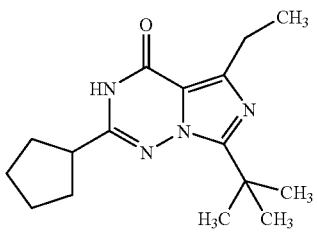

In analogy to the procedure for Example 1, 200 mg (0.65 mmol) crude N-[1-(3-cyclopentyl-5-oxo-4,5-dihydro-1,2,4-triazin-6-yl)propyl]-2,2-dimethylpropanamide, 165 mg (1.1 mmol) phosphoric trichloride are stirred at reflux for 4 hours, proportionate amounts of the solvents are used. The product is purified by chromatography (preparative HPLC).

Yield: 96 mg (50%)

LC/MS (B): MS (ESI): 289 (M+H⁺), retention time 3.55 min

¹H-NMR (200 MHz, DMSO-d$_6$): δ=1.18 (t, 3H), 1.43 (s, 9H), 1.55–2.02 (m, 8H), 2.81 (q, 2H), 2.96 (quintett, 1H), 11.42 (s, 1H) ppm.

Example 85

7-(Cyclohexylmethyl)-2-cyclopentyl-5-ethylimidazo[5,1-f][1,2,4]triazin-4(3H)-one

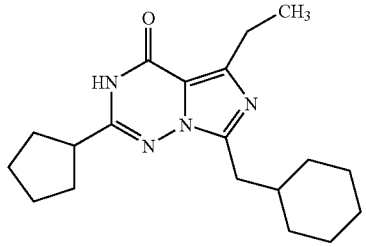

In analogy to the procedure for Example 1, 200 mg (0.52 mmol) crude 2-cyclohexyl-N-[1-(3-cyclopentyl-5-oxo-4,5-dihydro-1,2,4-triazin-6-yl)propyl]acetamide, 165 mg (1.1 mmol) phosphoric trichloride are stirred at reflux for 4 hours, proportionate amounts of the solvents are used. The product is purified by chromatography (preparative HPLC).

Yield: 72 mg (41%)

LC/MS (B): MS (ESI): 329 (M+H⁺), retention time 4.02 min

¹H-NMR (200 MHz, DMSO-d$_6$): δ=0.85–1.30 (m, 8H), 1.43–2.02 (m, 14H), 2.73 (d, 2H), 2.81 (q, 2H), 2.92 (quintett, 1H), 11.41 (s, 1H) ppm.

Example 86

2-Cyclopentyl-5-ethyl-7-(1-ethylpentyl)imidazo[5,1-f][1,2,4]triazin-4(3H)-one

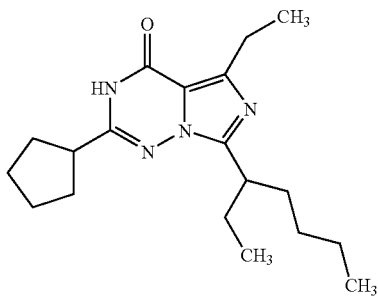

In analogy to the procedure for Example 1, 190 mg (0.55 mmol) crude N-[1-(3-cyclopentyl-5-oxo-4,5-dihydro-1,2,4-triazin-6-yl)propyl]-2-ethylhexanamide, 165 mg (1.1 mmol) phosphoric trichloride are stirred at reflux for 4 hours, proportionate amounts of the solvents are used. The product is purified by chromatography (preparative HPLC).

Yield: 100 mg (56%)

LC/MS (B): MS (ESI): 331 (M+H$^+$), retention time 4.28 min $^1$H-NMR (200 MHz, DMSO-d$_6$): δ=0.71 (t, 3H), 0.79 (t, 3H), 0.95–1.32 (m, 4H), 1.18 (t, 3H), 1.45–2.05 (m, 12H), 2.83 (q, 2H), 2.94 (quintett, 1H), 3.16 (t of t, 1H), 11.42 (s, 1H) ppm.

Example 87

2-Cyclopentyl-5-ethyl-7-tert-pentylimidazo[5,1-f][1,2,4]triazin-4(3H)-one

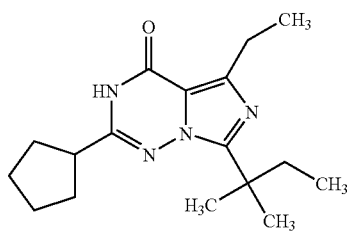

In analogy to the procedure for Example 1, 211 mg (0.66 mmol) crude N-[1-(3-cyclopentyl-5-oxo-4,5-dihydro-1,2,4-triazin-6-yl)propyl]-2,2-dimethylbutanamide, 165 mg (1.1 mmol) phosphoric trichloride are stirred at reflux for 4 hours, proportionate amounts of the solvents are used. The product is purified by chromatography (preparative HPLC).

Yield: 67 mg (34%)

LC/MS (B): MS (ESI): 303 (M+H$^+$), retention time 3.83 min $^1$H-NMR (200 MHz, DMSO-d$_6$): δ=0.61 (t, 3H), 1.17 (t, 3H), 1.39 (s, 6H), 1.5–2.05 (m, 10H), 2.81 (q, 2H), 2.96 (quintett, 1H), 11.47 (s, 1H) ppm.

Example 88

Benzyl 4-(2-cyclopentyl-5-ethyl-4-oxo-3,4-dihydroimidazo[5,1-f][1,2,4]triazin-7-yl)-1-piperidinecarboxylate

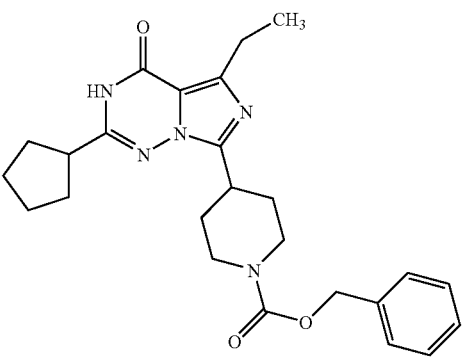

In analogy to the procedure for Example 1, 500 mg (1.07 mmol) crude benzyl 4-({[1-(3-cyclopentyl-5-oxo-4,5-dihydro-1,2,4-triazin-6-yl)propyl]amino}carbonyl)-1-piperidinecarboxylate, 248 mg (1.7 mmol) phosphoric trichloride are stirred at reflux for 4 hours, proportionate amounts of the solvents are used. The product is purified by chromatography (preparative HPLC).

Yield: 207 mg (43%)

LC/MS (B): MS (ESI): 450 (M+H$^+$), retention time 4.17 min $^1$H-NMR (200 MHz, DMSO-d$_6$): δ=1.17 (t, 3H), 1.45–2.05 (m, 12H), 2.81 (q, 2H), 2.94 (quintett, 1H), 2.99 (m, 2H), 3.25 (m, 1H), 3.95–4.15 (m, 2H), 5.1 (s, 2H), 7.37 (m, 5H), 11.47 (s, 1H) ppm.

Example 89

5-Ethyl-2-phenyl-7-(1-propylbutyl)imidazo[5,1-f][1,2,4]triazin-4(3H)-one

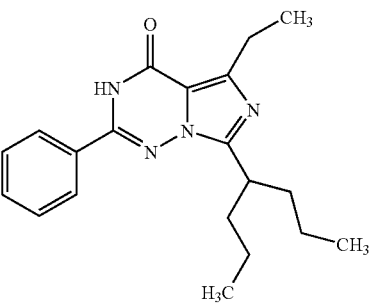

In analogy to the procedure for Example 1, 150 mg (0.42 mmol) of Example 131A, 165 mg (1.08 mmol) phosphoric trichloride are stirred at reflux for 4 hours, proportionate amounts of the solvents are used.

Yield: 36 mg (25%)

$^1$H-NMR (200 MHz, DMSO): 0.81 (t, 6H); 1.17 (m, 4H); 1.23 (t, 3H); 1.59–1.88 (m, 4H); 2.92 (quart., 2H); 3.43 (m, 1H); 7.57 (m, 3H); 7.97 (dd, 2H); 11.96 (s, 1H).

Example 90

5-Ethyl-7-(4-isopropylcyclohexyl)-2-phenylimidazo[5,1-f][1,2,4]triazin-4(3H)-one

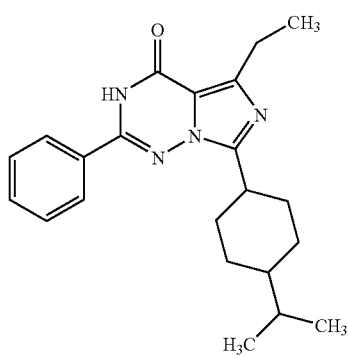

In analogy to the procedure for Example 1, 150 mg (0.42 mmol) of Example 132A, 165 mg (1.08 mmol) phosphoric trichloride are stirred at reflux for 4 hours, proportionate amounts of the solvents are used.

Yield: 26.6 mg (18.6%)

$^1$H-NMR (300 MHz, DMSO): δ=0.90 (d, 6H); 1.20–2.10 (m, 10H); 2.90 (quart., 2H); 3.10 (m, 1H); 7.57 (m, 3H); 7.97 (dd, 2H); 11.80 (s, 1H).

Example 91

5-Ethyl-7-(2-methylbicyclo[2.2.1]hept-2-yl)-2-phenylimidazo[5,1-f][1,2,4]triazin-4(3H)-one

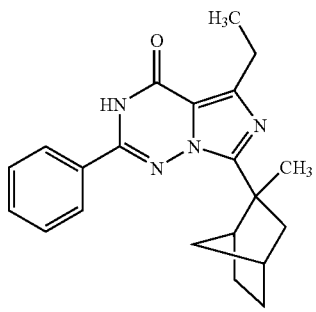

In analogy to the procedure for Example 1, 150 mg (0.42 mmol) of Example 133A, 165 mg (1.08 mmol) phosphoric trichloride are stirred at reflux for 4 hours, proportionate amounts of the solvents are used.

Yield: 90 mg (63%)

$^1$H-NMR (200 MHz, DMSO): δ=1.20–1.60 (m, 12H); 1.80 (m, 1H); 2.20 (m, 1H); 2.70–3.10 (m, 4H); 7.57 (m, 3H); 7.97 (m, 2H); 11.90 (s, 1H).

Example 92

5-Ethyl-7-(4-cis-methylcyclohexyl)-2-phenylimidazo[5,1-f][1,2,4]triazin-4(3H)-one

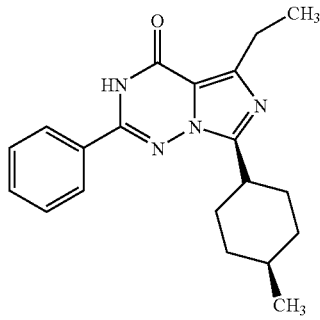

In analogy to the procedure for Example 1, 149 mg (0.42 mmol) of Example 134A, 165 mg (1.07 mmol) phosphoric trichloride are stirred at reflux for 3 hours, proportionate amounts of the solvents are used.

Yield: 43 mg (30%)

$^1$H-NMR (200 MHz, DMSO): 0.93 (d, 3H); 1.22 (t, 314); 1.50–1.85 (m, 7H); 2.00 (m, 2H); 2.91 (quart., 2H); 3.30 (m, 1H); 7.57 (m, 3H); 7.95 (m, 2H); 11.85 (s, 1H).

Example 93

5-Ethyl-7-(2-methylcyclohexyl)-2-phenylimidazo[5,1-f][1,2,4]triazin-4(3H)-one

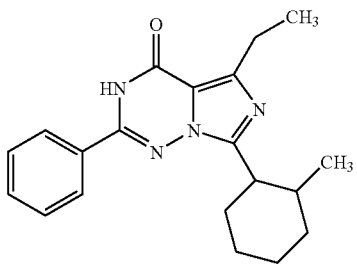

In analogy to the procedure for Example 1, 150 mg (0.42 mmol) of Example 135A, 165 mg (1.07 mmol) phosphoric trichloride are stirred at reflux for 3 hours, proportionate amounts of the solvents are used.

Yield: 67 mg (47%) of a 1:1 cis/trans isomeric mixture $^1$H-NMR (200 MHz, DMSO): 0.70 (m, 3H); 1.10–2.20 (m, 12H); 2.91 (m, 2.5H); 3.60 (m, 0.5H); 7.57 (m, 3H); 8.00 (m, 2H); 12 (2s, 1H).

Example 94 and Example 95

5-Ethyl-2-(1-naphthyl)-7-[3-(trifluoromethyl)cyclohexyl]imidazo[5,1-f][1,2,4]triazin-4(3H)-one

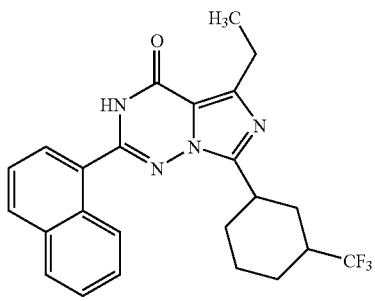

In analogy to the procedure for Example 1, 160 mg (0.35 mmol) of Example 136A, 165 mg (1.07 mmol) phosphoric trichloride are stirred at reflux for 3 hours, proportionate amounts of the solvents are used.

Yield: 4 mg (2.6%) isomer A (Example 94)

LC/MS (B): MS (ESI): 441 (M+H$^+$), retention time 4.63 min

Yield: 17 mg (11%) isomer B (Example 95)

LC/MS (B): MS (ESI): 441 (M+H$^+$), retention time 5.06 min.

Example 96

5-Ethyl-2-(1-naphthyl)-7-[4-(trifluoromethyl)cyclohexyl]imidazo[5,1-f][1,2,4]triazin-4(3H)-one

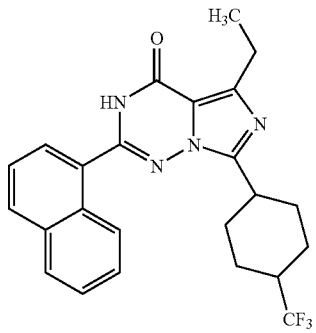

In analogy to the procedure for Example 1, 160 mg (0.35 mmol) of Example 137A, 165 mg (1.07 mmol) phosphoric trichloride are stirred at reflux for 3 hours, proportionate amounts of the solvents are used.

Yield: 3.6 mg (2.3%)

$^1$H-NMR (200 MHz, DMSO): 1.30 (t, 3H); 1.60–2.20 (m, 9H); 2.91 (quart., 2H); 3.40 (m, 1H); 7.60 (m, 3H); 7.80 (m, 1H); 8.10 (m, 3H); 12.00 (s, 1H).

Example 97

7-(1,4-Dimethylcyclohexyl)-5-ethyl-2-(1-naphthyl)imidazo[5,1-f][1,2,4]triazin-4(3H)-one

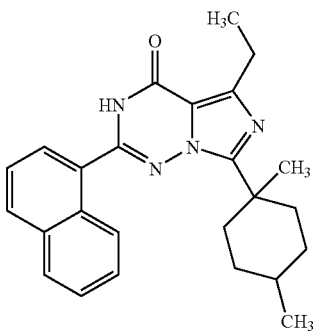

In analogy to the procedure for Example 1, 150 mg (0.36 mmol) of Example 138A, 165 mg (1.07 mmol) phosphoric trichloride are stirred at reflux for 3 hours, proportionate amounts of the solvents are used.

Yield: 89 mg (62%)

$^1$H-NMR (200 MHz, DMSO): 0.70–2.10 (m, 18H); 2.91 (quart., 2H); 7.60 (m, 3H); 7.80 (m, 1H); 8.10 (m, 3H); 12.10 (s, 1H).

Example 98

5-Ethyl-7-(4-methylcyclohexyl)-2-(1-naphthyl)imidazo[5,1-f][1,2,4]triazin-4(3H)-one

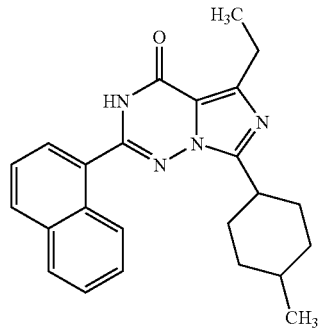

In analogy to the procedure for Example 1, 140 mg (0.35 mmol) of Example 139A, 165 mg (1.07 mmol) phosphoric trichloride are stirred at reflux for 3 hours, proportionate amounts of the solvents are used.

Yield: 63 mg (47%) of an isomeric mixture $^1$H-NMR (200 MHz, DMSO): 0.90–1.00 (2d, 3H); 1.10–2.00 (m, 12H); 3.00 (2 quart., 2H); 3.20 (m); 7.50–8.20 (m, 7H); 12.10 (s, 1H).

Example 99

7-(Cyclohexylmethyl)-5-ethyl-2-(1-naphthyl)imidazo[5,1-f][1,2,4]triazin-4(3H)-one

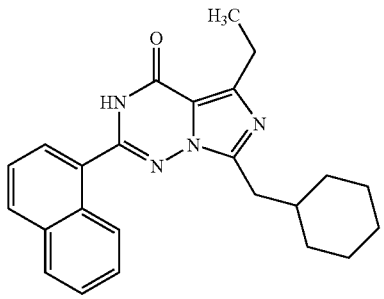

In analogy to the procedure for Example 1, 140 mg (0.35 mmol) of Example 140A, 165 mg (1.07 mmol) phosphoric trichloride are stirred at reflux for 3 hours, proportionate amounts of the solvents are used.

Yield: 69 mg (52%)

$^1$H-NMR (300 MHz, DMSO): 0.90–1.30 (m, 9H); 1.60 (m, 4H); 1.85 (m, 1H); 2.80 (d, 2H); 2.95 (quart., 2H); 7.60 (m, 3H); 7.80 (d, 1H); 8.05 (m, 1H); 8.20 (m, 2H); 12.20 (s, 1H).

Example 100

5-Ethyl-7-isobutyl-2-(1-naphthyl)imidazo[5,1-f][1,2,4]triazin-4(3H)-one

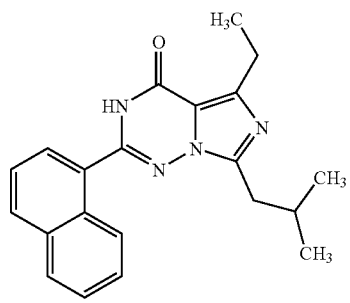

In analogy to the procedure for Example 1, 140 mg (0.35 mmol) of Example 141A, 165 mg (1.07 mmol) phosphoric trichloride are stirred at reflux for 3 hours, proportionate amounts of the solvents are used.

Yield: 75 mg (61%)

$^1$H-NMR (200 MHz, DMSO): 0.90 (d, 6H); 1.30 (t, 3H); 2.15 (m, 1H); 2.80 (d, 2H); 3.00 (quart., 2H); 7.60 (m, 3H); 7.80 (m, 1H); 8.10 (m, 2H); 12.20 (s, 1H).

Example 101

7-(1-Adamantyl)-5-ethyl-2-phenylimidazo[5,1-f][1,2,4]triazin-4(3H)-one

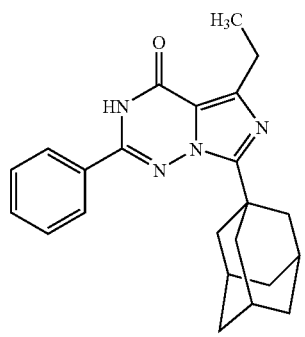

In analogy to the procedure for Example 1, 50 mg (0.13 mmol) of Example 142A, 165 mg (1.07 mmol) phosphoric trichloride are stirred at reflux for 3 hours, proportionate amounts of the solvents are used.

Yield: 14 mg (29%)

$^1$H-NMR (400 MHz, DMSO): 1.20 (t, 3H); 1.80 (m, 6H); 2.10 (m, 3H); 2.25 (m, 6H); 2.90 (quart., 2H); 7.50 (m, 3H); 8.00 (m, 2H); 11.80 (s, 1H).

Example 102

Benzyl 4-(5-ethyl-4-oxo-2-phenyl-3,4-dihydroimidazo[5,1-f][1,2,4]triazin-7-yl)-1-piperidinecarboxylate

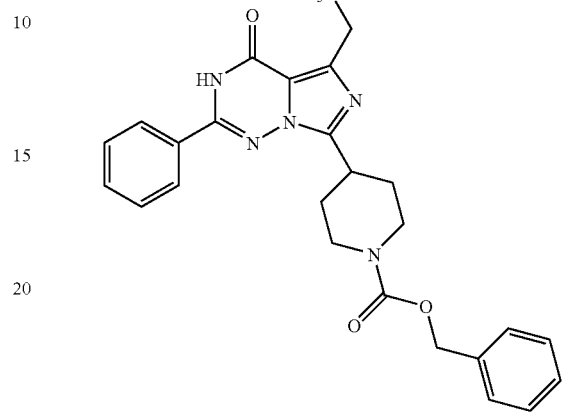

In analogy to the procedure for Example 1, 3.40 g (7.15 mmol) of Example 143A, 1.48 g (9.64 mmol) phosphoric trichloride are stirred at reflux for 3 hours, proportionate amounts of the solvents are used.

Yield: 2.51 g (71%)

$^1$H-NMR (300 MHz, DMSO): 1.30 (t, 3H); 2.00 (m, 4H); 3.70 (m., 1H); 4.15 (m, 2H); 5.10 (s, 2H); 7.20–7.70 (m, 7H); 8.00 (m, 2H); 12.40 (s, 1H).

Example 103

7-[1-(Cyclobutylcarbonyl)-4-piperidinyl]-5-ethyl-2-phenylimidazo[5,1-f][1,2,4]triazin-4(3H)-one

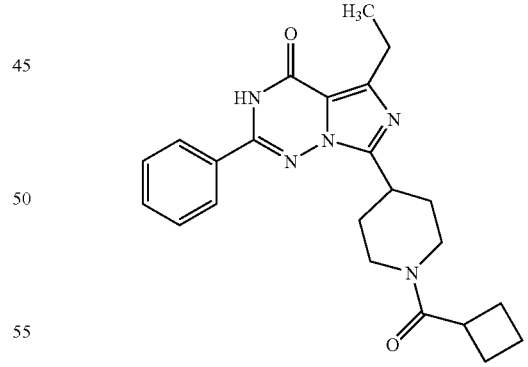

Step (a)

5-Ethyl-2-phenyl-7-(4-piperidinyl)imidazo[5,1-f][1,2,4]triazin-4(3H)-one 1.9 g (4.15 mmol) of Example 102 are dissolved in 75 mL ethanol. 0.5 g palladium on carbon are added and the mixture is hydrogenated overnight at room temperature. The suspension is filtered through silica gel, and the ethanol phase is concentrated under vacuum to yield the title compound, which is used without further purification.

Yield: 1.03 g (77%)

LC/MS (B): MS (ESI): 324 (M+H$^+$), retention time 1.75 min $^1$H-NMR (300 MHz, DMSO): 1.20 (t, 3H); 2.10 (m, 4H); 2.90 (q, 2H); 3.30 (m); 7.5 (m, 3H); 8.00 (m, 2H).

Step (b)

7-[1-(Cyclobutylcarbonyl)-4-piperidinyl]-5-ethyl-2-phenylimidazo[5,1-f][1,2,4]triazin-4(3H)-one 30 mg (0.093 mmol) of the compound from step (a) are suspended in 5 ml dichloroethane, 19 mg (0.09 mmol) triethylamine and 12 mg (0.1 mmol) cyclobutanecarbonyl chloride are added. The reaction mixture is stirred at room temperature overnight, concentrated under vacuum and purified by HPLC.

Yield: 3.1 mg (8.2%)

LC/MS (B): MS (ESI): 406 (M+H$^+$), retention time 3.50 min.

Example 104

7-[1-(Cyclopentylcarbonyl)-4-piperidinyl]-5-ethyl-2-phenylimidazo[5,1-f][1,2,4]triazin-4(3H)-one

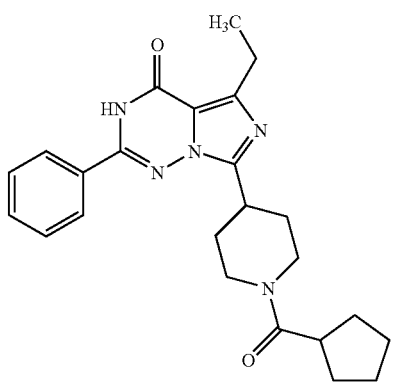

In analogy to the procedure for Example 103 Step (b), 30 mg (0.09 mmol) 5-ethyl-2-phenyl-7-(4-piperidinyl)imidazo[5,1-f][1,2,4]triazin-4(3H)-one, 14 mg (0.10 mmol) cyclopentanecarbonyl chloride are stirred at room temperature overnight, proportionate amounts of the solvents are used.

Yield: 11.9 mg (31%)

LC/MS (B): MS (ESI): 420 (M+H$^+$), retention time 3.69 min.

Example 105

7-(1-Benzoyl-4-piperidinyl)-5-ethyl-2-phenylimidazo[5,1-f][1,2,4]triazin-4(3H)-one

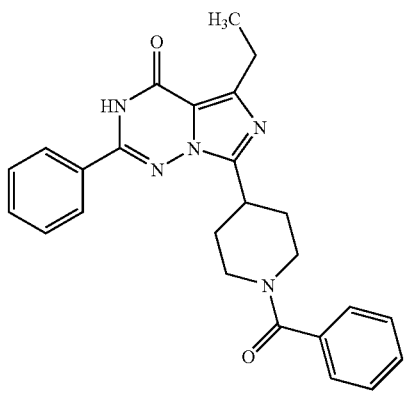

In analogy to the procedure for Example 103 Step (b), 30 mg (0.09 mmol) 5-ethyl-2-phenyl-7-(4-piperidinyl)imidazo[5,1-f][1,2,4]triazin-4(3H)-one, 14 mg (0.10 mmol) benzoyl chloride are stirred at room temperature overnight, proportionate amounts of the solvents are used.

Yield: 9 mg (23%)

LC/MS (B): MS (ESI): 428 (M+H$^+$), retention time 3.58 min.

We claim:
1. A compound of the general formula (I),

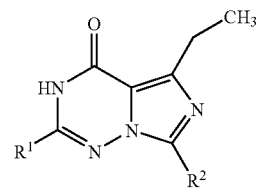

in which
$R^1$ denotes $(C_6-C_{10})$-aryl, which is optionally substituted by identical or different residues selected from the group consisting of halogen, $(C_1-C_6)$-alkyl, trifluoromethyl, cyano, nitro and trifluoromethoxy, or
denotes $(C_1-C_8)$-alkyl, which is optionally substituted by 3- to 10-membered carbocyclyl, or
denotes 3- to 10-membered carbocyclyl, which is optionally substituted by identical or different $(C_1-C_4)$-alkyl residues,
and
$R^2$ denotes 3- to 10-membered carbocyclyl or carbon-bonded, 4- to 10-membered heterocyclyl, said carbocyclyl and heterocyclyl being optionally substituted by identical or different residues selected from the group consisting of $(C_1-C_6)$-alkyl, $(C_1-C_6)$-alkoxy, $(C_1-C_6)$-alkoxycarbonyl, benzyloxycarbonyl, $(C_1-C_6)$-alkylcarbonyl, $(C_4-C_7)$-cycloalkylcarbonyl, benzoyl, hydroxy, halogen, trifluoromethyl and oxo,
or
denotes $(C_2-C_{10})$-alkyl, which is optionally substituted by identical or different residues selected from the group consisting of $(C_1-C_6)$-alkoxy, hydroxy, halogen, 3- to 10-membered carbocyclyl and oxo, or a salt thereof.

2. A compound according to claim 1, wherein
$R^1$ denotes naphthyl, or
denotes phenyl, which is optionally substituted by identical or different halogen atoms.

3. A compound according to claim 1 or 2, wherein
$R^2$ denotes $(C_4-C_7)$-cycloalkyl, which is optionally substituted up to two times by identical or different $(C_1-C_5)$-alkyl residues, or
denotes $(C_3-C_8)$-alkyl, which is optionally substituted by a $(C_4-C_7)$-cycloalkyl.

4. A process for the preparation of the compounds according to claim 1, characterized in that,
a compound of the general formula (IV),

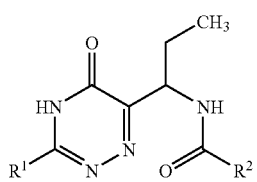

(IV)

in which
$R^1$ denotes $(C_6-C_{10})$-aryl, which is optionally substituted by identical or different residues selected from the group consisting of halogen, $(C_1-C_6)$-alkyl, trifluoromethyl, cyano, nitro and trifluoromethoxy, or
denotes $(C_1-C_8)$-alkyl, which is optionally substituted by 3- to 10-membered carbocyclyl, or
denotes 3- to 10-menabered carbocyclyl, which is optionally substituted by identical or different $(C_1-C_4$-alkyl residues,
and
$R^2$ denotes 3- to 10-membered carbocyclyl or carbon-bonded, 4- to 10-membered heterocyclyl, said carbocyclyl and heterocyclyl being optionally substituted by identical or different residues selected from the group consisting of $(C_2-C_6)$-alkyl, $(C_1-C_6)$-alkoxy, $(C_1-C_6)$-alkoxycarbonyl, benzyloxycarbonyl, $(C_1-C_6)$-alkylcarbonyl, $(C_4-C_7)$-cycloalkylcarbonyl, benzoyl, hydroxy, halogen, trifluoromethyl and oxo,
or
denotes $(C_2-C_{10})$-alkyl, which is optionally substituted by identical or different residues selected from the group consisting of $(C_1-C_6)$-alkoxy, hydroxy, halogen, 3- to 10-membered carbocyclyl and oxo, is reacted with a dehydrating agent.

5. A compound of the general formula (IV)

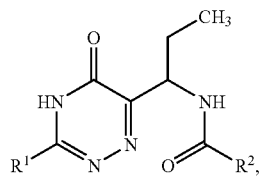

(IV)

wherein
$R^1$ denotes $(C_6-C_{10})$-aryl, which is optionally substituted by identical or different residues selected from the group consisting of halogen, $(C_1-C_6)$-alkyl, trifluoromethyl, cyano, nitro und trifluoromethoxy, or
denotes $(C_1-C_8)$-alkyl, which is optionally substituted by 3- to 10-membered carbocyclyl, or
denotes 3- to 10-membered carbocyclyl, which is optionally substituted by identical or different $(C_1-C_4)$-alkyl residues,
and
$R^2$ denotes 3- to 10-membered carbocyclyl or carbon-bonded, 4- to 10-membered heterocyclyl, said carbocyclyl and heterocyclyl being optionally substituted by identical or different residues selected from the group consisting of $(C_1-C_6)$-alkyl, $(C_1-C_6)$-alkoxy, $(C_1-C_6)$-alkoxycarbonyl, benzyloxycarbonyl, $(C_1-C_6)$-alkylcarbonyl, $(C_4-C_7)$-cycloalkylcarbonyl, benzoyl, hydroxy, halogen, trifluoromethyl and oxo,
or
denotes $(C_2-C_{10})$-alkyl, which is optionally substituted by identical or different residues selected from the group consisting of $(C_1-C_6)$-alkoxy, hydroxy, halogen, 3- 10-membered carbocyclyl and oxo.

6. A pharmaceutical composition containing at least one compound according to claim 1 and a pharmacologically acceptable diluent.

7. A method for treating chronic obstructive pulmonary disease or asthma, comprising administering to a patient a therapeutically effective amount of a compound of claim 1.

* * * * *